(12) United States Patent
Bullington et al.

(10) Patent No.: US 12,733,849 B2
(45) **Date of Patent: *Sep. 15, 2026**

(54) FLUID CONTROL DEVICES AND METHODS OF USING THE SAME

(71) Applicant: Magnolia Medical Technologies, Inc., Seattle, WA (US)

(72) Inventors: Gregory J. Bullington, Seattle, WA (US); Jay M. Miazga, Langley, WA (US); Shan E. Gaw, Seattle, WA (US); Timothy F. Ramsey, Seattle, WA (US)

(73) Assignee: Magnolia Medical Technologies, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/591,237

(22) Filed: Feb. 2, 2022

(65) Prior Publication Data

US 2022/0151526 A1 May 19, 2022

Related U.S. Application Data

(63) Continuation of application No. 17/516,887, filed on Nov. 2, 2021, which is a continuation of application (Continued)

(51) Int. Cl.
*A61B 5/15* (2006.01)
*A61B 10/00* (2006.01)

(52) U.S. Cl.
CPC .. *A61B 5/150251* (2013.01); *A61B 5/150099* (2013.01); *A61B 5/150221* (2013.01); *A61B 10/0045* (2013.01)

(58) Field of Classification Search
None
See application file for complete search history.

(56) References Cited

U.S. PATENT DOCUMENTS

| | | | |
|---|---|---|---|
| 2,674,265 | A | 4/1954 | Lee |
| 2,697,435 | A | 12/1954 | Benjamin |

(Continued)

FOREIGN PATENT DOCUMENTS

| | | | |
|---|---|---|---|
| AT | 310345 | B | 9/1973 |
| AT | E219383 | T1 | 7/2002 |

(Continued)

OTHER PUBLICATIONS

Office Action for U.S. Appl. No. 11/955,635, dated Jul. 22, 2010, 11 pages.

(Continued)

*Primary Examiner* — Matthew Kremer
(74) *Attorney, Agent, or Firm* — COOLEY LLP

(57) ABSTRACT

A fluid control device includes an inlet configured to be placed in fluid communication with a bodily fluid source and an outlet configured to be placed in fluid communication with a fluid collection device, which can produce a negative pressure differential between the outlet and the inlet. A sequestration portion is in fluid communication with the inlet and includes a first flow controller configured to transition from a first state to a second state to place the sequestration portion in fluid communication with the outlet when the negative pressure differential has a first magnitude. A sampling portion is in fluid communication with an outlet and includes a second flow controller configured to transition from a first state to a second state to place the sampling portion in fluid communication with the inlet when the negative pressure differential has a second magnitude greater than the first magnitude.

27 Claims, 9 Drawing Sheets

Related U.S. Application Data

No. 16/426,380, filed on May 30, 2019, now abandoned.

(60) Provisional application No. 62/678,637, filed on May 31, 2018.

(56) References Cited

U.S. PATENT DOCUMENTS 2,707,953 A 5/1955 Ryan
2,876,769 A 3/1959 Juan
2,952,258 A 9/1960 Chandler
2,992,974 A 7/1961 Belcove et al.
3,013,557 A 12/1961 Pallotta
3,098,016 A 7/1963 Cooper et al.
3,382,865 A 5/1968 Worral, Jr.
3,405,706 A 10/1968 Cinqualbre
3,467,021 A 9/1969 Green
3,467,095 A 9/1969 Ross
3,494,351 A 2/1970 Horn
3,494,352 A 2/1970 Russo et al.
3,577,980 A 5/1971 Cohen
3,596,652 A 8/1971 Winkelman
3,604,410 A 9/1971 Whitacre
3,635,798 A 1/1972 Kirkham et al.
3,640,267 A 2/1972 Hurtig et al.
3,648,684 A 3/1972 Barnwell et al.
3,650,093 A 3/1972 Rosenberg
3,680,558 A 8/1972 Kapelowitz
3,696,806 A 10/1972 Sausse et al.
3,705,018 A 12/1972 Taylor
3,730,168 A 5/1973 Mcwhorter
3,741,197 A 6/1973 Sanz et al.
3,749,084 A 7/1973 Cucchiara
3,777,773 A 12/1973 Tolbert
3,779,383 A 12/1973 Ayres
3,803,810 A 4/1974 Rosenberg
3,817,240 A 6/1974 Ayres
3,831,602 A 8/1974 Broadwin
3,834,372 A 9/1974 Turney
3,835,835 A 9/1974 Thompson et al.
3,848,579 A * 11/1974 Villa-Real ........ A61B 5/150221 600/577
3,848,581 A 11/1974 Cinqualbre et al.
3,859,998 A 1/1975 Thomas et al.
3,874,367 A 4/1975 Ayres
3,886,930 A 6/1975 Ryan
3,890,203 A 6/1975 Mehl
3,890,968 A 6/1975 Pierce et al.
3,937,211 A 2/1976 Merten
3,943,917 A 3/1976 Johansen
3,945,380 A 3/1976 Dabney et al.
3,960,139 A 6/1976 Bailey
3,978,846 A 9/1976 Bailey
3,996,923 A 12/1976 Guerra
4,056,101 A 11/1977 Geissler et al.
4,057,050 A 11/1977 Sarstedt
4,062,360 A 12/1977 Bentley
4,063,460 A 12/1977 Svensson
4,077,395 A 3/1978 Woolner
4,106,491 A 8/1978 Guerra
4,106,497 A 8/1978 Percarpio
4,133,304 A 1/1979 Bailey
4,133,863 A 1/1979 Koenig
4,150,089 A 4/1979 Linet
4,154,229 A 5/1979 Nugent
4,166,450 A 9/1979 Abramson
4,190,426 A 2/1980 Ruschke
4,193,400 A 3/1980 Loveless et al.
4,202,764 A 5/1980 Afflerbaugh et al.
4,206,282 A 6/1980 Hochstein
4,207,870 A 6/1980 Eldridge
4,210,173 A 7/1980 Choksi et al.
4,212,308 A 7/1980 Percarpio
4,226,236 A 10/1980 Genese
4,238,207 A 12/1980 Ruschke
4,257,416 A 3/1981 Prager
4,275,730 A 6/1981 Hussein
4,298,358 A 11/1981 Ruschke
4,312,362 A 1/1982 Kaufman
4,317,456 A 3/1982 Percarpio
4,327,746 A 5/1982 Feaster
4,340,067 A 7/1982 Rattenborg
4,340,068 A 7/1982 Kaufman
4,349,035 A 9/1982 Thomas et al.
4,354,507 A 10/1982 Raitto
4,370,987 A 2/1983 Bazell et al.
4,373,535 A 2/1983 Martell
4,398,544 A 8/1983 Nugent et al.
4,411,275 A 10/1983 Raitto
4,412,548 A 11/1983 Hoch
4,416,290 A 11/1983 Lutkowski
4,416,291 A 11/1983 Kaufman
4,425,235 A 1/1984 Cornell et al.
4,436,098 A 3/1984 Kaufman
4,444,203 A 4/1984 Engelman
4,459,997 A 7/1984 Sarstedt
4,496,458 A 1/1985 Lee
4,509,534 A 4/1985 Tassin, Jr.
4,551,131 A 11/1985 Miles et al.
4,581,014 A 4/1986 Millerd et al.
4,608,996 A 9/1986 Brown
4,626,248 A 12/1986 Scheller
4,654,027 A 3/1987 Dragan et al.
4,657,027 A 4/1987 Paulsen
4,657,160 A 4/1987 Woods et al.
4,673,386 A 6/1987 Gordon
4,676,256 A 6/1987 Golden
4,679,571 A 7/1987 Frankel et al.
4,690,154 A 9/1987 Woodford et al.
4,699,612 A 10/1987 Hamacher
4,703,763 A 11/1987 McAlister et al.
4,705,497 A 11/1987 Shitaokoshi et al.
4,714,461 A 12/1987 Gabel
4,715,854 A 12/1987 Vaillancourt
4,772,273 A 9/1988 Alchas
4,820,287 A 4/1989 Leonard
4,838,855 A 6/1989 Lynn
4,865,583 A 9/1989 Tu
4,879,098 A 11/1989 Oberhardt et al.
4,886,072 A 12/1989 Percarpio et al.
4,890,627 A 1/1990 Haber et al.
4,904,240 A 2/1990 Hoover
4,936,315 A 6/1990 Lineback
4,980,297 A 12/1990 Haynes et al.
4,988,339 A 1/1991 Vadher
5,006,114 A 4/1991 Rogers et al.
5,009,847 A 4/1991 Solomons
5,027,827 A 7/1991 Cody et al.
5,032,116 A 7/1991 Peterson et al.
5,032,288 A 7/1991 Columbus et al.
5,035,688 A 7/1991 Inui
5,045,185 A 9/1991 Ohnaka et al.
5,052,403 A 10/1991 Haber et al.
5,054,498 A 10/1991 Melet
5,066,284 A 11/1991 Mersch et al.
5,084,034 A 1/1992 Zanotti
5,097,842 A 3/1992 Bonn
5,100,394 A 3/1992 Dudar et al.
5,108,927 A 4/1992 Dom
5,116,323 A 5/1992 Kreuzer et al.
5,122,129 A 6/1992 Olson et al.
5,126,054 A 6/1992 Matkovich
5,135,489 A 8/1992 Jepson et al.
5,147,329 A 9/1992 Brannon
5,208,160 A 5/1993 Kikyotani et al.
5,222,502 A 6/1993 Kurose
5,269,317 A 12/1993 Bennett
5,286,279 A 2/1994 Wu
5,330,464 A 7/1994 Mathias et al.
5,334,162 A 8/1994 Harris
5,354,537 A 10/1994 Moreno
5,360,011 A 11/1994 McCallister
5,372,143 A 12/1994 Bernes et al.

(56) References Cited

U.S. PATENT DOCUMENTS 5,395,339 A 3/1995 Talonn et al.
5,417,673 A 5/1995 Gordon
5,429,610 A 7/1995 Vaillancourt
5,431,811 A 7/1995 Tusini et al.
5,439,022 A 8/1995 Summers et al.
5,439,450 A 8/1995 Haedt
5,450,856 A 9/1995 Norris
5,451,321 A 9/1995 Matkovich
5,454,786 A 10/1995 Harris
5,466,228 A 11/1995 Evans
5,472,605 A 12/1995 Zuk, Jr.
5,485,854 A 1/1996 Hollister
5,507,299 A 4/1996 Roland
5,520,193 A 5/1996 Suzuki et al.
5,522,804 A 6/1996 Lynn
5,573,510 A 11/1996 Isaacson
5,573,951 A 11/1996 Gombrich et al.
5,575,777 A 11/1996 Cover et al.
5,577,513 A 11/1996 Van Vlasselaer
5,603,700 A 2/1997 Daneshvar
5,632,906 A 5/1997 Ishida et al.
5,634,893 A 6/1997 Rishton
5,649,912 A 7/1997 Peterson
5,658,271 A 8/1997 Loubser
5,685,846 A 11/1997 Michaels, Jr.
5,691,486 A 11/1997 Behringer et al.
5,749,857 A 5/1998 Cuppy
5,759,160 A 6/1998 Neese et al.
5,762,633 A 6/1998 Whisson
5,772,608 A 6/1998 Dhas
5,785,682 A 7/1998 Grabenkort
5,811,658 A 9/1998 Van Driel et al.
5,824,001 A 10/1998 Erskine
5,857,983 A 1/1999 Douglas et al.
5,865,803 A 2/1999 Major
5,865,812 A 2/1999 Correia
5,871,699 A 2/1999 Ruggeri
5,873,841 A 2/1999 Brannon
5,876,926 A 3/1999 Beecham
5,882,318 A 3/1999 Boyde
D410,081 S 5/1999 Sweeney et al.
5,911,705 A 6/1999 Howell
5,922,551 A 7/1999 Durbin et al.
RE36,273 E 8/1999 Brannon
5,947,932 A 9/1999 Desecki et al.
5,961,472 A 10/1999 Swendson et al.
5,971,956 A 10/1999 Epstein
5,980,830 A 11/1999 Savage et al.
6,001,307 A 12/1999 Naka et al.
6,010,633 A 1/2000 Zuk, Jr. et al.
6,013,037 A 1/2000 Brannon
6,016,712 A 1/2000 Warden et al.
6,050,957 A 4/2000 Desch
6,057,105 A 5/2000 Hoon et al.
6,074,366 A 6/2000 Rogers et al.
6,103,271 A 8/2000 Morrison et al.
6,106,509 A 8/2000 Loubser
6,126,643 A 10/2000 Vaillancouert
6,146,360 A 11/2000 Rogers et al.
6,159,164 A 12/2000 Neese et al.
6,171,493 B1 1/2001 Zia et al.
6,190,855 B1 2/2001 Herman et al.
6,210,909 B1 4/2001 Guirguis
6,224,561 B1 5/2001 Swendson et al.
6,254,581 B1 7/2001 Scott
6,296,020 B1 10/2001 McNeely et al.
6,299,131 B1 10/2001 Ryan
6,306,614 B1 10/2001 Romaschin et al.
6,325,975 B1 12/2001 Naka et al.
6,328,726 B1 12/2001 Ishida et al.
6,355,023 B1 3/2002 Roth et al.
6,364,847 B1 4/2002 Shulze et al.
6,364,890 B1 4/2002 Lum et al.
6,368,306 B1 4/2002 Koska
6,387,086 B2 5/2002 Mathias et al.
6,398,743 B1 6/2002 Halseth et al.
6,403,381 B1 6/2002 Mann et al.
6,416,496 B1 7/2002 Rogers et al.
6,440,725 B1 8/2002 Pourahmadi et al.
6,478,775 B1 11/2002 Galt et al.
6,482,188 B1 11/2002 Rogers et al.
6,506,182 B2 1/2003 Estabrook et al.
6,511,439 B1 1/2003 Tabata et al.
6,520,948 B1 2/2003 Mathias et al.
6,569,117 B1 5/2003 Ziv et al.
6,592,555 B1 7/2003 Wen-Pi
6,592,613 B1 7/2003 Ishida et al.
6,626,884 B1 9/2003 Dillon et al.
6,629,959 B2 10/2003 Kuracina et al.
6,638,252 B2 10/2003 Moulton et al.
6,638,263 B1 10/2003 Theeuwes et al.
6,648,835 B1 11/2003 Shemesh
6,664,893 B1 12/2003 Eveland et al.
6,665,385 B2 12/2003 Rogers et al.
6,692,479 B2 2/2004 Kraus et al.
6,695,004 B1 2/2004 Raybuck
6,712,963 B2 3/2004 Schick
6,716,187 B1 4/2004 Jorgensen et al.
6,716,396 B1 4/2004 Anderson et al.
6,733,433 B1 5/2004 Fell
6,736,783 B2 5/2004 Blake et al.
6,746,420 B1 6/2004 Prestidge et al.
6,772,513 B1 8/2004 Frye-Mason et al.
6,843,775 B2 1/2005 Hyun
6,860,871 B2 3/2005 Kuracina et al.
6,905,483 B2 6/2005 Newby et al.
6,913,580 B2 7/2005 Stone
6,945,948 B2 9/2005 Bainbridge et al.
6,957,107 B2 10/2005 Rogers et al.
6,979,323 B2 12/2005 Rogers et al.
7,002,468 B2 2/2006 Eveland et al.
7,044,941 B2 5/2006 Mathias et al.
7,052,603 B2 5/2006 Schick
7,055,401 B2 6/2006 Prybella et al.
7,087,047 B2 8/2006 Kraus et al.
7,130,396 B2 10/2006 Rogers et al.
7,141,097 B2 11/2006 Leahey
7,241,281 B2 7/2007 Coelho et al.
7,261,707 B2 8/2007 Frezza et al.
7,264,608 B2 9/2007 Bischof et al.
7,306,736 B2 12/2007 Collins et al.
7,314,452 B2 1/2008 Madonia
7,316,662 B2 1/2008 Delnevo et al.
7,335,188 B2 2/2008 Graf
7,351,228 B2 4/2008 Keane et al.
7,384,416 B2 6/2008 Goudaliez et al.
7,435,231 B2 10/2008 Mathias et al.
7,461,671 B2 12/2008 Ehwald et al.
7,479,131 B2 1/2009 Mathias et al.
7,544,324 B2 6/2009 Tung et al.
7,614,857 B2 11/2009 Fuechslin et al.
7,615,033 B2 11/2009 Leong
7,618,407 B2 11/2009 Demay et al.
7,648,491 B2 1/2010 Rogers
7,666,166 B1 2/2010 Emmert et al.
7,744,573 B2 6/2010 Gordon et al.
7,766,879 B2 8/2010 Tan et al.
7,780,794 B2 8/2010 Rogers et al.
7,896,817 B2 3/2011 Garrison
7,914,508 B2 3/2011 Engstrom
7,923,053 B2 4/2011 Kitching et al.
7,963,950 B2 6/2011 Madonia
7,985,302 B2 7/2011 Rogers et al.
8,070,725 B2 12/2011 Christensen
8,109,157 B2 2/2012 Kanayama et al.
RE43,283 E 3/2012 Ishida et al.
8,197,420 B2 6/2012 Patton
8,206,318 B2 6/2012 Uchiyama et al.
8,206,514 B2 6/2012 Rogers et al.
8,231,546 B2 7/2012 Patton
8,282,605 B2 10/2012 Tan et al.
8,287,499 B2 10/2012 Miyasaka
8,290,129 B2 10/2012 Rogers et al.
8,337,418 B2 12/2012 Patton

(56) References Cited

U.S. PATENT DOCUMENTS 8,349,254 B2 1/2013 Hoshino et al.
8,356,644 B2 1/2013 Chong et al.
8,377,040 B2 2/2013 Burkholz et al.
8,382,712 B2 2/2013 Kim
8,383,044 B2 2/2013 Davis et al.
8,412,300 B2 4/2013 Sonderegger
8,523,826 B2 9/2013 Layton, Jr.
8,535,241 B2 9/2013 Bullington et al.
8,540,663 B2 9/2013 Davey et al.
8,568,371 B2 10/2013 Siopes et al.
8,574,203 B2 11/2013 Stout et al.
8,603,009 B2 12/2013 Tan et al.
8,647,286 B2 2/2014 Patton
8,679,063 B2 3/2014 Stout et al.
8,747,779 B2 6/2014 Sprague et al.
8,772,046 B2 7/2014 Fraden et al.
8,795,198 B2 8/2014 Tan et al.
8,808,202 B2 8/2014 Brancazio
8,827,958 B2 9/2014 Bierman et al.
8,832,894 B2 9/2014 Rogers et al.
8,834,650 B2 9/2014 Rogers et al.
8,864,684 B2 10/2014 Bullington et al.
8,876,734 B2 11/2014 Patton
8,992,505 B2 3/2015 Thorne et al.
8,999,073 B2 4/2015 Rogers et al.
9,022,950 B2 5/2015 Bullington et al.
9,022,951 B2 5/2015 Bullington et al.
9,060,724 B2 6/2015 Bullington et al.
9,060,725 B2 6/2015 Bullington et al.
9,138,572 B2 9/2015 Zeytoonian et al.
9,149,576 B2 10/2015 Bullington et al.
9,155,495 B2 10/2015 Bullington et al.
9,204,864 B2 12/2015 Bullington et al.
9,205,198 B2 12/2015 Py
9,233,208 B2 1/2016 Tekeste
RE45,896 E 2/2016 Stout et al.
9,259,284 B2 2/2016 Rogers et al.
9,314,201 B2 4/2016 Burkholz et al.
9,320,459 B2 4/2016 Chin et al.
9,820,682 B2 11/2017 Rogers et al.
9,855,001 B2 1/2018 Patton
9,855,002 B2 1/2018 Patton
9,855,386 B2 1/2018 Close et al.
9,861,306 B2 1/2018 Patton
9,872,645 B2 1/2018 Patton
9,877,674 B2 1/2018 Holmes et al.
9,877,675 B2 1/2018 Baid
9,895,092 B2 2/2018 Burkholz
9,931,466 B2 4/2018 Bullington et al.
9,950,084 B2 4/2018 Bullington et al.
9,962,489 B2 5/2018 Hopkins
9,999,383 B2 6/2018 Bullington et al.
10,010,282 B2 7/2018 Rogers et al.
10,022,079 B2 7/2018 Hopkins
10,022,530 B2 7/2018 Tekeste
10,028,687 B2 7/2018 Patton
10,028,688 B2 7/2018 Patton
10,028,689 B2 7/2018 Patton
10,039,483 B2 8/2018 Bullington et al.
10,045,724 B2 8/2018 Patton
10,052,053 B2 8/2018 Patton
10,080,516 B2 9/2018 Ellis et al.
10,086,142 B2 10/2018 Tekeste
10,143,412 B2 12/2018 Rogers et al.
10,143,413 B2 12/2018 Garrett et al.
10,206,613 B2 2/2019 Bullington et al.
10,220,139 B2 3/2019 Bullington et al.
10,238,326 B2 3/2019 Gil et al.
10,251,590 B2 4/2019 Bullington et al.
10,265,007 B2 4/2019 Bullington et al.
10,292,633 B2 5/2019 Bullington et al.
10,299,713 B2 5/2019 Patton
10,369,285 B2 8/2019 Hopkins
10,433,779 B2 10/2019 Bullington et al.
10,463,792 B2 11/2019 Hopkins
10,596,315 B2 3/2020 Bullington et al.
10,624,977 B2 4/2020 Bullington et al.
10,736,554 B2 8/2020 Bullington et al.
10,744,315 B2 8/2020 Sanders
10,772,548 B2 9/2020 Bullington et al.
10,813,579 B2 10/2020 Baid
10,827,964 B2 11/2020 Rogers et al.
10,856,791 B2 12/2020 McHale et al.
10,881,343 B2 1/2021 Bullington et al.
10,888,262 B2 1/2021 Russ et al.
10,912,506 B2 2/2021 Bullington et al.
11,076,787 B2 8/2021 Bullington et al.
11,116,904 B2 9/2021 Hopkins
11,167,085 B2 11/2021 Hopkins
11,234,626 B2 2/2022 Bullington et al.
11,253,649 B2 2/2022 Hopkins
11,259,727 B2 3/2022 Bullington et al.
11,311,218 B2 4/2022 Bullington et al.
11,317,838 B2 5/2022 Bullington et al.
11,318,459 B2 5/2022 Shi et al.
11,395,611 B2 7/2022 Bullington et al.
11,395,612 B2 7/2022 Bullington et al.
11,419,531 B2 8/2022 Bullington et al.
11,529,081 B2 12/2022 Bullington et al.
11,589,786 B2 2/2023 Bullington et al.
11,607,159 B2 3/2023 Bullington et al.
11,653,863 B2 5/2023 Bullington et al.
11,660,030 B2 5/2023 Bullington et al.
11,737,693 B2 8/2023 Bullington et al.
11,786,155 B2 10/2023 Bullington et al.
11,789,017 B2 10/2023 Bullington et al.
11,819,329 B2 11/2023 Bullington et al.
11,857,321 B2 1/2024 Bullington et al.
11,890,452 B2 2/2024 Bullington et al.
11,903,709 B2 2/2024 Bullington et al.
11,903,710 B2 2/2024 Bullington et al.
11,998,332 B2 6/2024 Bullington et al.
12,083,234 B2 9/2024 Bullington et al.
12,133,968 B2 11/2024 Bullington et al.
12,138,052 B1 11/2024 Rogers et al.
12,150,763 B2 11/2024 Bullington et al.
12,186,080 B2 1/2025 Bullington et al.
12,193,816 B2 1/2025 Bullington et al.
12,290,363 B2 5/2025 Bullington et al.
12,471,815 B2 11/2025 Bullington et al.
12,471,816 B2 11/2025 Bullington et al.
12,478,300 B2 11/2025 Bullington et al.
12,478,301 B2 11/2025 Bullington et al.
12,502,109 B2 12/2025 Bullington et al.
12,551,150 B2 2/2026 Bullington et al.
2001/0031932 A1 10/2001 Blake et al.
2001/0039058 A1 11/2001 Iheme et al.
2002/0002349 A1 1/2002 Flaherty et al.
2002/0004647 A1 1/2002 Leong
2002/0107469 A1 8/2002 Bolan et al.
2002/0183651 A1 12/2002 Hyun
2002/0193751 A1 12/2002 Theeuwes et al.
2003/0013991 A1 1/2003 Stone
2003/0040708 A1 2/2003 Rogers et al.
2003/0055381 A1 3/2003 Wilkinson
2003/0069543 A1 4/2003 Carpenter et al.
2003/0105414 A1 6/2003 Leong
2003/0208151 A1 11/2003 Kraus et al.
2004/0000309 A1 1/2004 Alston
2004/0009542 A1 1/2004 Dumont et al.
2004/0010228 A1 1/2004 Swenson et al.
2004/0054283 A1 3/2004 Corey et al.
2004/0054333 A1 3/2004 Theeuwes et al.
2004/0073171 A1 4/2004 Rogers et al.
2004/0124389 A1 7/2004 Phillips
2004/0127816 A1 7/2004 Galvao
2004/0147855 A1 7/2004 Marsden
2005/0004524 A1 1/2005 Newby et al.
2005/0010136 A1 1/2005 Restelli et al.
2005/0054949 A1 3/2005 McKinnon et al.
2005/0082218 A1 4/2005 Verri et al.
2005/0148993 A1 7/2005 Mathias et al.
2005/0154368 A1 7/2005 Lim et al.
2005/0161112 A1 7/2005 Ehwald et al.

(56) References Cited

U.S. PATENT DOCUMENTS

2005/0199077 A1 9/2005 Prybella et al.
2005/0240161 A1 10/2005 Crawford
2005/0245885 A1 11/2005 Brown
2005/0273019 A1 12/2005 Conway et al.
2005/0277848 A1 12/2005 Graf
2005/0281713 A1 12/2005 Hampsch et al.
2006/0009713 A1 1/2006 Flaherty
2006/0018790 A1 1/2006 Naka et al.
2006/0111667 A1 5/2006 Matsuura et al.
2006/0155212 A1 7/2006 Madonia
2006/0251622 A1 11/2006 Suzuki et al.
2006/0287639 A1 12/2006 Sharp
2007/0083162 A1 4/2007 O'Reagan et al.
2007/0088279 A1 4/2007 Shue et al.
2007/0100250 A1 5/2007 Kline
2007/0119508 A1 5/2007 West et al.
2007/0172389 A1 7/2007 Wilding et al.
2007/0191716 A1 8/2007 Goldberger et al.
2007/0287948 A1 12/2007 Sakiewicz
2008/0086085 A1 4/2008 Brown
2008/0108954 A1 5/2008 Mathias et al.
2008/0114304 A1 5/2008 Nalesso et al.
2008/0145933 A1 6/2008 Patton
2008/0167577 A1 7/2008 Weilbacher et al.
2008/0185056 A1 8/2008 Diodati et al.
2008/0200837 A1 8/2008 Frazier et al.
2008/0254471 A1 10/2008 Bordano
2008/0255523 A1 10/2008 Grinberg
2008/0312576 A1 12/2008 McKinnon et al.
2008/0319346 A1 12/2008 Crawford et al.
2009/0050213 A1 2/2009 Biddell et al.
2009/0076441 A1 3/2009 Sebban
2009/0173685 A1 7/2009 Imai et al.
2009/0177117 A1 7/2009 Amano et al.
2009/0192447 A1 7/2009 Andersen et al.
2009/0215159 A1 8/2009 Kirby
2009/0227896 A1 9/2009 Tan et al.
2009/0301317 A1 12/2009 Andrews
2009/0306601 A1 12/2009 Shaw et al.
2010/0010372 A1 1/2010 Brown et al.
2010/0042048 A1 2/2010 Christensen
2010/0057004 A1 3/2010 Christensen et al.
2010/0094171 A1 4/2010 Conway et al.
2010/0152681 A1 6/2010 Mathias
2010/0185134 A1 7/2010 Houwen et al.
2010/0234768 A1 9/2010 Uchiyama et al.
2010/0240964 A1 9/2010 Sterling et al.
2010/0252118 A1 10/2010 Fraden et al.
2010/0255589 A1 10/2010 Saiki et al.
2010/0268118 A1 10/2010 Schweiger
2010/0286513 A1 11/2010 Pollard et al.
2010/0298671 A1 11/2010 Asakura et al.
2010/0306938 A1 12/2010 Rogers et al.
2011/0009717 A1 1/2011 Davis et al.
2011/0046602 A1 2/2011 Grimm et al.
2011/0092856 A1 4/2011 Freeman et al.
2011/0125058 A1 5/2011 Levinson et al.
2011/0178427 A1 7/2011 Tan et al.
2011/0198221 A1* 8/2011 Angelescu ............ A61B 5/061 422/68.1
2011/0232020 A1 9/2011 Rogers et al.
2011/0288441 A1 11/2011 Taguchi
2011/0306856 A1 12/2011 Rule et al.
2011/0306899 A1 12/2011 Brown et al.
2011/0313318 A1 12/2011 Rule et al.
2011/0319859 A1 12/2011 Zeytoonian et al.
2012/0004619 A1 1/2012 Stephens et al.
2012/0016266 A1 1/2012 Burkholz
2012/0017999 A1 1/2012 Velschow
2012/0022404 A1 1/2012 Fojtik
2012/0029494 A1 2/2012 Wittenberger et al.
2012/0035540 A1 2/2012 Ferren et al.
2012/0095367 A1 4/2012 Patton
2012/0123297 A1 5/2012 Brancazio
2012/0215131 A1 8/2012 Patton
2012/0216359 A1 8/2012 Rogers et al.
2012/0216360 A1 8/2012 Rogers et al.
2012/0226239 A1 9/2012 Green
2012/0245042 A1 9/2012 Liu et al.
2012/0265099 A1 10/2012 Goodnow, II et al.
2012/0265128 A1 10/2012 Kolln
2012/0277697 A1 11/2012 Haghgooie et al.
2012/0323142 A1 12/2012 Allen et al.
2013/0023792 A1 1/2013 Markey et al.
2013/0079604 A1 3/2013 Patton
2013/0085514 A1 4/2013 Lee et al.
2013/0116599 A1 5/2013 Bullington et al.
2013/0158506 A1 6/2013 Harris et al.
2013/0289420 A1 10/2013 Pfeiffer et al.
2013/0295602 A1 11/2013 Fowler et al.
2013/0317391 A1 11/2013 Bullington et al.
2013/0335195 A1 12/2013 Rogers
2014/0008366 A1 1/2014 Genosar
2014/0039348 A1 2/2014 Bullington et al.
2014/0051062 A1 2/2014 Vanapalli et al.
2014/0066880 A1 3/2014 Prince et al.
2014/0081172 A1 3/2014 Patton
2014/0107564 A1 4/2014 Bullington et al.
2014/0124542 A1 5/2014 Kojima et al.
2014/0128775 A1 5/2014 Andreae et al.
2014/0150832 A1 6/2014 Rogers et al.
2014/0155781 A1 6/2014 Bullington et al.
2014/0155782 A1 6/2014 Bullington et al.
2014/0163419 A1 6/2014 Bullington et al.
2014/0188002 A1 7/2014 Close et al.
2014/0208978 A1 7/2014 Sunder et al.
2014/0221873 A1 8/2014 Hayakawa et al.
2014/0257249 A1 9/2014 Witt
2014/0261558 A1 9/2014 Rogers
2014/0261581 A1 9/2014 Rogers et al.
2014/0276039 A1 9/2014 Cowan et al.
2014/0305196 A1 10/2014 Ellis et al.
2014/0336536 A1 11/2014 Brancazio
2015/0000061 A1 1/2015 Rogers et al.
2015/0011847 A1 1/2015 Hayden
2015/0011910 A1 1/2015 Bullington et al.
2015/0011911 A1 1/2015 Bullington et al.
2015/0018715 A1 1/2015 Walterspiel
2015/0025454 A1 1/2015 Wetzel et al.
2015/0025455 A1 1/2015 Shetty et al.
2015/0025456 A1 1/2015 Shetty et al.
2015/0073304 A1 3/2015 Millerd
2015/0073348 A1 3/2015 Bullington et al.
2015/0094615 A1 4/2015 Patton
2015/0099996 A1 4/2015 Bullington et al.
2015/0151298 A1 6/2015 Hobbs et al.
2015/0257691 A1 9/2015 Bullington et al.
2015/0314105 A1 11/2015 Gasparyan et al.
2015/0342510 A1 12/2015 Bullington et al.
2015/0351678 A1 12/2015 Bullington et al.
2015/0351679 A1 12/2015 Bullington et al.
2015/0359473 A1 12/2015 Garrett et al.
2015/0367069 A1 12/2015 Bullington et al.
2016/0008579 A1 1/2016 Burkholz et al.
2016/0038068 A1 2/2016 Chickering, III et al.
2016/0038684 A1 2/2016 Lum et al.
2016/0081606 A1 3/2016 Russ et al.
2016/0089070 A1 3/2016 Russ et al.
2016/0113560 A1 4/2016 Bullington et al.
2016/0135724 A1 5/2016 Bullington et al.
2016/0174888 A1 6/2016 Berthier et al.
2016/0174948 A1 6/2016 Kato et al.
2016/0213294 A1 7/2016 Patton
2016/0257586 A1 9/2016 Shaamsundarr
2016/0361006 A1 12/2016 Bullington et al.
2016/0367177 A1 12/2016 Edelhauser et al.
2017/0020427 A1 1/2017 Rogers et al.
2017/0020428 A1 1/2017 Rogers et al.
2017/0059552 A1 3/2017 Champton et al.
2017/0065733 A1 3/2017 Bullington et al.
2017/0071519 A1 3/2017 Gelfand et al.
2017/0143447 A1 5/2017 Rogers et al.
2017/0150913 A1 6/2017 Patton
2017/0153165 A1 6/2017 Nwadigo

(56) References Cited

U.S. PATENT DOCUMENTS

2017/0156654 A1 6/2017 Patton
2017/0172482 A1 6/2017 Patton
2017/0181683 A1 6/2017 Patton
2017/0227536 A1 8/2017 Matsuura
2017/0276679 A1 9/2017 Chapman et al.
2017/0327867 A1 11/2017 Dohale et al.
2017/0361019 A1 12/2017 Hopkins
2018/0078186 A1 3/2018 Patton
2018/0085042 A1 3/2018 Patton
2018/0092582 A1 4/2018 Patton
2018/0092583 A1 4/2018 Patton
2018/0092584 A1 4/2018 Bullington et al.
2018/0093077 A1 4/2018 Harding et al.
2018/0098723 A1 4/2018 Patton
2018/0116577 A1 5/2018 Bullington et al.
2018/0160958 A1 6/2018 Baid
2018/0177445 A1* 6/2018 Rogers ................. A61B 5/1545
2018/0177943 A1 6/2018 Bullington et al.
2018/0207300 A1 7/2018 Bullington et al.
2018/0242890 A1 8/2018 Chickering, III et al.
2018/0271425 A1 9/2018 Rogers et al.
2018/0289894 A1 10/2018 Hopkins
2018/0321270 A1 11/2018 Iwashita et al.
2018/0353117 A1 12/2018 Bullington et al.
2019/0000367 A1* 1/2019 Lundquist ........ A61B 5/150389
2019/0030293 A1 1/2019 Rogers et al.
2019/0049442 A1 2/2019 Guirguis
2019/0076074 A1 3/2019 Bullington et al.
2019/0150818 A1 5/2019 Bullington et al.
2019/0151536 A1 5/2019 Bullington et al.
2019/0159711 A1 5/2019 Rogers et al.
2019/0175085 A1 6/2019 Bullington et al.
2019/0175087 A1 6/2019 Bullington et al.
2019/0209066 A1 7/2019 Bullington et al.
2019/0365303 A1 12/2019 Bullington et al.
2019/0374145 A1 12/2019 Breindel et al.
2020/0060595 A1 2/2020 Bullington et al.
2020/0060596 A1 2/2020 Patton
2020/0197925 A1 6/2020 Ivosevic et al.
2020/0214611 A1 7/2020 Ivosevic
2020/0215211 A1 7/2020 Bullington et al.
2020/0253524 A1 8/2020 Bullington et al.
2020/0281514 A1 9/2020 Rogers et al.
2020/0289039 A1 9/2020 Bullington et al.
2020/0305780 A1 10/2020 Rogers et al.
2020/0352497 A1 11/2020 Brewer et al.
2020/0359951 A1 11/2020 Bullington et al.
2021/0008280 A1 1/2021 Bullington et al.
2021/0085230 A1 3/2021 Brewer et al.
2021/0169387 A1 6/2021 Bullington et al.
2021/0178389 A1 6/2021 Bullington et al.
2021/0186392 A1 6/2021 Bullington et al.
2021/0290123 A1 9/2021 Sawyer
2021/0345919 A1 11/2021 Brewer et al.
2021/0345920 A1 11/2021 Brewer et al.
2021/0345921 A1 11/2021 Brewer et al.
2021/0345922 A1 11/2021 Brewer et al.
2021/0353193 A1 11/2021 Bullington et al.
2021/0353194 A1 11/2021 Bullington et al.
2021/0361206 A1 11/2021 Bullington et al.
2021/0361207 A1 11/2021 Rogers et al.
2022/0023539 A1 1/2022 Hopkins
2022/0071533 A1 3/2022 Bullington et al.
2022/0079482 A1 3/2022 Bullington et al.
2022/0151525 A1 5/2022 Bullington et al.
2022/0151527 A1 5/2022 Bullington et al.
2022/0175284 A1 6/2022 Bullington et al.
2022/0183600 A1 6/2022 Bullington et al.
2022/0218248 A1 7/2022 Bullington et al.
2022/0218249 A1 7/2022 Bullington et al.
2022/0218250 A1 7/2022 Bullington et al.
2022/0304600 A1 9/2022 Hammer
2022/0304601 A1 9/2022 Bullington et al.
2022/0304664 A1 9/2022 Hammer
2022/0361786 A1 11/2022 Bullington et al.
2022/0369970 A1 11/2022 Bullington et al.
2022/0369971 A1 11/2022 Bullington et al.
2022/0369972 A1 11/2022 Bullington et al.
2023/0109255 A1 4/2023 Rogers et al.
2023/0172502 A1 6/2023 Bullington et al.
2023/0190157 A1 6/2023 Bullington et al.
2023/0240571 A1 8/2023 Bullington et al.
2023/0248281 A1 8/2023 Bullington et al.
2023/0363674 A1 11/2023 Bullington et al.
2023/0417746 A1 12/2023 Bullington et al.
2024/0008780 A1 1/2024 Bullington et al.
2024/0041369 A1 2/2024 Bullington et al.
2024/0041370 A1 2/2024 Bullington et al.
2024/0057908 A1 2/2024 Bullington et al.
2024/0065590 A1 2/2024 Bullington et al.
2024/0131258 A1 4/2024 Bullington et al.
2024/0138734 A1 5/2024 Bullington et al.
2024/0164670 A1 5/2024 Patton
2024/0306963 A1 9/2024 Bullington et al.
2024/0306964 A1 9/2024 Bullington et al.
2024/0315620 A1 9/2024 Bullington et al.
2024/0315621 A1 9/2024 Bullington et al.
2024/0315622 A1 9/2024 Bullington et al.
2024/0315623 A1 9/2024 Bullington et al.
2024/0315624 A1 9/2024 Bullington et al.
2025/0082235 A1 3/2025 Bullington et al.
2025/0120628 A1 4/2025 Bullington et al.
2025/0235133 A1 7/2025 Bullington et al.
2025/0235613 A1 7/2025 Bullington
2025/0275697 A1 9/2025 Bullington et al.
2026/0033759 A1 2/2026 Bullington et al.

FOREIGN PATENT DOCUMENTS

AU 736156 B2 7/2001
BR 112012025546 A2 6/2016
CA 1264275 A 1/1990
CN 86103696 A 1/1987
CN 2115767 U 9/1992
CN 1713928 A 12/2005
CN 1784186 A 6/2006
CN 1901955 A 1/2007
CN 2907683 Y 6/2007
CN 1325126 C 7/2007
CN 101060871 A 10/2007
CN 101309641 A 11/2008
CN 101352357 A 1/2009
CN 101437450 A 5/2009
CN 101564301 A 10/2009
CN 101631498 A 1/2010
CN 101676001 A 3/2010
CN 101785676 A 7/2010
CN 101801445 A 8/2010
CN 201617841 U 11/2010
CN 102421362 A 4/2012
CN 102548524 A 7/2012
CN 102811754 A 12/2012
CN 102971040 A 3/2013
CN 103027727 A 4/2013
CN 101626803 B 8/2013
CN 103477201 A 12/2013
CN 103619386 A 3/2014
CN 104902817 A 9/2015
CN 104955392 A 9/2015
CN 104971390 A 10/2015
CN 104981203 A 10/2015
CN 105090005 A 11/2015
CN 105612346 A 5/2016
CN 105813669 A 7/2016
CN 107736901 A 2/2018
CN 209916854 U 1/2020
DE 7 203 008 U 5/1972
DE 2 541 494 A1 3/1977
DE 2203858 B2 10/1977
DE 2946660 A1 5/1981
DE 3403957 A1 8/1985
DE 4026732 A1 2/1992
DE 299 13 417 U1 12/2000
DE 100 38 026 A1 2/2001

(56) References Cited

FOREIGN PATENT DOCUMENTS

| | | | |
|---|---|---|---|
| DE | 101 34 913 | A1 | 2/2003 |
| DE | 101 34 913 | C2 | 2/2003 |
| DE | 102 43 129 | A1 | 4/2004 |
| DE | 69632870 | T2 | 7/2005 |
| DE | 102009057792 | B4 | 8/2016 |
| EP | 0181957 | A1 | 5/1986 |
| EP | 0 207 304 | A1 | 1/1987 |
| EP | 0 448 795 | | 10/1991 |
| EP | 0208053 | B1 | 12/1991 |
| EP | 0329786 | B1 | 1/1993 |
| EP | 0486059 | B1 | 1/1997 |
| EP | 1144026 | B1 | 7/2004 |
| EP | 1505159 | B1 | 5/2008 |
| EP | 1 980 204 | | 10/2008 |
| EP | 2254472 | A2 | 12/2010 |
| EP | 1381438 | B1 | 5/2012 |
| EP | 2254472 | B1 | 5/2016 |
| EP | 1487369 | B1 | 5/2017 |
| EP | 2986218 | B1 | 12/2017 |
| EP | 2178585 | B1 | 4/2021 |
| ES | 2564496 | T3 | 3/2016 |
| FR | 2 110 516 | A5 | 6/1972 |
| FR | 2691364 | B1 | 8/1999 |
| FR | 2833175 | B1 | 5/2004 |
| FR | 2851167 | B1 | 10/2005 |
| GB | 1506449 | A | 4/1978 |
| GB | 1562686 | A | 3/1980 |
| IE | 904353 | A1 | 10/1991 |
| IL | 128709 | A | 9/2004 |
| JP | S48-046180 | A | 7/1973 |
| JP | S53-097289 | A | 8/1978 |
| JP | S56109643 | A | 8/1981 |
| JP | S57-089869 | A | 6/1982 |
| JP | S64-58241 | A | 3/1989 |
| JP | H0363570 | A | 3/1991 |
| JP | H06500403 | A | 1/1994 |
| JP | H07-16219 | A | 1/1995 |
| JP | H0910302 | A | 1/1997 |
| JP | H0951947 | A | 2/1997 |
| JP | H09229828 | A | 9/1997 |
| JP | H10153531 | A | 6/1998 |
| JP | H10211274 | A | 8/1998 |
| JP | H1156821 | A | 3/1999 |
| JP | H1176397 | A | 3/1999 |
| JP | H11197236 | A | 7/1999 |
| JP | 2001159630 | A | 6/2001 |
| JP | 2001161668 | A | 6/2001 |
| JP | 2001276181 | A | 10/2001 |
| JP | 3231086 | B2 | 11/2001 |
| JP | 2002-116201 | A | 4/2002 |
| JP | 2002272710 | A | 9/2002 |
| JP | 2002528159 | A | 9/2002 |
| JP | 2003126068 | A | 5/2003 |
| JP | 2005-237617 | A | 9/2005 |
| JP | 2006026327 | A | 2/2006 |
| JP | 3813974 | B2 | 8/2006 |
| JP | 2007175534 | A | 7/2007 |
| JP | 2008-149076 | A | 7/2008 |
| JP | 2008206734 | A | 9/2008 |
| JP | 2009525819 | A | 7/2009 |
| JP | 2009536554 | A | 10/2009 |
| JP | 4382322 | B2 | 12/2009 |
| JP | 2010514501 | A | 5/2010 |
| JP | 2010524505 | A | 7/2010 |
| JP | 2010-189415 | | 9/2010 |
| JP | 4573538 | B2 | 11/2010 |
| JP | 2010536014 | A | 11/2010 |
| JP | 2011512987 | A | 4/2011 |
| JP | 4861649 | B2 | 1/2012 |
| JP | 4869910 | B2 | 2/2012 |
| JP | 5344252 | B2 | 11/2013 |
| JP | 5620541 | B2 | 11/2014 |
| JP | 2015014552 | A | 1/2015 |
| JP | 2015519145 | A | 7/2015 |
| JP | 2015215355 | A | 12/2015 |
| JP | 2016500278 | A | 1/2016 |
| JP | 2016520827 | A | 7/2016 |
| JP | 2016523591 | A | 8/2016 |
| JP | 5997760 | B2 | 9/2016 |
| JP | 2016527939 | A | 9/2016 |
| JP | 6194415 | B2 | 9/2017 |
| JP | 2018110967 | A | 7/2018 |
| JP | 2018525191 | A | 9/2018 |
| JP | 2020513906 | A | 5/2020 |
| JP | 7204742 | B2 | 1/2023 |
| KR | 20120030087 | A | 3/2012 |
| KR | 101134279 | B1 | 4/2012 |
| KR | 20160088853 | A | 7/2016 |
| TW | 200528066 | A | 9/2005 |
| WO | WO 1986/005568 | | 9/1986 |
| WO | WO 1990/004351 | | 5/1990 |
| WO | WO-8403213 | A1 | 10/1990 |
| WO | WO 1991/018632 | | 12/1991 |
| WO | WO 1992/016144 | | 10/1992 |
| WO | WO-9407415 | A1 | 4/1994 |
| WO | WO-9412093 | A1 | 6/1994 |
| WO | WO-9415665 | A1 | 7/1994 |
| WO | WO-9511712 | A1 | 5/1995 |
| WO | WO 1995/016395 | | 6/1995 |
| WO | WO-9521639 | A1 | 8/1995 |
| WO | WO-9524176 | A1 | 9/1995 |
| WO | WO-9621853 | A1 | 7/1996 |
| WO | WO 1997/018845 | | 5/1997 |
| WO | WO-1997045714 | A1 | 12/1997 |
| WO | WO-1998034532 | A1 | 8/1998 |
| WO | WO 1998/046136 | | 10/1998 |
| WO | WO 1999/013925 | | 3/1999 |
| WO | WO-9929232 | A1 | 6/1999 |
| WO | WO 1999/048425 | | 9/1999 |
| WO | WO 1999/055232 | | 11/1999 |
| WO | WO 2000/024313 | | 5/2000 |
| WO | WO 2000/040291 | | 7/2000 |
| WO | WO 2000/041624 | | 7/2000 |
| WO | WO 2001/008546 | | 2/2001 |
| WO | WO 2001/091829 | | 12/2001 |
| WO | WO-2002028457 | A1 | 4/2002 |
| WO | WO-0245813 | A1 | 6/2002 |
| WO | WO 2002/051520 | | 7/2002 |
| WO | WO 2003/008012 | | 1/2003 |
| WO | WO-03041767 | A1 | 5/2003 |
| WO | WO 2003/047660 | | 6/2003 |
| WO | WO 2003/078964 | | 9/2003 |
| WO | WO-03085395 | A1 | 10/2003 |
| WO | WO-2003092573 | A2 | 11/2003 |
| WO | WO-2004082467 | A2 | 9/2004 |
| WO | WO-2004103565 | A2 | 12/2004 |
| WO | WO 2005/068011 | | 7/2005 |
| WO | WO 2006/031500 | | 3/2006 |
| WO | WO-2006124634 | A1 | 11/2006 |
| WO | WO 2007/033319 | | 3/2007 |
| WO | WO-2008028165 | A2 | 3/2008 |
| WO | WO-2008047699 | A1 | 4/2008 |
| WO | WO-2008077047 | A2 | 6/2008 |
| WO | WO 2008/101025 | | 8/2008 |
| WO | WO-2008157511 | A1 | 12/2008 |
| WO | WO-2009094345 | A1 | 7/2009 |
| WO | WO-2009113999 | A2 | 9/2009 |
| WO | WO-2010087216 | A1 | 8/2010 |
| WO | WO 2011/030282 | | 3/2011 |
| WO | WO-2011050110 | A1 | 4/2011 |
| WO | WO 2011/069145 | | 6/2011 |
| WO | WO-2011114413 | A1 | 9/2011 |
| WO | WO-2011123685 | A2 | 10/2011 |
| WO | WO-2011162772 | A1 | 12/2011 |
| WO | WO 2012/012127 | | 1/2012 |
| WO | WO-2012114105 | A1 | 8/2012 |
| WO | WO-2013181352 | A1 | 12/2013 |
| WO | WO-2014022275 | A1 | 2/2014 |
| WO | WO-2014022750 | A1 | 2/2014 |
| WO | WO-2014058945 | A1 | 4/2014 |
| WO | WO-2014085800 | A1 | 6/2014 |
| WO | WO-2014089186 | A1 | 6/2014 |
| WO | WO-2014099266 | A2 | 6/2014 |
| WO | WO-2015091818 | A1 | 6/2015 |

(56) References Cited

FOREIGN PATENT DOCUMENTS

| | | | |
|---|---|---|---|
| WO | WO-2016027782 | A1 | 2/2016 |
| WO | WO 2016/054252 | | 4/2016 |
| WO | WO-2016201406 | A1 | 12/2016 |
| WO | WO 2017/019552 | | 2/2017 |
| WO | WO 2017/041087 | | 3/2017 |
| WO | WO 2017/133953 | | 8/2017 |
| WO | WO-2017218840 | A1 | 12/2017 |
| WO | WO-2017218848 | A1 | 12/2017 |
| WO | WO-2018125929 | A1 | 7/2018 |
| WO | WO-2018227191 | A1 | 12/2018 |
| WO | WO-2019055487 | A1 | 3/2019 |
| WO | WO-2019113505 | A1 | 6/2019 |
| WO | WO 2019/232196 | | 12/2019 |
| WO | WO-2020163744 | A1 | 8/2020 |
| WO | WO-2020185914 | A1 | 9/2020 |
| WO | WO 2020/227701 | | 11/2020 |
| WO | WO-2021119487 | A1 | 6/2021 |
| WO | WO-2022203747 | A1 | 9/2022 |

OTHER PUBLICATIONS

Office Action for U.S. Appl. No. 11/955,635, dated Dec. 3, 2010, 11 pages.
Office Action for U.S. Appl. No. 13/335,241, dated Apr. 20, 2012, 12 pages.
Office Action for U.S. Appl. No. 13/458,508, dated Jul. 24, 2012, 13 pages.
Office Action for U.S. Appl. No. 13/675,295, dated May 23, 2013, 15 pages.
Office Action for U.S. Appl. No. 14/089,267, dated Jun. 19, 2014, 13 pages.
Office Action for U.S. Appl. No. 14/498,102, dated Oct. 17, 2017, 20 pages.
Office Action for U.S. Appl. No. 14/498,102, dated Sep. 24, 2018, 18 pages.
Office Action for U.S. Appl. No. 15/088,842, dated Nov. 23, 2016, 20 pages.
Office Action for U.S. Appl. No. 15/432,310, dated Apr. 12, 2017, 14 pages.
Office Action for U.S. Appl. No. 15/435,684, dated Jun. 12, 2017, 19 pages.
Office Action for U.S. Appl. No. 15/448,891, dated Jun. 16, 2017, 25 pages.
Office Action for U.S. Appl. No. 15/457,082, dated Jun. 15, 2017, 22 pages.
Office Action for U.S. Appl. No. 15/829,015, dated Feb. 6, 2018, 24 pages.
Office Action for U.S. Appl. No. 15/829,018, dated Feb. 16, 2018, 13 pages.
Office Action for U.S. Appl. No. 15/829,023, dated Feb. 7, 2018, 25 pages.
Office Action for U.S. Appl. No. 15/832,055, dated Feb. 8, 2018, 21 pages.
Office Action for U.S. Appl. No. 15/832,087, dated Feb. 7, 2018, 24 pages.
Office Action for U.S. Appl. No. 13/954,528, dated Mar. 17, 2014, 10 pages.
Office Action for U.S. Appl. No. 15/832,091, dated Feb. 22, 2018, 16 pages.
Office Action for U.S. Appl. No. 16/299,962, dated May 2, 2019, 14 pages.
Office Action for U.S. Appl. No. 16/299,962, dated Dec. 26, 2019, 14 pages.
Office Action for U.S. Appl. No. 16/299,962, dated Dec. 9, 2020, 15 pages.
Office Action for U.S. Appl. No. 16/299,962, dated Jun. 15, 2021, 17 pages.
Office Action for U.S. Appl. No. 14/493,796, dated Jan. 27, 2015, 7 pages.
Office Action for U.S. Appl. No. 14/494,208, dated Jan. 27, 2015, 7 pages.
Office Action for U.S. Appl. No. 14/662,676, dated Sep. 5, 2018, 25 pages.
Office Action for U.S. Appl. No. 14/712,437 dated Oct. 25, 2018, 20 pages.
Office Action for U.S. Appl. No. 15/854,273, dated Sep. 7, 2018, 15 pages.
Office Action for U.S. Appl. No. 15/854,273, dated Mar. 15, 2019, 19 pages.
Office Action for U.S. Appl. No. 15/854,273, dated Jan. 13, 2020, 13 pages.
Office Action for U.S. Appl. No. 16/376,745, dated May 14, 2021, 13 pages.
Office Action for U.S. Appl. No. 14/096,826, dated Jul. 26, 2017, 12 pages.
Office Action for U.S. Appl. No. 14/096,826, dated Mar. 8, 2018, 14 pages.
Office Action for U.S. Appl. No. 14/728,318, dated May 19, 2017, 26 pages.
Office Action for U.S. Appl. No. 14/728,318, dated Jan. 8, 2018, 36 pages.
Office Action for U.S. Appl. No. 14/728,318, dated Dec. 20, 2018, 26 pages.
Office Action for U.S. Appl. No. 16/274,835, dated Feb. 12, 2021, 17 pages.
Office Action for U.S. Appl. No. 14/049,326, dated Apr. 24, 2015, 10 pages.
Office Action for U.S. Appl. No. 14/838,794, dated Aug. 3, 2017, 8 pages.
Office Action for U.S. Appl. No. 16/255,055, dated Mar. 18, 2019, 16 pages.
Office Action for U.S. Appl. No. 13/952,964, dated Mar. 20, 2015, 11 pages.
Office Action for U.S. Appl. No. 14/926,784, dated May 25, 2018, 15 pages.
Office Action for U.S. Appl. No. 14/926,784, dated Jan. 15, 2019, 15 pages.
Office Action for U.S. Appl. No. 14/926,784, dated Jan. 21, 2020, 17 pages.
Office Action for U.S. Appl. No. 14/264,481, dated Jul. 1, 2015, 13 pages.
Office Action for U.S. Appl. No. 14/264,481, dated Feb. 26, 2016, 10 pages.
Office Action for U.S. Appl. No. 14/264,481, dated Jul. 14, 2016, 9 pages.
Office Action for U.S. Appl. No. 14/264,481, dated Oct. 21, 2016, 10 pages.
Office Action for U.S. Appl. No. 14/264,481, dated Apr. 13, 2017, 14 pages.
Office Action for U.S. Appl. No. 14/264,481, dated Sep. 7, 2017, 12 pages.
Office Action for U.S. Appl. No. 14/880,397, dated Apr. 17, 2018, 6 pages.
Office Action for U.S. Appl. No. 14/880,397, dated Sep. 24, 2018, 5 pages.
Office Action for U.S. Appl. No. 16/255,058, dated Mar. 30, 2021, 16 pages.
Office Action for U.S. Appl. No. 17/388,971, dated Nov. 23, 2021, 19 pages.
Office Action for U.S. Appl. No. 17/388,979, dated Dec. 8, 2021, 21 pages.
Office Action for U.S. Appl. No. 15/180,454, dated Jul. 25, 2019, 27 pages.
Office Action for U.S. Appl. No. 15/180,454, dated Apr. 1, 2020, 28 pages.
Office Action for U.S. Appl. No. 15/180,454, dated Jan. 21, 2021, 24 pages.
Office Action for U.S. Appl. No. 15/925,159, dated Nov. 26, 2018, 11 pages.
Office Action for U.S. Appl. No. 15/925,159, dated May 14, 2019, 15 pages.

(56) References Cited

OTHER PUBLICATIONS

Office Action for U.S. Appl. No. 16/004,955, dated Feb. 16, 2021, 28 pages.
Office Action for U.S. Appl. No. 16/129,066, dated Sep. 3, 2020, 13 pages.
Office Action for U.S. Appl. No. 16/213,005, dated Feb. 3, 2021, 15 pages.
Office Action for U.S. Appl. No. 16/426,380, dated Oct. 30, 2020, 29 pages.
Office Action for U.S. Appl. No. 16/426,380, dated May 7, 2021, 28 pages.
International Search Report and Written Opinion for International Application No. PCT/US2007/087951, dated May 16, 2008, 8 pages.
Examination Report for United Kingdom Application No. GB1805101.1, dated May 25, 2018, 8 pages.
International Search Report and Written Opinion for International Application No. PCT/US2013/071491, dated Aug. 5, 2014, 9 pages.
Notification of the First Office Action for Chinese Application No. 201380040468.7, dated Jun. 30, 2016, 9 pages.
Supplementary European Search Report for EP Application No. 13797732.8, dated Dec. 7, 2015, 5 pages.
International Search Report and Written Opinion for International Application No. PCT/US2013/043289, dated Oct. 24, 2013, 15 pages.
Notification of the First Office Action for Chinese Application No. 201711078173.5, dated Feb. 3, 2020, 14 pages.
Notice of Reasons for Rejection for Japanese Application No. 2020-075727, dated Jul. 21, 2021, with English translation, 37 pages.
Extended European Search Report for European Application No. 21167069.0, dated Nov. 10, 2021, 9 pages.
Notification of the First Office Action for Chinese Application No. 201380072185.0, dated Sep. 28, 2016, 17 pages.
Supplementary European Search Report for EP Application No. 13860741.1, dated Jun. 7, 2016, 5 pages.
Extended European Search Report for EP Application No. 17204012.3, dated Feb. 14, 2018, 7 pages.
International Search Report and Written Opinion for International Application No. PCT/US2013/073080, dated Feb. 18, 2014, 14 pages.
Notice of Reasons for Rejection for Japanese Application No. 2015-545813, dated Jul. 4, 2017, 14 pages.
Notice of Reasons for Rejection for Japanese Application No. 2018-086721, dated Mar. 15, 2019, 6 pages.
Notice of Reasons for Rejection for Japanese Application No. 2019-230734, dated Jan. 22, 2021, 9 pages.
Supplementary European Search Report for EP Application No. 13845555.5, dated Jul. 12, 2016, 9 pages.
Extended European Search Report for EP Application No. 17206745.6, dated Feb. 19, 2018, 8 pages.
Extended European Search Report for European Application No. 21167625.9, dated Oct. 8, 2021, 7 pages.
International Search Report and Written Opinion for International Application No. PCT/US2013/063975, dated Mar. 20, 2014, 16 pages.
International Search Report and Written Opinion for International Application No. PCT/US2013/052493, dated Nov. 27, 2013, 7 pages.
Notification of the First Office Action for Chinese Application No. 201380071681.4, dated Aug. 16, 2016, 9 pages.
Notification of the Second Office Action for Chinese Application No. 201380071681.4, dated Jun. 28, 2017, 9 pages.
Extended European Search Report for EP Application No. 13859067.4, dated Jun. 7, 2016, 4 pages.
Extended European Search Report for EP Application No. 13859067.4, dated Jan. 27, 2017, 4 pages.
Extended European Search Report for EP Application No. 13859067.4, dated Aug. 16, 2017, 6 pages.
Extended European Search Report for EP Application No. 18188136.8, dated May 16, 2019, 9 pages.
Notice of Reasons for Rejection for Japanese Application No. 2018-081980, dated Feb. 21, 2019, 9 pages.
Notice of Reasons for Rejection dated Aug. 2, 2021 for Japanese Application No. 2020-094488, with English translation, 4 pages.
International Search Report and Written Opinion for International Application No. PCT/US2013/072563, dated Feb. 7, 2014, 11 pages.
Extended European Search Report dated Aug. 30, 2021 for European Application No. 20207898.6, 8 pages.
Extended European Search Report for EP Application No. 16808502.5, dated Jan. 23, 2019, 5 pages.
Extended European Search Report for European Application No. 20176877.7, dated Dec. 1, 2020, 9 pages.
International Search Report and Written Opinion for International Application No. PCT/US2016/037160, dated Sep. 30, 2016, 15 pages.
International Search Report and Written Opinion for International Application No. PCT/US2016/050380, dated Dec. 1, 2016, 6 pages.
Extended European Search Report for European Application No. 20167572.5, dated Sep. 30, 2020, 10 pages.
International Search Report and Written Opinion for International Application No. PCT/US2018/036910, dated Sep. 4, 2018, 13 pages.
International Search Report and Written Opinion for International Application No. PCT/US2018/050621, dated Feb. 26, 2018, 11 pages.
Extended European Search Report dated Aug. 2, 2021 for European Application No. 18855938.9, 7 pages.
International Search Report and Written Opinion for International Application No. PCT/US2018/064561, dated Feb. 11, 2019, 9 pages.
Extended European Search Report for European Application No. 18813278.1, dated Oct. 8, 2021, 8 pages.
Notification of the First Office Action for Chinese Application No. 201880088771.7, dated Sep. 3, 2021, with English translation, 17 pages.
International Search Report and Written Opinion for International Application No. PCT/US2019/034626, dated Aug. 22, 2019, 16 pages.
International Search Report and Written Opinion for International Application No. PCT/US2020/022125, dated May 26, 2020, 17 pages.
Arkin, C. F. et al., "Procedures for the Collection of Diagnostic Blood Specimens by Venipuncture; Approved Standard," Fifth Edition, Clinical and Laboratory Standards Institute, vol. 23, No. 32 (2003), 52 pages.
Barnard, D. R. & Arthur, M. M., "Fibronectin (cold insoluble globulin) in the neonate," Clinical and Laboratory Observations, 102(3): 453-455 (1983).
Baxter, "IV Tubing and Access Devices" authored by and published by Baxter, dated Nov. 6, 2006, 105 pages.
BD Saf-T-Intima Closed IV Catheter System, Becton, Dickinson and Company, 2015 Brochure. Retrieved from the Internet (Sep. 11, 2019) <https://www.bd.com/en-us/offerings/capabilities/infusion-therapy/iv-catheters/bd-saf-tintima-closed-iv-catheter-system>, 2 pages.
BD Vacutainer Passive Shielding Blood Collection Needle Brochure; Becton Dickinson and Company (2005), 2 pages.
Brecher, M. E. et al., "Bacterial Contamination of Blood Components," Clinical Microbiology Reviews, 18(1):195-204 (2005).
Calam, R. R., "Recommended 'Order of Draw' for Collecting Blood Specimens into Additive-Containing Tubes," Letter to the Editor, Clinical Chemistry, 28(6):1399 (1982), 1 page.
Cartridge and Test Information, Abbott, Art: 714258-010 Rev. Date: Aug. 15, 2016, 6 pages.
Challiner, A. et al., Queen Alexandra Hospital, Portsmouth P06 3LY, "Venous/arterial blood management protection system," Correspondence, p. 169.
De Korte, D. et al., "Diversion of first blood volume results in a reduction of bacterial contamination for whole-blood collections," Vox Sanguinis, 83:13-16 (2002).

(56) References Cited

OTHER PUBLICATIONS

De Korte, D. et al., "Effects of skin disinfection method, deviation bag, and bacterial screening on clinical safety of platelet transfusions in the Netherlands," Transfusion, 46: 476-485 (2006).
Edwards Lifesciences, "Conservation. Safety. Simplicity. Edwards VAMP and VAMP Jr. Systems," 2002 Brochure. Retrieved from the Internet (Sep. 11, 2019) <https:/www.medline.com/media/catalog/Docs/MKT/VAMPSYSTEMBROCHURE.PDF>, 4 pages.
Ernst, D. J. et al., "NCCLS simplifies the order of draw: a brief history," MLO, 26-27 (2004).
Gottlieb, T., "Hazards of Bacterial Contamination of Blood Products," Anaesth Intens Care, 21: 20-23 (1993).
Hall, K. K. et al., "Updated Review of Blood Culture Contamination," Clinical Microbiology Reviews, 19(4):788-802 (2006).
Hillyer, C. D. et al., "Bacterial Contamination of Blood Components Risks, Strategies, and Regulation," Hematology, 575-589 (2003).
Kim, J. Y. et al., "The Sum of the Parts is Greater Than the Whole: Reducing Blood Culture Contamination," Annals of Internal Medicine, 154:202-203 (2011).
Levin, P. D. et al., "Use of the Nonwire Central Line Hub to Reduce Blood Culture Contamination," Chest, 143(3):640-645 (2013).
Pall Corp., "Leukotrap Filtration Systems for Whole Blood Derived Platelets: Leukotrap RC PL and Leukotrap PL Systems," 2005 Brochure, 2 pages.
Li, Y. et al., "Direct labeling and visualization of blood vessels with lipophilic carbocyanine dye Dil," Nature Protocols, 3(11): 1703-1708 (2008).
Liumbruno, G. M. et al., "Reduction of the risk of bacterial contamination of blood components through diversion of the first part of the donation of blood and blood components," Blood Transfus, 7: 86-93 (2009).
Mayer, G. A., "A Method for the Reliable Determination of Clotting Time in Whole Blood," Can Med Assoc J., 72(12): 927-929 (1955).
McDonald, C. P., "Interventions Implemented to Reduce the Risk of Transmission of Bacteria by Transfusion in the English National Blood Service," Transfus Med Hemother, 38:255-258 (2011).
Meissner, G. F. et al., "A Method Based on the Use of Whole Venous Blood in Capillary Tubes," American Journal of Clinical Pathology, 33(2): 29-31 (1963).
Murphy, M., "Better Blood Transfusion," Journal of the Intensive Core Society, 4(3): 78-80 (2003).
Napolitano, M. et al., "Quality control of bacterial contamination of blood components: the feasibility of diversion system testing," Blood Transfus, 2: 231-232 (2004).
Norberg, A. et al., "Contamination Rates of Blood Cultures Obtained by Dedicated Phlebotomy vs Intravenous Catheter," JAMA, 289(6): 726-729 (2003).
Order of Draw for Multiple Tube Collections, LabNotes, a newsletter from BD Diagnostics,—Preanalytical Systems, 17(1):3 (2007).
Page, C. et al., "Blood conservation devices in critical care: a narrative review," Annals of Intensive Care, 3:14 (2013), 6 pages.
Palavecino, E. L. et al., "Detecting Bacterial Contamination in Platelet Products," Clin. Lab., 52:443-456 (2006).
Patel, R. et al., "Optimized Pathogen Detection with 30-Compared to 20-Milliliter Blood Culture Draws." Journal of Clinical Microbiology, 49(12):4047-4051 (2011).
Patton, R. G. et al., "Innovation for Reducing Blood Culture Contamination: Initial Specimen Diversion Technique," Journal of Clinical Microbiology, 48(12):4501-4503 (2010).
Perez, P. et al., "Multivariate analysis of determinants of bacterial contamination of whole-blood donations," Vox Sanguinis, 82:55-60 (2002).
Proehl, J. A. et al., "Clinical Practice Guideline: Prevention of Blood Culture Contamination, Full Version," 2012 ENA Emergency Nurses Resources Development Committee, Emergency Nurses Association (Dec. 2012), 14 pages.
Quilici, N. et al., "Differential Quantitative Blood Cultures in the Diagnosis of Catheter-Related Sepsis in Intensive Care Units," Clinical Infectious Diseases 25:1066-1070 (1997).
Schuur, J., "Blood Cultures: When Do they Help and When Do They Harm?" Brigham & Women's Hospital, Department of Emergency Medicine, (Jun. 21-23, 2012), 42 pages.
Sheppard, C. A. et al., "Bacterial Contamination of Platelets for Transfusion: Recent Advances and Issues," LabMedicine, 36(12):767-770 (2005).
Shulman, G., "Quality of Processed Blood for Autotransfusion," The Journal of Extra-Corporeal Technology, 32(1): 11-19 (2000).
Sibley, C. D. et al., "Molecular Methods for Pathogen and Microbial Community Detection and Characterization: Current and Potential Application in Diagnostic Microbiology," Infection, Genetics and Evolution 12:505-521 (2012).
Stohl, S. et al., "Blood Cultures at Central Line Insertion in the Intensive Care Unit: Comparison with Peripheral Venipuncture," Journal of Clinical Microbiology, 49(7):2398-2403 (2011).
Tang, M. et al., "Closed Blood Conservation Device for Reducing Catheter-Related Infections in Children After Cardiac Surgery," Critical Care Nurse, 34(5): 53-61 (2014).
Wagner et al., "Diversion of Initial Blood Flow to Prevent Whole-Blood Contamination by Skin Surface Bacteria: an in vitro model," Transfusion, 40:335-338 (2000).
Wang, P. et al., "Strategies on Reducing Blood Culture Contamination," Reviews in Medical Microbiology, 23:63-66 (2012).
Weinbaum, F. I. et al., "Doing It Right the First Time: Quality Improvement and the Contaminant Blood Culture," Journal of Clinical Microbiology, 35(3): 563-565 (1997).
Weinstein, M. P., "Current Blood Culture Methods and Systems: Clinical Concepts, Technology, and Interpretation of Results," Clinical Infectious Diseases, 23: 40-46 (1996).
Weinstein, M. P., "Minireview: Blood Culture Contamination: Persisting Problems and Partial Progress," Journal of Clinical Microbiology, 41(6): 2275-2278 (2003).
Weinstein, M. P. et al., "The Clinical Significance of Positive Blood Cultures in the 1990s: A Prospective Comprehensive Evaluation of the Microbiology, Epidemiology, and Outcome of Bacteremia and Fungemia in Adults," Clinical Infectious Diseases, 24:584-602 (1997).
Ziegler, et al., "Controlled Clinical Laboratory Comparison of Two Supplemented Aerobic and Anaerobic Media Used in Automated Blood Culture Systems to Detect Bloodstream Infections," J. Clinical Microbiology, 36(3):657-661 (1998).
Zimmon, D. S. et al., "Effect of Portal Venous Blood Flow Diversion on Portal Pressure," J Clin Invest, 65(6):1388-1397 (1980).
Zundert, A. V., "New Closed IV Catheter System," Acta Anaesth. Belg., 56: 283-285 (2005).
Exhibit 01—Defendant's Invalidity Contentions, Invalidity Claim Chart—*U.S. Pat. No. 9,855,001* vs *Barnard NPL*, Aug. 30, 2019, 8 pages.
Exhibit 02—Defendant's Invalidity Contentions, Invalidity Claim Chart—*U.S. Pat. No. 9,855,001* vs *BD Needle NPL*, Aug. 30, 2019, 7 pages.
Exhibit 03—Defendant's Invalidity Contentions, Invalidity Claim Chart—*U.S. Pat. No. 9,855,001* vs *U.S. Pat. No. 6,626,884*, Aug. 30, 2019, 11 pages.
Exhibit 04—Defendant's Invalidity Contentions, Invalidity Claim Chart—*U.S. Pat. No. 9,855,001* vs *U.S. Pat. Pub. No. 2005/161112*, Aug. 30, 2019, 22 pages.
Exhibit 05—Defendant's Invalidity Contentions, Invalidity Claim Chart—*U.S. Pat. No. 9,855,001* vs *U.S. Pat. No. 4,673,386*, Aug. 30, 2019, 21 pages.
Exhibit 06—Defendant's Invalidity Contentions, Invalidity Claim Chart—*U.S. Pat. No. 9,855,001* vs *U.S. Pat. No. 4,904,240*, Aug. 30, 2019, 15 pages.
Exhibit 07—Defendant's Invalidity Contentions, Invalidity Claim Chart—*U.S. Pat. No. 9,855,001* vs *Leukotrap NPL*, Aug. 30, 2019, 38 pages.
Exhibit 09—Defendant's Invalidity Contentions, Invalidity Claim Chart—*U.S. Pat. No. 9,855,001* vs *U.S. Pat. No. 4,106,497*, Aug. 30, 2019, 22 pages.
Exhibit 10—Defendant's Invalidity Contentions, Invalidity Claim Chart—*U.S. Pat. No. 9,855,001* vs *Stopcock-Syringe NPL*, Aug. 30, 2019, 85 pages.

(56) References Cited

OTHER PUBLICATIONS

Exhibit 11—Defendant's Invalidity Contentions, Invalidity Claim Chart—*U.S. Pat. No. 9,855,001* vs *Ziegler NPL*, Aug. 30, 2019, 8 pages.
Exhibit 12—Defendant's Invalidity Contentions, Invalidity Claim Chart—*U.S. Pat. No. 10,028,689* vs *Barnard NPL*, Aug. 30, 2019, 12 pages.
Exhibit 13—Defendant's Invalidity Contentions, Invalidity Claim Chart—*U.S. Pat. No. 10,028,689* vs *U.S. Pat. No. 6,626,884*, Aug. 30, 2019, 29 pages.
Exhibit 14—Defendant's Invalidity Contentions, Invalidity Claim Chart—*U.S. Pat. No. 10,028,689* vs *U.S. Pat. Pub. No. 2005/161112*, Aug. 30, 2019, 48 pages.
Exhibit 15—Defendant's Invalidity Contentions, Invalidity Claim Chart—*U.S. Pat. No. 10,028,689* vs *U.S. Pat. No. 4,673,386*, Aug. 30, 2019, 44 pages.
Exhibit 16—Defendant's Invalidity Contentions, Invalidity Claim Chart—*U.S. Pat. No. 10,028,689* vs *U.S. Pat. No. 4,904,240*, Aug. 30, 2019, 31 pages.
Exhibit 17—Defendant's Invalidity Contentions, Invalidity Claim Chart—*U.S. Pat. No. 10,028,689* vs *Leukotrap NPL*, Aug. 30, 2019, 113 pages.
Exhibit 19—Defendant's Invalidity Contentions, Invalidity Claim Chart—*U.S. Pat. No. 10,028,689* vs *U.S. Pat. No. 4,106,497*, Aug. 30, 2019, 38 pages.
Exhibit 20—Defendant's Invalidity Contentions, Invalidity Claim Chart—*U.S. Pat. No. 10,028,689* vs *Stopcock-Syringe NPL*, Aug. 30, 2019, 268 pages.
Exhibit 21—Defendant's Invalidity Contentions, Invalidity Claim Chart—*U.S. Pat. No. 10,220,139* vs *U.S. Pat. No. 6,626,884*, Aug. 30, 2019, 35 pages.
Exhibit 22—Defendant's Invalidity Contentions, Invalidity Claim Chart—*U.S. Pat. No. 10,220,139* vs *U.S. Pat. Pub. No. 2005/161112*, Aug. 30, 2019, 46 pages.
Exhibit 23—Defendant's Invalidity Contentions, Invalidity Claim Chart—*U.S. Pat. No. 10,220,139* vs *U.S. Pat. No. 4,207,870*, Aug. 30, 2019, 20 pages.
Exhibit 24—Defendant's Invalidity Contentions, Invalidity Claim Chart—*U.S. Pat. No. 10,220,139* vs *U.S. Pat. No. 6,506,182*, Aug. 30, 2019, 15 pages.
Exhibit 25—Defendant's Invalidity Contentions, Invalidity Claim Chart—*U.S. Pat. No. 10,220,139* vs *U.S. Pat. No. 4,673,386*, Aug. 30, 2019, 53 pages.
Exhibit 26—Defendant's Invalidity Contentions, Invalidity Claim Chart—*U.S. Pat. No. 10,220,139* vs *U.S. Pat. No. 4,904,240*, Aug. 30, 2019, 39 pages.
Exhibit 27—Defendant's Invalidity Contentions, Invalidity Claim Chart—*U.S. Pat. No. 10,220,139* vs *Leukotrap NPL*, Aug. 30, 2019, 115 pages.
Exhibit 29—Defendant's Invalidity Contentions, Invalidity Claim Chart—*U.S. Pat. No. 10,220,139* vs *U.S. Pat. No. 4,106,497*, Aug. 30, 2019, 45 pages.
Exhibit 30—Defendant's Invalidity Contentions, Invalidity Claim Chart—*U.S. Pat. No. 10,220,139* vs *Stopcock-Syringe NPL*, Aug. 30, 2019, 246 pages.
Exhibit 31—Defendant's Invalidity Contentions, Invalidity Claim Chart—*U.S. Pat. No. 10,220,139* vs *U.S. Pat. No. 4,349,035*, Aug. 30, 2019, 26 pages.
Exhibit 32—Defendant's Invalidity Contentions, Invalidity Claim Chart—*U.S. Pat. No. 10,220,139* vs *U.S. Pat. Pub. No. 2008/0145933A1*, Aug. 30, 2019, 39 pages.
Exhibit 33—Defendant's Invalidity Contentions, Invalidity Claim Chart—*U.S. Pat. No. 10,039,483* vs *Barnard NPL*, Aug. 30, 2019, 14 pages.
Exhibit 34—Defendant's Invalidity Contentions, Invalidity Claim Chart—*U.S. Pat. No. 10,039,483* vs *U.S. Pat. No. 6,626,884*, Aug. 30, 2019, 22 pages.
Exhibit 35—Defendant's Invalidity Contentions, Invalidity Claim Chart—*U.S. Pat. No. 10,039,483* vs *U.S. Pat. Pub. No. 2005/161112*, Aug. 30, 2019, 45 pages.
Exhibit 36—Defendant's Invalidity Contentions, Invalidity Claim Chart—*U.S. Pat. No. 10,039,483* vs *U.S. Pat. No. 4,673,386*, Aug. 30, 2019, 47 pages.
Exhibit 37—Defendant's Invalidity Contentions, Invalidity Claim Chart—*U.S. Pat. No. 10,039,483* vs *U.S. Pat. No. 4,904,240*, Aug. 30, 2019, 30 pages.
Exhibit 38—Defendant's Invalidity Contentions, Invalidity Claim Chart—*U.S. Pat. No. 10,039,483* vs *Leukotrap NPL*, Aug. 30, 2019, 115 pages.
Exhibit 40—Defendant's Invalidity Contentions, Invalidity Claim Chart—*U.S. Pat. No. 10,039,483* vs *U.S. Pat. No. 4,106,497*, Aug. 30, 2019, 45 pages.
Exhibit 41—Defendant's Invalidity Contentions, Invalidity Claim Chart—*U.S. Pat. No. 10,039,483* vs *Stopcock-Syringe NPL*, Aug. 30, 2019, 214 pages.
Exhibit 42—Defendant's Invalidity Contentions, Invalidity Claim Chart—*U.S. Pat. No. 10,039,483* vs *U.S. Pat. Pub. No. 2008/0145933A1*, Aug. 30, 2019, 38 pages.
Office Action for U.S. Appl. No. 17/525,682, dated Feb. 7, 2022, 12 pages.
Office Action for U.S. Appl. No. 17/532,382, dated Feb. 7, 2022, 10 pages.
Office Action for U.S. Appl. No. 16/379,128, dated Apr. 26, 2022, 14 pages.
Office Action for U.S. Appl. No. 17/710,389, dated Jun. 16, 2022, 25 pages.
Office Action for U.S. Appl. No. 17/710,401, dated Jul. 6, 2022, 22 pages.
Office Action for U.S. Appl. No. 17/710,411, dated Jul. 6, 2022, 22 pages.
Office Action for U.S. Appl. No. 17/591,239, dated May 3, 2022, 21 pages.
Office Action for U.S. Appl. No. 17/684,920, dated Jul. 11, 2022, 12 pages.
Office Action for U.S. Appl. No. 17/591,239, dated Aug. 4, 2022, 26 pages.
Claim Construction Order in *Retractable Technologies, Inc., and Thomas Shaw* v. *Becton Dickinson & Co.*, Civil Action No. 2:07-CV-250 (OF) (Jan. 20, 2009). 32 pages.
Decision of Rejection for Japanese Application No. 2018-081980, dated Jan. 30, 2020, 11 pages.
Declaration of Dr. Erik K. Antonsson, PH.D.. P.E., NAE (Mar. 21, 2023). 137 pages.
Extended European Search Report for European Application No. 22172183.0, dated Sep. 11, 2022, 7 pages.
Extended European Search Report for European Application No. EP22210589.2 dated Apr. 17, 2023, 6 pages.
Extended European Search Report for European Application No. 22194769.0, dated Feb. 28, 2023, 9 pages.
File History of U.S. Appl. No. 15/832,091, filed Dec. 5, 2017, 360 pages.
Final Office Action for U.S. Appl. No. 17/684,920 mailed on Jan. 31, 2023, 9 pages.
First Amended Complaint in *Magnolia Medical Technologies, Inc.* v. *Kurin, Inc.*, C.A. No. 19-cv-00097-CFC, Document 5 (Filed Mar. 7, 2019). 40 pages.
Indian Office Action for Application No. 202017008581dated Mar. 8, 2022, 7 pages.
Kurin, Inc.'s Opening Post-Trial Brief Regarding indefiniteness in *Magnolia Medical Technologies, Inc.* v. *Kurin, Inc.*, C.A. No. 19-097 (CFC)(CJB), Document 463 (Filed Sep. 30, 2022), 24 pages.
Litigation Search Report CRU 3999 for Reexamination U.S. Appl. No. 90/019,177 dated Mar. 23, 2023, 95 pages.
Magnolia's Answer Brief in Opposition to Kurin, Inc.'s Opening Post-Trial Brief Regarding Indefiniteness in *Magnolia Medical Technologies, Inc.* v. *Kurin, Inc.*, C.A. No. 19-097 (CFC)(CJB), Document 463 (Filed Sep. 30, 2022). 25 pages.
Non Final Office Action for U.S. Appl. No. 17/591,239 dated Feb. 17, 2023, 34 pages.
Non-Final Office Action for U.S. Appl. No. 16/815,526 mailed on Aug. 18, 2022, 13 pages.
Notice of Allowance and Search Report for Chinese Application No. CN20188066848 dated Jan. 4, 2023, 4 pages.

(56) References Cited

OTHER PUBLICATIONS

Notice of Reasons for Rejection for Japanese Application No. 2020-094488, dated Mar. 31, 2022, 6 pages.
Notification of the First Office Action for Chinese Application No. 201880066848.0, dated Apr. 20, 2022, 20 pages.
Office Action for Australian Application No. AU20180334138 dated Jun. 24, 2023, 3 pages.
Office Action for Chinese Application No. 201811146373.4, dated Nov. 4, 2020, with English language translation, 17 pages.
Office Action for Chinese Application No. 201811146373.4, dated Aug. 25, 2021, with English language translation, 10 pages.
Office Action for Chinese Application No. 201811146373.4, dated Jan. 29, 2022, with English language translation, 21 pages.
Office Action for Israel Application No. IL20200273025 dated Dec. 4, 2022, 3 pages.
Office Action for Japanese application No. JP20200511930, mailed on Aug. 23, 2022, 9 pages.
Office Action for Japanese Application No. JP20200566232 dated Apr. 12, 2023, 27 pages.
Office Action for U.S. Appl. No. 16/789,034, dated Feb. 9, 2023, 11 pages.
Office Action for U.S. Appl. No. 18/299,680, dated Aug. 15, 2023, 5 pages.
Office Action in Ex Parte Reexamination for U.S. Appl. No. 90/019,177, dated Aug. 9, 2023, 11 pages.
Office Action for U.S. Appl. No. 17/138,056, dated Dec. 21, 2022, 11 pages.
Opening Expert Report of Dr. Juan G. Santiago Regarding Infringement of U.S. Pat. Nos. 9,855,001 and 10,039,483 (Redacted) in *Magnolia Medical Technologies, Inc.* v. *Kurin, Inc.*, CA No. 19-00097-CFC (dated Jan. 15, 2021). 555 pages.
Original Claims of U.S. Appl. No. 14/712,431, filed May 14, 2015. 6 pages.
Redacted Plaintiff's Answering Brief in Opposition to Defendant's Motion for Summary Judgement (No. 3) Of Noninfringement of All Asserted Claims Due to Lack of Sequestration in *Magnolia Medical Technologies, Inc.* v. *Kurin, Inc.*, C.A. No. 19-97 (CFC)(CJB), Document 389 (Filed Jul. 14, 2021). 15 pages.
Reexamination Request Order—Granted, for U.S. Appl. No. 90/019,177, mailed Apr. 26, 2023, 16 pages.
Request for Ex Parte Reexamination Under 35 U.S.C. 302 and 37 C.F.R. 1.510 filed Mar. 22, 2023, 84 pages.
Vent Definition & Meaning—Merriam-Webster (https://www.rnerriam-webster.com/dictionary/vent, accessed Mar. 21, 2023). 16 pages.
Vent, n.2: Oxford English Dictionary (https://www.oed.com/view/Entry/222207?&print, accessed Feb. 16, 2023). 12 pages.
Verdict Form (Phase 2) (Redacted) in *Magnolia Medical Technologies, Inc.* v. *Kurin, Inc.*, CA No. 19-97-CFC (CJB), Document 443 (Filed Jul. 29, 2022). 5 pages.
Verdict Form (Redacted) in *Magnolia Medical Technologies, Inc.* v. *Kurin, Inc.*, C.A. No. 19-97-CFC (CJB), Document 437 (Filed Jul. 26, 2022). 3 pages.
Extended European Search Report for European Application No. 23217471.4, mailed May 22, 2024, 8 pages.
Office Action for Canadian Application No. 3066670, mailed Oct. 4, 2024, 4 pages.
Office Action for U.S. Appl. No. 18/227,185, mailed Oct. 31, 2024, 17 pages.
Office Action for U.S. Appl. No. 18/380,259, mailed Oct. 16, 2024, 15 pages.
Arenas et al., "Asynchronous Testing of 2 Specimen-Diversion Devices to reduce Blood Culture Contamination: A Single-Site Product Supply Quality Improvement Project," J. Emergency Nursing, vol. 47, No. 2, pp. 256-264.e6 (Mar. 2021), 15 pages.
Avatar: "Is it safe to reinfuse blood drawn from a CVAD via a syringe when checking line patency or drawing blood?" [retrieved online Jul. 31, 2024] URL:https://www.avatargroup.org.au/faq---blood-collection.html, 4 pages.
Bauman et al., "Don't Stick Me Again! Reducing Blood Culture Contamination," INOVA Fairfax Medical Campus, Emergency Department (2019), 1 page.
Bell et al., Effectiveness of a Novel Specimen Collection System in Reducing Blood Culture Contamination Rates, J. Emergency Nursing, vol. 44, No. 6, 570 (Nov. 2018), 6 pages.
Blakeney, "Reduction of Blood Culture Contaminations Using Initial Specimen Diversion Device," Beebe Healthcare (Jun. 2018), 1 page.
Brownfield et al., "Emergency Department Observes 83% Reduction in Blood Culture Contamination with Initial Specimen Diversion Technology Adoption," Am. J. Infection Control, vol. 49, S14, ADS 34 (Jun. 2021), 1 page.
Bruneau, Cecile, et al.; "Efficacy of a new collection procedure for preventing bacterial contamination of whole-blood donations," Transfusion (2001); 41(1):74-81.
Case 1: 19-cv-00097-CFC-CJB, *Magnolia Medical Technologies, Inc.*, Plaintiff v. *Kurin, Inc.*, Defendant; Memorandum Opinion, (Document 514) filed Aug. 4, 2023, 38 pages.
Case 1: 19-cv-00097-CFC-CJB, *Magnolia Medical Technologies, Inc.*, Plaintiff v. *Kurin, Inc.*, Defendant; Order, (Document 515) filed Aug. 4, 2023, 1 page.
Case 1: 19-cv-00097-CFC-CJB, *Magnolia Medical Technologies, Inc.*, Plaintiff v. *Kurin, Inc.*, Defendant; Order, (Document 516) filed Aug. 4, 2023, 2 pages.
Chang et al., "Impact of Blood Culture Diversion Device and Molecular Pathogen Identification on Vancomycin Use," San Antonio Military Medical Center (2016), 1 page.
Claim Construction Order, *Magnolia Medical Techs.* v. *Kurin*, Case No. 19-00097-CFC-CJB, at 3 (D. Del.) (May 20, 2020), 4 pages.
Declaration of Dr. Morten Jensen under 37 C.F.R. § 1.132, Oct. 10, 2023, 400 pages.
Doern et al., "A Comprehensive Update on the Problem of Blood Culture Contamination and a Discussion of Methods for Addressing the Problem," Clinical Microbiology, vol. 33, No. 1, e00009-19 (Jan. 2020), 21 pages.
Exhibit A1—Defendant's Invalidity Contentions, Invalidity Claim Chart—*U.S. Pat. No. 9,855,002* vs *U.S. Patent Publication No. 2005/0161112 A1*, Jul. 29, 2024, 234 pages.
Exhibit A10—Defendant's Invalidity Contentions, Invalidity Claim Chart—*U.S. Pat. No. 9,855,002* vs *PortSyringe NPL*, Jul. 29, 2024, 230 pages.
Exhibit A11—Defendant's Invalidity Contentions, Invalidity Claim Chart—*U.S. Pat. No. 9,855,002* vs *U.S. Pat. No. 4,056,101 NPL*, Jul. 29, 2024, 111 pages.
Exhibit A12—Defendant's Invalidity Contentions, Invalidity Claim Chart—*U.S. Pat. No. 9,855,002* vs *U.S. Pat. No. 5,947,932*, Jul. 29, 2024, 156 pages.
Exhibit A3—Defendant's Invalidity Contentions, Invalidity Claim Chart—*U.S. Pat. No. 9,855,002* vs *U.S. Patent Publication No. 2007/0119508*, Jul. 29, 2024, 368 pages.
Exhibit A4—Defendant's Invalidity Contentions, Invalidity Claim Chart—*U.S. Pat. No. 9,855,002* vs *U.S. Pat. No. 5,573,951*, Jul. 29, 2024, 258 pages.
Exhibit A5—Defendant's Invalidity Contentions, Invalidity Claim Chart—*U.S. Pat. No. 9,855,002* vs *U.S. Pat. No. 6,626,884*, Jul. 29, 2024, 116 pages.
Exhibit A6—Defendant's Invalidity Contentions, Invalidity Claim Chart—*U.S. Pat. No. 9,855,002* vs *U.S. Pat. No. 4,673,386*, Jul. 29, 2024, 145 pages.
Exhibit A7—Defendant's Invalidity Contentions, Invalidity Claim Chart—*U.S. Pat. No. 9,855,002* vs *U.S. Pat. No. 4,904,240*, Jul. 29, 2024, 147 pages.
Exhibit A8—Defendant's Invalidity Contentions, Invalidity Claim Chart—*U.S. Pat. No. 9,855,002* vs *Leukotrap NPL*, Jul. 29, 2024, 144 pages.
Exhibit A9—Defendant's Invalidity Contentions, Invalidity Claim Chart—*U.S. Pat. No. 9,855,002* vs *U.S. Pat. No. 4,106,497*, Jul. 29, 2024, 194 pages.
Exhibit B1—Defendant's Invalidity Contentions, Invalidity Claim Chart—*U.S. Pat. No. 10,052,053* vs *U.S. Patent Publication No. 2005/0161112 A1*, Jul. 29, 2024, 237 pages.

(56) References Cited

OTHER PUBLICATIONS

Exhibit B10—Defendant's Invalidity Contentions, Invalidity Claim Chart—*U.S. Pat. No. 10,052,053* vs *PortSyringe NPL*, Jul. 29, 2024, 229 pages.
Exhibit B11—Defendant's Invalidity Contentions, Invalidity Claim Chart—*U.S. Pat. No. 10,052,053* vs *U.S. Pat. No. 4,056,101 NPL*, Jul. 29, 2024, 107 pages.
Exhibit B12—Defendant's Invalidity Contentions, Invalidity Claim Chart—*U.S. Pat. No. 10,052,053* vs *U.S. Pat. No. 5,947,932*, Jul. 29, 2024, 154 pages.
Exhibit B3—Defendant's Invalidity Contentions, Invalidity Claim Chart—*U.S. Pat. No. 10,052,053* vs *U.S. Patent Publication No. 2007/0119508*, Jul. 29, 2024, 373 pages.
Exhibit B4—Defendant's Invalidity Contentions, Invalidity Claim Chart—*U.S. Pat. No. 10,052,053* vs *U.S. Pat. No. 5,573,951*, Jul. 29, 2024, 264 pages.
Exhibit B5—Defendant's Invalidity Contentions, Invalidity Claim Chart—*U.S. Pat. No. 10,052,053* vs *U.S. Pat. No. 6,626,884*, Jul. 29, 2024, 125 pages.
Exhibit B6—Defendant's Invalidity Contentions, Invalidity Claim Chart—*U.S. Pat. No. 10,052,053* vs *U.S. Pat. No. 4,673,386*, Jul. 29, 2024, 146 pages.
Exhibit B7—Defendant's Invalidity Contentions, Invalidity Claim Chart—*U.S. Pat. No. 10,052,053* vs *U.S. Pat. No. 4,904,240*, Jul. 29, 2024, 143 pages.
Exhibit B8—Defendant's Invalidity Contentions, Invalidity Claim Chart—*U.S. Pat. No. 10,052,053* vs *Leukotrap NPL*, Jul. 29, 2024, 136 pages.
Exhibit B9—Defendant's Invalidity Contentions, Invalidity Claim Chart—*U.S. Pat. No. 10,052,053* vs *U.S. Pat. No. 4,106,497*, Jul. 29, 2024, 191 pages.
Exhibit C1—Defendant's Invalidity Contentions, Invalidity Claim Chart—*U.S. Pat. No. 11,529,081* vs *U.S. Patent Publication No. 2005/0161112 A1*, Jul. 29, 2024, 363 pages.
Exhibit C3—Defendant's Invalidity Contentions, Invalidity Claim Chart—*U.S. Pat. No. 11,529,081* vs *U.S. Pat. No. 4,312,362*, Jul. 29, 2024, 354 pages.
Exhibit C4—Defendant's Invalidity Contentions, Invalidity Claim Chart—*U.S. Pat. No. 11,529,081* vs *Kurin Lock NPL*, Jul. 29, 2024, 361 pages.
Exhibit C5—Defendant's Invalidity Contentions, Invalidity Claim Chart—*U.S. Pat. No. 11,529,081* vs *U.S. Pat. No. 4,207,870*, Jul. 29, 2024, 230 pages.
Exhibit C6—Defendant's Invalidity Contentions, Invalidity Claim Chart—*U.S. Pat. No. 11,529,081* vs *U.S. Patent Publication No. 2018/0177445*, Jul. 29, 2024, 479 pages.
Exhibit C7—Defendant's Invalidity Contentions, Invalidity Claim Chart—*U.S. Pat. No. 11,529,081* vs *U.S. Pat. No. 9,820,682*, Jul. 29, 2024, 338 pages.
Exhibit D1—Defendant's Invalidity Contentions, Invalidity Claim Chart—*U.S. Pat. No. 11,653,863* vs *U.S. Patent Publication No. 2005/0161112 A1*, Jul. 29, 2024, 369 pages.
Exhibit D2—Defendant's Invalidity Contentions, Invalidity Claim Chart—*U.S. Pat. No. 11,653,863* vs *U.S. Pat. Nos. 9,855,002 and 10,052,053*, Jul. 29, 2024, 481 pages.
Exhibit D3—Defendant's Invalidity Contentions, Invalidity Claim Chart—*U.S. Pat. No. 11,653,863* vs *U.S. Pat. No. 4,312,362*, Jul. 29, 2024, 334 pages.
Exhibit D4—Defendant's Invalidity Contentions, Invalidity Claim Chart—*U.S. Pat. No. 11,653,863* vs *Kurin Lock NPL*, Jul. 29, 2024, 363 pages.
Exhibit D5—Defendant's Invalidity Contentions, Invalidity Claim Chart—*U.S. Pat. No. 11,653,863* vs *U.S. Pat. No. 4,207,870*, Jul. 29, 2024, 219 pages.
Exhibit D6—Defendant's Invalidity Contentions, Invalidity Claim Chart—*U.S. Pat. No. 11,653,863* vs *U.S. Patent Publication No. 2018/0177445*, Jul. 29, 2024, 447 pages.
Exhibit D7—Defendant's Invalidity Contentions, Invalidity Claim Chart—*U.S. Pat. No. 11,653,863* vs *U.S. Pat. No. 9,820,682*, Jul. 29, 2024, 309 pages.
Exhibit E1—Defendant's Invalidity Contentions, Invalidity Claim Chart—*U.S. Pat. No. 11,903,709* vs *U.S. Patent Publication No. 2005/0161112 A1*, Jul. 29, 2024, 442 pages.
Exhibit E2—Defendant's Invalidity Contentions, Invalidity Claim Chart—*U.S. Pat. No. 11,903,709* vs *U.S. Pat. Nos. 9,855,002 and 10,052,053*, Jul. 29, 2024, 517 pages.
Exhibit E3—Defendant's Invalidity Contentions, Invalidity Claim Chart—*U.S. Pat. No. 11,903,709* vs *U.S. Pat. No. 4,312,362*, Jul. 29, 2024, 438 pages.
Exhibit E4—Defendant's Invalidity Contentions, Invalidity Claim Chart—*U.S. Pat. No. 11,903,709* vs *Kurin Lock NPL*, Jul. 29, 2024, 365 pages.
Exhibit E5—Defendant's Invalidity Contentions, Invalidity Claim Chart—*U.S. Pat. No. 11,903,709* vs *U.S. Pat. No. 4,207,870*, Jul. 29, 2024, 351 pages.
Exhibit E6—Defendant's Invalidity Contentions, Invalidity Claim Chart—*U.S. Pat. No. 11,903,709* vs *U.S. Patent Publication No. 2018/0177445*, Jul. 29, 2024, 559 pages.
Exhibit E7—Defendant's Invalidity Contentions, Invalidity Claim Chart—*U.S. Pat. No. 11,903,709* vs *U.S. Pat. No. 9,820,682*, Jul. 29, 2024, 419 pages.
Extended European Search Report for European Application No. 23182529.0, mailed Dec. 19, 2023, 13 pages.
Extended European Search Report for European Application No. 23218666.8 mailed Apr. 18, 2024, 9 pages.
Geisler et al., "Model to Evaluate the Impact of Hospital-Based Interventions Targeting False-Positive Blood Cultures on Economic and Clinical Outcomes," J. Hospital Infection, vol. 102, No. 4, pp. 438-444 (Mar. 2019).
Lanteri et al., "Reduction of Blood Culture Contaminations in the Emergency Department," Department of Emergency Medicine, San Antonio Military Medical Center (2016), 1 page.
McDonald, C.P.; "Bacterial risk reduction by improved donor arm disinfection, diversion and bacterial screening," Transfus Med., (2006); 16(6):381-396.
Nielsen et al., "Initial Specimen Diversion Device Reduces Blood Culture Contamination and Vancomycin Use in Academic Medical Centre," J. Hospital Infection, vol. 120:127-133 (Feb. 2022).
Office Action and Search Report for Chinese Application No. 202080033513.6, mailed Oct. 9, 2022, with English translation, 19 pages.
Office Action for Australian Application No. 2020218544, mailed Jul. 31, 2024, 3 pages.
Office Action for Australian Application No. 2022200818, mailed May 11, 2023, 4 pages.
Office Action for Canadian Application No. 3120161, mailed Jun. 20, 2022, 4 pages.
Office Action for Canadian Application No. 3136331, mailed Feb. 21, 2023, 4 pages.
Office Action for Canadian Application No. 3183294, mailed Aug. 19, 2024, 5 pages.
Office Action for Chinese Application No. 202080025953.7, mailed Aug. 28, 2024, with English language translation, 26 pages.
Office Action for European Application No. 20716348.6, mailed Jul. 12, 2022, 7 pages.
Office Action for Israeli Application No. 285289, mailed May 6, 2024, 4 pages.
Office Action for Israeli Application No. 286263, mailed May 12, 2024, 4 pages.
Office Action for Israeli Application No. 309638, mailed Jul. 16, 2024, 3 pages.
Office Action for Japanese Application No. 2020-566232 mailed Sep. 19, 2023, with English translation, 6 pages.
Office Action for Japanese Application No. 2021-552145, mailed Jan. 15, 2024, with English Translation, 9 pages.
Office Action for Japanese Application No. 2022-184274, mailed Jun. 14, 2024, with English Translation, 4 pages.
Office Action for Japanese Application No. 2022-184274, mailed Oct. 27, 2023, with English translation, 6 pages.
Office Action for Japanese Application No. 2022-212405, mailed Jun. 20, 2024, with English translation, 6 pages.
Office Action for Japanese Application No. 2023-075104 mailed Feb. 29, 2024, with English Translation, 9 pages.

(56) References Cited

OTHER PUBLICATIONS

Office Action for U.S. Appl. No. 17/136,882, mailed Apr. 19, 2024, 8 pages.
Office Action for U.S. Appl. No. 17/390,249 mailed Nov. 8, 2023, 9 pages.
Office Action for U.S. Appl. No. 17/403,500, mailed May 20, 2024, 28 pages.
Office Action for U.S. Appl. No. 17/591,239, mailed Aug. 23, 2023, 23 pages.
Office Action for U.S. Appl. No. 17/863,605, mailed Nov. 28, 2023, 15 pages.
Office Action for U.S. Appl. No. 18/130,207 mailed Aug. 21, 2023, 7 pages.
Office Action for U.S. Appl. No. 18/227,185, mailed Apr. 18, 2024, 18 pages.
Office Action for U.S. Appl. No. 18/240,178, mailed Jun. 12, 2024, 16 pages.
Office Action for U.S. Appl. No. 18/380,259, mailed Jan. 29, 2024, 33 pages.
Office Action for U.S. Appl. No. 18/381,369, mailed Nov. 28, 2023, 16 pages.
Office Action for U.S. Appl. No. 18/399,007, mailed Mar. 7, 2024, 8 pages.
Office Action for U.S. Appl. No. 18/407,010, mailed Mar. 13, 2024, 8 pages.
Office Action for U.S. Appl. No. 18/407,010, mailed Sep. 6, 2024, 11 pages.
Office Action for U.S. Appl. No. 18/675,824, mailed Jul. 26, 2024, 13 pages.
Office Action for U.S. Appl. No. 18/676,186, mailed Aug. 5, 2024, 13 pages.
Povroznik, "Initial Specimen Diversion Device Utilization Mitigates Blood Culture Contamination Across Regional Community Hospital and Acute Care Facility," Am. J. Medical Quality, vol. 37, No. 5, 405 (Mar. 2022), 8 pages.
Rupp et al., "Reduction in Blood Culture Contamination Through Use of Initial Specimen Diversion Device," Clinical Infectious Diseases, vol. 65, No. 2, 201 (Jul. 15, 2017), 19 pages.
Skoglund et al., "Estimated Clinical and Economic Impact through Use of a Novel Blood Collection Device To Reduce Blood Culture Contamination in the Emergency Department: a Cost-Benefit Analysis," J Clin Microbiol. (Jan. 2019); 57(1):e01015-18, 10 pages.
Steed et al., "Study Demonstrates Reduction in Blood Culture Contamination Rates with Novel Blood Culture Collection Device," Clinical Lab Products Magazine (Feb. 2018), 2 pages.
Tompkins et al., "Getting to Zero: Impact of A Device To Reduce Blood Culture Contamination and False-Positive Central-Line-Associated Bloodstream Infection," Infection Control & Hospital Epidemiology, pp. 1-5 (Nov. 2022).
Tongma et al., "Significant Reduction of Blood Culture Contamination in the Emergency Department (ED) Using the Steripath® Blood Diversion Device," Open Forum Infectious Diseases, vol. 4, Supp. 1, 2035 (Oct. 2017), 1 page.
Zimmerman et al., "Reducing Blood Culture Contamination Using an Initial Specimen Diversion Device," Am. J. Infection Control, vol. 47, No. 7, pp. 822-826 (Jan. 2019).
Chamarthy, P., et al.; "Mixing Characteristics in a Serpentine Micro-Channel," IMECE2004-61902; Proceedings of the ASME 2004 International Mechanical Engineering Congress and Exposition. Fluids Engineering. Anaheim, California, USA; Nov. 13-19, 2004, pp. 253-261; Exhibit 4; 10 pages.
Declaration of Dr. Erik K. Antonsson, Ph.D., P.E., NAE, U.S. Pat. No. 10,052,053, dated Dec. 5, 2024, 138 pages.
Declaration of Dr. Erik K. Antonsson, Ph.D., P.E., NAE, U.S. Pat. No. 11,529,081, dated Jan. 20, 2025, 164 pages.
Declaration of Dr. Erik K. Antonsson, Ph.D., P.E., NAE, U.S. Pat. No. 11,653,863, dated Jan. 20, 2025, 169 pages.
Declaration of Dr. Erik K. Antonsson, Ph.D., P.E., NAE, U.S. Pat. No. 11,903,709, dated Jan. 20, 2025, 161 pages.
Declaration of Dr. Erik K. Antonsson, Ph.D., P.E., NAE, U.S. Pat. No. 9,855,002, dated Dec. 5, 2024, 141 pages.
Declaration of Professor Steven T. Wereley, PH.D., *Magnolia Medical Technologies, Inc.* v. *Kurin, Inc.*, C.A. 24-01124-CFC (D. Del.), Document # 181, dated Apr. 14, 2025, 37 pages.
Exhibit C2—Defendant's Invalidity Contentions, Invalidity Claim Chart—*U.S. Pat. No. 11,529,081* vs *U.S. Pat. Nos. 9,855,002 and 10,052,053*, Jul. 29, 2024, 488 pages.
Exhibit D to Magnolia's First Amended Disclosure of Asserted Claims and Infringement Contentions, *Magnolia Medical Technologies, Inc.* v. *Kurin, Inc.*, C.A. 3-24-cv-00428 (S.D. Cal.), served May 28, 2024, 222 pages.
Exhibit E to Magnolia's First Amended Disclosure of Asserted Claims and Infringement Contentions, *Magnolia Medical Technologies, Inc.* v. *Kurin, Inc.*, C.A. 3-24-cv-00428 (S.D. Cal.), served May 28, 2024, 239 pages.
Extended European Search Report for European Application No. 19156636.3, mailed Aug. 27, 2019, 7 pages.
Extended European Search Report for European Application No. 19190772.4, mailed Feb. 10, 2020, 7 pages.
Extended European Search Report for European Application No. 21197514.9, mailed Mar. 30, 2022, 9 pages.
Extended European Search Report for European Application No. 23153164.1, mailed Aug. 7, 2023, 8 pages.
Extended European Search Report for European Application No. 23171135.9, mailed Oct. 30, 2023, 8 pages.
Extended European Search Report for European Application No. 23209844.2, mailed Mar. 20, 2024, 9 pages.
Extended European Search Report for European Application No. 24217446.4, mailed Apr. 17, 2025, 8 pages.
File History of U.S. Appl. No. 15/432,310, filed Feb. 14, 2017, 246 pages.
Garstecki, P., et al.; "Formation of droplets and bubbles in a microfluidic T-junction-scaling and mechanism of break-up," Lab Chip; 6(3):437-446 (Mar. 2006).
International Search Report and Written Opinion for International Application No. PCT/US2020/017261, mailed May 14, 2020, 13 pages.
Magnolia's Corrected Opening Claim Construction Brief, *Magnolia Medical Technologies, Inc.* v. *Kurin, Inc.*, C.A. 24-01124-CFC (D. Del.), dated Nov. 7, 2024, 32 pages.
Magnolia's Supplemental Claim Construction Brief, *Magnolia Medical Technologies, Inc.* v. *Kurin, Inc.*, C.A. 24-01124-CFC (D. Del.), Document # 180, dated Apr. 14, 2025, 30 pages.
Marshall, L.A., et al.; "An injection molded microchip for nucleic acid purification from 25 microliter samples using isotachophoresis," J Chromatogr A.; 1331; pp. 139-142 (Feb. 2014).
Memorandum Opinion in Support of Judgment of Non-infringement as a Matter of Law, Document 536, *Magnolia Medical Technologies, Inc.* v. *Kurin, Inc.*, C.A. 19-00097-CFC-CJB (D. Del.), May 14, 2024, 21 pages.
Office Action for Australian Application No. 2018279941, mailed Mar. 20, 2023, 3 pages.
Office Action for Australian Application No. 2020234829, mailed Nov. 15, 2024, 3 pages.
Office Action for Australian Application No. 2024203105, mailed Jan. 21, 2025, 3 pages.
Office Action for Australian Application No. 2024203140, mailed Apr. 8, 2025, 4 pages.
Office Action for Canadian Application No. 2932536, mailed Nov. 8, 2019, 6 pages.
Office Action for Canadian Application No. 2932536, mailed Oct. 23, 2020, 6 pages.
Office Action for Canadian Application No. 3074105, mailed Nov. 15, 2024, 5 pages.
Office Action for Canadian Application No. 3087992, mailed Mar. 20, 2025, 4 pages.
Office Action for Canadian Application No. 3101972, mailed May 13, 2025, 4 pages.
Office Action for Canadian Application No. 3129065, mailed Feb. 11, 2025, 3 pages.
Office Action for Chinese Application No. 201811146373.4, mailed Apr. 8, 2025, with English translation, 18 pages.

(56) References Cited

OTHER PUBLICATIONS

Office Action for Chinese Application No. 201880050862.1, mailed Mar. 14, 2022, with English translation, 19 pages.
Office Action for Chinese Application No. 202080025953.7, mailed Dec. 17, 2024, with English language translation, 22 pages.
Office Action for Chinese Application No. 202080025953.7, mailed Jan. 9, 2024, with English translation, 27 pages.
Office Action for Chinese Application No. 202080025953.7, mailed May 24, 2025, with English language translation, 12 pages.
Office Action for Chinese Application No. 202310257287.5, mailed Apr. 23, 2025, with English translation, 21 pages.
Office Action for European Application No. 20709440.0, mailed Feb. 18, 2025, 6 pages.
Office Action for Ex Parte Reexamination for U.S. Appl. No. 90/019,177, mailed Dec. 1, 2023, 19 pages.
Office Action for Ex Parte Re-examination of U.S. Appl. No. 90/019,756, mailed Jun. 17, 2025, 38 pages.
Office Action for Ex Parte Re-examination of U.S. Appl. No. 90/019,757, mailed Jun. 17, 2025, 27 pages.
Office Action for Israeli Application No. 313917, mailed May 29, 2025, 4 pages.
Office Action for Japanese Application No. 2019-230734, mailed Jan. 5, 2022, with English Translation, 6 pages.
Office Action for Japanese Application No. 2020-517772, mailed Dec. 26, 2022, with English Translation, 6 pages.
Office Action for Japanese Application No. 2020-517772, mailed Mar. 14, 2022, with English Translation, 13 pages.
Office Action for Japanese Application No. 2020-550048, mailed Aug. 5, 2022, with English Translation, 5 pages.
Office Action for Japanese Application No. 2021-546225, mailed Dec. 19, 2023, with English translation, 11 pages.
Office Action for Japanese Application No. 2022-074696 mailed Feb. 20, 2023, with English translation, 11 pages.
Office Action for Japanese Application No. 2024-014849, mailed Apr. 30, 2025, with English translation, 9 pages.
Office Action for Japanese Application No. 2024-020482 mailed Mar. 11, 2025, with English Translation, 16 pages.
Office Action for Japanese Application No. 2024-115518, mailed Jun. 11, 2025, with English Translation, 6 pages.
Office Action for Japanese Application No. 2024-187934, mailed Apr. 28, 2025, with English translation, 12 pages.
Office Action for U.S. Appl. No. 14/728,318, mailed Jul. 18, 2019, 27 pages.
Office Action for U.S. Appl. No. 16/934,975, mailed Oct. 6, 2022, 18 pages.
Office Action for U.S. Appl. No. 17/136,882, mailed Dec. 31, 2024, 6 pages.
Office Action for U.S. Appl. No. 17/136,882, mailed Jun. 9, 2023, 11 pages.
Office Action for U.S. Appl. No. 17/136,882, mailed Nov. 8, 2023, 11 pages.
Office Action for U.S. Appl. No. 17/403,500, mailed Nov. 13, 2024, 27 pages.
Office Action for U.S. Appl. No. 17/516,887, mailed Jan. 13, 2025, 42 pages.
Office Action for U.S. Appl. No. 17/583,791, mailed Dec. 23, 2024, 19 pages.
Office Action for U.S. Appl. No. 17/591,239, mailed Jan. 24, 2025, 32 pages.
Office Action for U.S. Appl. No. 17/869,256, mailed May 5, 2025, 24 pages.
Office Action for U.S. Appl. No. 18/240,178, mailed Feb. 27, 2025, 12 pages.
Office Action for U.S. Appl. No. 18/680,331, mailed Mar. 25, 2025, 8 pages.
Office Action for U.S. Appl. No. 18/680,348, mailed Mar. 25, 2025, 7 pages.
Office Action for U.S. Appl. No. 18/680,377, mailed Mar. 26, 2025, 12 pages.
Office Action for U.S. Appl. No. 18/680,439, mailed Mar. 31, 2025, 8 pages.
Office Action for U.S. Appl. No. 18/680,466, mailed Dec. 30, 2024, 7 pages.
Office Action for U.S. Appl. No. 18/960,441, mailed Jan. 17, 2025, 8 pages.
Office Action for U.S. Appl. No. 18/990,547, mailed Jan. 31, 2025, 10 pages.
Order Granting Request for Ex Parte Reexamination for U.S. Appl. No. 90/019,823, dated Feb. 24, 2025, 16 pages.
Order Granting Request for Ex Parte Reexamination for U.S. Appl. No. 90/019,824, dated Feb. 24, 2025, 18 pages.
Order Granting Request for Ex Parte Reexamination for U.S. Appl. No. 90/019,825, dated Feb. 25, 2025, 15 pages.
Preliminary Amendment of U.S. Appl. No. 17/591,237, filed Feb. 2, 2022, 12 pages.
Preliminary Amendment of U.S. Appl. No. 17/591,239, filed Feb. 2, 2022, 12 pages.
Request for Ex Parte Reexamination for U.S. Pat. No. 11,529,081 Under 35 U.S.C. § 302 and 37 C.F.R. § 1.510, filed Jan. 21, 2025, 179 pages.
Request for Ex Parte Reexamination for U.S. Pat. No. 11,653,863 Under 35 U.S.C. § 302 and 37 C.F.R. § 1.510, filed Jan. 21, 2025, 180 pages.
Request for Ex Parte Reexamination for U.S. Pat. No. 11,903,709 Under 35 U.S.C. § 302 and 37 C.F.R. § 1.510, filed Jan. 21, 2025, 176 pages.
Shen, H., et al.; "A microfluidic chip based sequential injection system with trapped droplet liquid-liquid extraction and chemiluminescence detection," Lab Chip; 6(10):1387-1389 (Oct. 2006).
Transcript of Jury Trial Proceedings of Jul. 25, 2022, Document 434, *Magnolia Medical Technologies, Inc.* v. *Kurin, Inc.*, C.A. 19-00097-CFC-CJB (D. Del.), filed Jul. 25, 2022, 402 pages.
Transcript of Jury Trial Proceedings of Jul. 27, 2022, Document 438, *Magnolia Medical Technologies, Inc.* v. *Kurin, Inc.*, C.A. 19-00097-CFC-CJB (D. Del.), filed Jul. 27, 2022, 412 pages.
Appellant/Patent Owner (Magnolia's) Opening Brief on Appeal, *Magnolia Medical Technologies, Inc.* v. *Kurin, Inc.*; Appeal No. 24-2001 (Fed. Cir.); from C.A. 19-00097-CFC-CJB (D. Del.), dated Aug. 26, 2024, Document 10, 71 pages.
Appellant/Patent Owner (Magnolia's) Reply Brief on Appeal, *Magnolia Medical Technologies, Inc.* v. *Kurin, Inc.*; Appeal No. 24-2001 (Fed. Cir.); from C.A. 19-00097-CFC-CJB (D. Del.), dated Jan. 7, 2025, Document 25, 44 pages.
Appellee/Requester (Kurin's) Brief on Appeal, *Magnolia Medical Technologies, Inc.* v. *Kurin, Inc.*; Appeal No. 24-2001 (Fed. Cir.); from C.A. 19-00097-CFC-CJB (D. Del.), dated Nov. 12, 2024, Document 21, 89 pages.
Judgment in favor of Kurin, Inc. against Magnolia Medical Technologies, Inc.; C.A. 19-00097-CFC-CJB (D. Del.), dated Jun. 10, 2024; Exhibit 1026, 3 pages.
Memorandum Opinion (concerning claim construction) in *Magnolia Medical Technologies, Inc.* v. *Kurin, Inc.*; C.A. 1:19-cv-00097-CFC-CJB (D. Del.), dated May 20, 2020, Exhibit 1030, 14 pages.
Order Granting Kurin's Motion for Judgment of Non-Infringement as a Matter of Law; C.A. 19-00097-CFC-CJB (D. Del.), dated May 14, 2024, Exhibit 1024, 2 pages.
Patent Trial and Appeal Board Decision in Ex Parte Reexamination U.S. Appl. No. 90/019,177, dated May 20, 2025, Exhibit 1003, 22 pages.
Request for Ex Parte Reexamination for U.S. Pat. No. 10,039,483 Under 35 U.S.C. § 302 and 37 C.F.R. § 1.510, filed Jul. 21, 2025, 66 pages.
CA Application No. 3101972, Office Action mailed May 13, 2025; Applicant Magnolia Medical Technologies, Inc.; 4 pages.
EP Application No. 22172183.0, Extended European Search Report mailed Nov. 9, 2022; Applicant Magnolia Medical Technologies, Inc.; 7 pages.
EP Application No. 23218666.8, Extended European Search Report mailed Apr. 18, 2024; Applicant Magnolia Medical Technologies, Inc.; 9 pages.

(56) References Cited

OTHER PUBLICATIONS

JP Application No. 2020-566232, Office Action mailed Apr. 12, 2023; Applicant Magnolia Medical Technologies, Inc., with English Translation; 27 pages.
JP Application No. 2020-566232, Office Action mailed Sep. 19, 2023; Applicant Magnolia Medical Technologies, Inc., with English Translation; 6 pages.
JP Application No. 2024-020482, Office Action mailed Mar. 11, 2025; Applicant Magnolia Medical Technologies, Inc., with English Translation; 16 pages.
PCT Application No. PCT/US2019/034626, International Search Report and Written Opinion mailed Aug. 22, 2019, Applicant Magnolia Medical Technologies, Inc.; 16 pages.
U.S. Appl. No. 16/426,380, Final Office Action mailed May 7, 2021; Inventor Bullington, Gregory J. et al.; 28 pages.
U.S. Appl. No. 16/426,380, Non-Final Office Action mailed Oct. 30, 2020; Inventor Bullington, Gregory J. et al.; 29 pages.
U.S. Appl. No. 17/516,887, Final Office Action mailed Aug. 13, 2025; Inventor Bullington, Gregory J. et al.; 24 pages.
U.S. Appl. No. 17/516,887, Non-Final Office Action mailed Jan. 13, 2025; Inventor Bullington, Gregory J. et al.; 42 pages.
U.S. Appl. No. 17/591,239, Final Office Action mailed Aug. 23, 2023; Inventor Bullington, Gregory J. et al.; 23 pages.
U.S. Appl. No. 17/591,239, Final Office Action mailed Aug. 4, 2022; Inventor Bullington, Gregory J. et al.; 26 pages.
U.S. Appl. No. 17/591,239, Non-Final Office Action mailed Feb. 17, 2023; Inventor Bullington, Gregory J. et al.; 34 pages.
U.S. Appl. No. 17/591,239, Non-Final Office Action mailed Jan. 24, 2025; Inventor Bullington, Gregory J. et al.; 32 pages.
U.S. Appl. No. 17/591,239, Non-Final Office Action mailed May 3, 2022; Inventor Bullington, Gregory J. et al.; 21 pages.
AU Application No. 2013267448, Office Action mailed Nov. 5, 2016; Applicant Magnolia Medical Technologies, Inc.; 3 pages.
AU Application No. 2017216493, Office Action mailed Sep. 19, 2018; Applicant Magnolia Medical Technologies, Inc.; 2 pages.
AU Application No. 2019204941, Office Action mailed Jul. 15, 2019; Applicant Magnolia Medical Technologies, Inc.; 4 pages.
AU Application No. 2020213415, Office Action mailed May 21, 2021; Applicant Magnolia Medical Technologies, Inc.; 3 pages.
AU Application No. 2020234829, Office Action mailed Sep. 11, 2025; Applicant Magnolia Medical Technologies, Inc.; 3 pages.
AU Application No. 2024205062, Office Action mailed Sep. 8, 2025; Applicant Magnolia Medical Technologies, Inc.; 2 pages.
Author Unknown, "BACT/ALERT® Culture Media: Strong Outside, Strong Inside," [website], Biomerieux, (Publication Date Unknown), [Accessed via Internet, publicly available at URL: https://www.biomerieux.com/us/en/our-offer/clinical-products/bact-alert-culture-media-bottles.html.], 10 pages.
Author Unknown, "BD BACTEC™ Blood Culture System," [website], Becton, Dickinson and Company, (Publication Date Unknown), [Accessed via Internet, publicly available at URL: https://www.bd.com/en-us/products-and-solutions/products/product-families/bd-bactec-blood-culture-system.], 9 pages.
Author Unknown, "Changing Blood Culture Collection in Hospitals Across America, Clinical Evidence, Studies," [website], Kurin, (Publication Date Unknown), [Retrieved from Internet on Sep. 15, 2025 at URL: https://www.kurin.com/studies/.], 22 pages.
Author Unknown, "Changing Blood Culture Collection in Hospitals Across America," [website], Kurin, (Publication Date Unknown), [Retrieved from Internet on Sep. 15, 2025 at URL: https://www.kurin.com/clinical-guidelines/.], 11 pages.
Author Unknown, "False Positive Blood Cultures—Improve the accuracy of blood culture," [website], Kurin, (Publication Date Unknown), [Retrieved from Internet on Sep. 15, 2025 at URL: https://www.kurin.com/false-positive-blood-cultures/.], 5 pages.
Author Unknown, "Kurin® Jet™ Blood Culture Collection Ordering Information," [website], Kurin, (Publication Date Unknown), [Accessed via Internet, publicly available at URL: https://www.kurin.com/kurin-jet/.], 2 pages.
Author Unknown, "Kurin Launches Kurin Jet, Redefining the Blood Culture Contamination Device Market," [website], Kurin, (Publication Date Unknown), [Accessed via Internet, publicly available at URL: https://www.kurin.com/kurin-launches-kurin-jet-redefining-the-blood-culture-contamination-device-market/.], 5 pages.
Author Unknown, "Kurin Lock® with Flash Technology: Better than conventional diversion," [website], Kurin, (Publication Date Unknown), [Retrieved from Internet on Sep. 26, 2025 at URL: https://www.kurin.com/kurin-jet/.], 10 pages.
Author Unknown, "Lowering the 3% Blood Culture Contamination Rate Benchmark," [website], Kurin, (Publication Date Unknown), [Retrieved from Internet on Sep. 15, 2025 at URL: https://www.kurin.com/3-percent-standard/.], 4 pages.
Author Unknown, "Newly Released CLSI National Blood Culture Guidelines Identify Best Practices and Evidence-Based Technology Solutions Such as Steripath® to Improve Patient Safety and Outcomes," [website], Magnolia Medical Technologies, Inc., (May 5, 2022), [Retrieved from Internet on Sep. 15, 2025 at URL: https://magnolia-medical.com/news/newly-released-clsi-national-blood-culture-guidelines-identify-best-practices-and-evidence-based-technology-solutions-such-as-steripath-to-improve-patient-safety-and-outcomes/.], 5 pages.
Author Unknown, "The Financial and Clinical Costs of False Positive Blood Cultures," [website], Kurin, (Publication Date Unknown), [Retrieved from Internet on Sep. 15, 2025 at URL: https://www.kurin.com/false-positives-blood-culture-cost/.], 5 pages.
Buzard, B.A. et al., "Evaluation of an Initial Specimen Diversion Device (ISDD) on Rates of Blood Culture Contamination in the Emergency Department," Kans J Med. Mar. 19, 2021; 14(1): 73-76. eCollection 2021.
CA Application No. 2875118, Office Action mailed Apr. 7, 2020; Applicant Magnolia Medical Technologies, Inc. et al; 4 pages.
CA Application No. 2875118, Office Action mailed Mar. 21, 2019; Applicant Magnolia Medical Technologies, Inc. et al; 5 pages.
CA Application No. 2931983, Office Action mailed Oct. 1, 2020; Applicant Magnolia Medical Technologies, Inc.; 3 pages.
CA Application No. 2931983, Office Action mailed Oct. 16, 2019; Applicant Magnolia Medical Technologies, Inc.; 4 pages.
CA Application No. 2932536, Office Action mailed Jul. 13, 2021; Applicant Magnolia Medical Technologies, Inc.; 4 pages.
CA Application No. 3132981, Office Action mailed Aug. 22, 2025; Applicant Magnolia Medical Technologies, Inc.; 5 pages.
CA Application No. 3164339, Office Action mailed Jan. 26, 2026; Applicant Magnolia Medical Technologies, Inc.; 4 pages.
Callado, G. Y. et al., "Diagnostic Stewardship: A Systematic Review and Meta-analysis of Blood Collection Diversion Devices Used to Reduce Blood Culture Contamination and Improve the Accuracy of Diagnosis in Clinical Settings," Open Forum Infect Dis. Aug. 11, 2023; 10(9): ofad433, 10 pages. eCollection Sep. 2023.
CN Application No. 201380040468.7, Office Action mailed Apr. 12, 2017; Applicant Magnolia Medical Technologies, Inc., with English Translation; 8 pages.
CN Application No. 201811146373.4, Office Action mailed Jul. 28, 2025; Applicant Magnolia Medical Technologies, Inc., with English Translation; 36 pages.
CN Application No. 201880088771.7, Office Action mailed May 7, 2022; Applicant Magnolia Medical Technologies, Inc., with English Translation; 5 pages.
CN Application No. 202011295348.X, Office Action mailed Nov. 29, 2023; Applicant Magnolia Medical Technologies, Inc., with English Translation; 10 pages.
CN Application No. 202080094860.X, Office Action mailed Jan. 10, 2025; Applicant Magnolia Medical Technologies, Inc., with English Translation; 20 pages.
Declaration of Dr. Morten Jensen under 37 C.F.R. § 1.132, U.S. Pat. No. 10,052,053; dated Oct. 1, 2025, 79 pages.
Declaration of Dr. Morten Jensen under 37 C.F.R. § 1.132, U.S. Pat. No. 10,052,053, dated Feb. 10, 2026; 74 pages.
Declaration of Dr. Morten Jensen under 37 C.F.R. § 1.132, U.S. Pat. No. 11,653,863, dated Feb. 16, 2026; 84 pages.
Declaration of Dr. Morten Jensen under 37 C.F.R. § 1.132, U.S. Pat. No. 11,903,709, dated Feb. 3, 2026; 80 pages.

(56) References Cited

OTHER PUBLICATIONS

Declaration of Dr. Morten Jensen under 37 C.F.R. 1.132, U.S. Pat. No. 9,855,002; dated Oct. 1, 2025, 61 pages.
Defendant's Amended Invalidity Contentions, U.S. Pat. No. 11,903,709, *Magnolia Medical Technologies, Inc.*, vs. *Kurin, Inc.*, C.A. No. 24-1124-CFC (D. Del.), dated Dec. 10, 2024; 70 pages.
ENA (Emergency Nurses Association), "Clinical Practice Guideline: Synopsis—Prevention of Blood Culture Contamination," [website], Guidelinecentral, (May 8, 2018; last updated Oct. 18, 2025), [Accessed via Internet, publicly available at URL: https://www.guidelinecentral.com/guideline/308349/#section-420.], 1 page.
EP Application No. 16200112.7, Extended European Search Report mailed Feb. 15, 2018; Applicant Magnolia Medical Technologies, Inc.; 3 pages.
EP Application No. 16200112.7, Extended European Search Report mailed Mar. 1, 2017; Applicant Magnolia Medical Technologies, Inc.; 6 pages.
EP Application No. 16843182.3, Extended European Search Report mailed Mar. 26, 2019; Applicant Magnolia Medical Technologies, Inc.; 4 pages.
EP Application No. 17206745.6, Office Action mailed Feb. 18, 2020; Applicant Magnolia Medical Technologies, Inc.; 4 pages.
EP Application No. 18813278.1, Extended European Search Report mailed Feb. 17, 2021; Applicant Magnolia Medical Technologies, Inc.; 4 pages.
EP Application No. 22158983.1, Extended European Search Report mailed Aug. 1, 2022; Applicant Magnolia Medical Technologies, Inc.; 8 pages.
EP Application No. 23173044.1, Extended European Search Report mailed Oct. 27, 2023; Applicant Magnolia Medical Technologies, Inc.; 8 pages.
EP Application No. 23182529.0, Office Action mailed Jul. 29, 2025; Applicant Magnolia Medical Technologies, Inc.; 6 pages.
EP Application No. 25164992.7, Extended European Search Report mailed Aug. 26, 2025; Applicant Magnolia Medical Technologies, Inc.; 8 pages.
Exhibit A to Magnolia's Disclosure of Asserted Claims and Infringement Contentions, *Magnolia Medical Technologies, Inc*. v. *Kurin, Inc*., C.A. 3-24-cv-00428 (S.D. Cal.), served May 28, 2024, 240 pages.
Exhibit A2—Defendant's Invalidity Contentions, Invalidity Claim Chart—*U.S. Pat. No. 9,855,002* vs *Japanese Patent Publication No. H10-211274*, Jul. 29, 2024, 281 pages.
Exhibit B to Magnolia's Disclosure of Asserted Claims and Infringement Contentions, *Magnolia Medical Technologies, Inc*. v. *Kurin, Inc*., C.A. 3-24-cv-00428 (S.D. Cal.), served May 28, 2024, 213 pages.
Exhibit B2—Defendant's Invalidity Contentions, Invalidity Claim Chart—*U.S. Pat. No. 10,052,053* vs *Japanese Patent Publication No*. H10-211274, Jul. 29, 2024, 265 pages.
Exhibit C to Magnolia's First Amended Disclosure of Asserted Claims and Infringement Contentions, *Magnolia Medical Technologies, Inc*. v. *Kurin, Inc*., C.A. 3-24-cv-00428 (S.D. Cal.), served May 28, 2024, 250 pages.
GB Application No. 1506837.2, Office Action mailed Jul. 19, 2017; Applicant Magnolia Medical Technologies, Inc.; 6 pages.
IL Application No. 238991, Office Action mailed Feb. 13, 2020; Applicant Magnolia Medical Technologies, Inc., with English Translation; 10 pages.
IL Application No. 238991, Office Action mailed Nov. 12, 2018; Applicant Magnolia Medical Technologies, Inc., with English Translation; 6 pages.
IL Application No. 286263, Office Action mailed Aug. 5, 2025; Applicant Magnolia Medical Technologies, Inc. et al.; 3 pages. (English Only).
IL Application No. 303591, Office Action mailed Feb. 25, 2024; Applicant Magnolia Medical Technologies, Inc. et al.; 4 pages.
IL Application No. 309638, Office Action mailed Aug. 11, 2025; Applicant Magnolia Medical Technologies, Inc. et al.; 3 pages. (English Only).
IN Application No. 11068/DELNP/2014, Office Action mailed Sep. 28, 2020; Applicant Magnolia Medical Technologies, Inc., with English Translation; 6 pages.
Joint Claim Construction Brief for Kurin, Inc's Asserted Patent of U.S. Pat. Nos. 12,138,052, Document 153; *Magnolia Medical Technologies, Inc*. v. *Kurin, Inc*., C.A. 1:24-cv-01124-CFC (D. Del.); filed Mar. 10, 2025; 31 pages.
Joint Motion for Entry of Partial Judgment of Non-Infringement of U.S. Pat. Nos. 9,855,002 and 10,052,053, with Proposed Partial Judgment, Document 247; *Magnolia Medical Technologies, Inc*. v. *Kurin, Inc*., C.A. 1:24-cv-01124-CFC (D. Del.); filed Jul. 25, 2025, 7 pages.
Joint Proposed Final Jury Instructions (Phase 1), Document 357, *Magnolia Medical Technologies, Inc*. v. *Kurin, Inc*., C.A. 24-01124-CFC (D. Del.), filed Oct. 23, 2025; 59 pages.
JP Application No. 2015-515178, Office Action mailed Feb. 16, 2017; Applicant Magnolia Medical Technologies, Inc. et al., with English Translation; 7 pages.
JP Application No. 2015-545494, Office Action mailed Jun. 19, 2017; Applicant Magnolia Medical Technologies, Inc., with English Translation; 9 pages.
JP Application No. 2017-214629, Office Action mailed Jul. 23, 2019; Applicant Magnolia Medical Technologies, Inc., with English Translation; 8 pages.
JP Application No. 2017-214629, Office Action mailed Sep. 20, 2018; Applicant Magnolia Medical Technologies, Inc., with English Translation; 9 pages.
JP Application No. 2020-075727, Office Action mailed Mar. 28, 2023; Applicant Magnolia Medical Technologies, Inc., with English Translation; 6 pages.
JP Application No. 2020-075727, Office Action mailed May 18, 2022; Applicant Magnolia Medical Technologies, Inc., with English Translation; 11 pages.
JP Application No. 2021-552145, Office Action mailed Sep. 11, 2024; Applicant Magnolia Medical Technologies, Inc., with English Translation; 4 pages.
JP Application No. 2022-074696, Office Action mailed Oct. 25, 2023; Applicant Magnolia Medical Technologies, Inc., with English Translation; 7 pages.
JP Application No. 2022-149585, Office Action mailed Sep. 26, 2023; Applicant Magnolia Medical Technologies, Inc., with English Translation; 9 pages.
JP Application No. 2022-184274, Office Action Appeal Decision No. 2024-016403 mailed Nov. 7, 2025, Applicant Magnolia Medical Technologies, Inc., with English translation; 73 pages.
JP Application No. 2022-212405, Office Action mailed Nov. 29, 2023; Applicant Magnolia Medical Technologies, Inc., with English Translation; 13 pages.
JP Application No. 2022-534220, Office Action mailed Sep. 13, 2024; Applicant Magnolia Medical Technologies, Inc., with English Translation; 8 pages.
JP Application No. 2024-014849, Office Action mailed Jan. 28, 2026; Applicant Magnolia Medical Technologies, Inc., with English Translation; 6 pages.
JP Application No. 2024-127830, Office Action mailed Nov. 4, 2025; Applicant Magnolia Medical Technologies, Inc., with English Translation; 8 pages.
JP Application No. 2024-153369, Office Action mailed Feb. 18, 2026; Applicant Magnolia Medical Technologies, Inc., with English Translation; 6 pages.
JP Application No. 2024-153369, Office Action mailed Sep. 5, 2025; Applicant Magnolia Medical Technologies, Inc., with English Translation; 10 pages.
Kurin Blood Culture Collection; Device Description; KUR-MAG-DE000147; pp. 1-9; Exhibit 181-6, filed Apr. 14, 2025; 10 pages.
Mohajer, M.A., et al.; "The Impact of Initial Specimen Diversion Systems on Blood Culture Contamination," Open Forum Infect Dis.; 10(5):ofad182; pp. 1-6. doi: 10.1093/ofid/ofad182 (Apr. 5, 2023).
Order Magnolia *Medical Technologies, Inc*. v. *Kurin, Inc*., C.A. No. 1:24-cv-01124-CFC (D. Del.); Document 390, dated Nov. 17, 2025; 6 pages.

(56) References Cited

OTHER PUBLICATIONS

Partial Judgment of Infringement of U.S. Appl. No. 10/039,483, Document 512 (Exhibit 1022), *Magnolia Medical Technologies, Inc.* v. *Kurin, Inc.*, C.A. 19-00097-CFC-CJB (D. Del.), dated Jul. 26, 2023, 2 pages.

Partial Judgment of Non-Infringement of U.S. Pat. No. 9855001, Document 410, *Magnolia Medical Technologies, Inc.* v. *Kurin, Inc.*, C.A. 19-00097-CFC-CJB (D.Del.), filed Jun. 10, 2022, 3 pages.

PCT Application No. PCT/US2020/064600, International Search Report and Written Opinion mailed Mar. 18, 2021, Applicant Magnolia Medical Technologies, Inc.; 14 pages.

Snyder, S.R., et al.; "Effectiveness of practices to reduce blood culture contamination: A Laboratory Medicine Best Practices systematic review and meta-analysis," Clin Biochem.; Epub Jun. 16, 2012; 45(Issues 13-14):999-1011. doi: 10.1016/j.clinbiochem.2012.06.007, 13 pages (Sep. 2012).

U.S. Appl. No. 14/712,431, Non-Final Office Action mailed Sep. 14, 2018; Inventor Bullington, Gregory et al.; 10 pages.

U.S. Appl. No. 15/257,185, Non-Final Office Action mailed Aug. 8, 2017; Inventor Bullington, Gregory J. et al.; 5 pages.

U.S. Appl. No. 16/785,170, Non-Final Office Action mailed Sep. 14, 2022; Inventor Bullington, Gregory J. et al.; 11 pages.

U.S. Appl. No. 16/815,521, Non-Final Office Action mailed Oct. 25, 2023; Inventor Bullington, Gregory J. et al.; 9 pages.

U.S. Appl. No. 17/119,732, Non-Final Office Action mailed Aug. 25, 2022; Inventor Bullington, Gregory J. et al.; 30 pages.

U.S. Appl. No. 17/403,500, Final Office Action mailed Jul. 28, 2023; Inventor Bullington, Gregory J. et al.; 18 pages.

U.S. Appl. No. 17/403,500, Non-Final Office Action mailed Sep. 27, 2022; Inventor Bullington, Gregory J. et al.; 29 pages.

U.S. Appl. No. 17/559,081, Non-Final Office Action mailed Jan. 12, 2026; Inventor Bullington, Gregory J. et al.; 10 pages.

U.S. Appl. No. 18/209,327, Non-Final Office Action mailed Dec. 16, 2025; Inventor Patton, Richard G.; 19 pages.

U.S. Appl. No. 18/242,900, Non-Final Office Action mailed Oct. 23, 2025; Inventor Bullington, Gregory J. et al.; 12 pages.

U.S. Appl. No. 18/243,540, Non-Final Office Action mailed Jun. 4, 2025; Inventor Bullington, Gregory J. et al.; 34 pages.

U.S. Appl. No. 18/407,010, Non-Final Office Action mailed Dec. 4, 2025; Inventor Bullington, Gregory J. et al.; 7 pages.

U.S. Appl. No. 18/680,331, Final Office Action mailed Nov. 24, 2025; Inventor Bullington, Gregory J. et al.; 9 pages.

U.S. Appl. No. 18/680,348, Final Office Action mailed Nov. 24, 2025; Inventor Bullington, Gregory J. et al.; 8 pages.

U.S. Appl. No. 18/680,377, Final Office Action mailed Nov. 25, 2025; Inventor Bullington, Gregory J., et al.; 14 pages.

U.S. Appl. No. 18/680,439, Final Office Action mailed Nov. 25, 2025; Inventor Bullington, Gregory J., et al.; 10 pages.

U.S. Appl. No. 18/680,466, Final Office Action mailed Aug. 20, 2025; Inventor Bullington, Gregory J. et al.; 10 pages.

U.S. Appl. No. 19/175,765, Final Office Action mailed Nov. 26, 2025; Inventor Bullington, Gregory J. et al.; 14 pages.

U.S. Appl. No. 19/175,765, Non-Final Office Action mailed Aug. 8, 2025; Inventor Bullington, Gregory J. et al.; 11 pages.

U.S. Appl. No. 19/353,350, Non-Final Office Action mailed Feb. 9, 2026; Inventor Bullington, Gregory et al.; 23 pages.

U.S. Appl. No. 62/439,426, filed Dec. 27, 2016, Inventor Rogers, Bobby E., et al.; 127 pages.

U.S. Appl. No. 90/015,399, Order Granting Request for Ex Parte Reexamination mailed Oct. 21, 2025; Inventor Bullington, Gregory J., et al.; 43 pages.

U.S. Appl. No. 90/019,756, Ex Parte Reexamination Interview Summary mailed Sep. 17, 2025, Inventor Patton, Richard G.; 7 pages.

U.S. Appl. No. 90/019,756, Ex Parte Reexamination Non-Final Action mailed Nov. 10, 2025; Inventor Patton, Richard G.; 44 pages.

U.S. Appl. No. 90/019,756, Order Granting Request for Ex Parte Reexamination mailed Jan. 22, 2025, Inventor Patton, Richard G.; 14 pages.

U.S. Appl. No. 90/019,757, Ex Parte Reexamination Final Action mailed Nov. 28, 2025; Inventor Patton, Richard G.; 46 pages.

U.S. Appl. No. 90/019,757, Ex Parte Reexamination Interview Summary mailed Sep. 17, 2025, Inventor Patton, Richard G.; 7 pages.

U.S. Appl. No. 90/019,757, Order Granting Request for Ex Parte Reexamination mailed Jan. 27, 2025, Inventor Patton, Richard G.; 15 pages.

U.S. Appl. No. 90/019,823, Ex Parte Reexamination Interview Summary mailed Nov. 25, 2025; Inventor Bullington, Gregory J.; 31 pages.

U.S. Appl. No. 90/019,823, Ex-Parte Reexamination mailed Aug. 25, 2025; Inventor Bullington, Gregory J. et al.; 30 pages.

U.S. Appl. No. 90/019,823, Response to Office Action in Ex Parte Reexamination filed Nov. 25, 2025; Inventor Bullington, Gregory J.; 211 pages.

U.S. Appl. No. 90/019,824, Ex Parte Reexamination Non-Final Action mailed Nov. 4, 2025; Inventor Bullington, Gregory J., et al.; 22 pages.

U.S. Appl. No. 90/019,824, Examiner Interview Summary mailed Jan. 29, 2026; Inventor Magnolia Medical Technologies, Inc et al.; 3 pages.

U.S. Appl. No. 90/019,825, Ex Parte Reexamination Non-Final Action mailed Nov. 17, 2025; Inventor Bullington, Gregory J., et al.; 25 pages.

U.S. Appl. No. 90/019,825, Examiner Interview Summary mailed Jan. 29, 2026; Inventor Bullington, Gregory J. et al.; 3 pages.

Valleywise Health Medical Center Case Study "In anticipation of CMS changes, AZ hospital identifies solution to blood culture contaminations with new Kurin Jet™," Brochure; 1 page (Publication Date Unknown).

Verdict Form Phase 1 (Redacted), Document 424, *Magnolia Medical Technologies, Inc.* v. *Kurin, Inc.*, C.A. 24-01124-CFC (D. Del.), filed Dec. 16, 2025; 15 pages.

Widmer, A.F., et al.; "Sterilization of skin and catheters before drawing blood cultures," J Clin Microbiol.; 41(10):4910; 1 page (Oct. 2003).

Wilber, E.P., et al.; "Effect of an initial specimen diversion device on blood-culture contamination rates and vancomycin usage: A quasi-experimental study," Epub Aug. 3, 2023; Infect Control Hosp Epidemiol.; 45(1):100-102 (Jan. 2024).

Zwang, O., et al.; "Analysis of strategies to improve cost effectiveness of blood cultures," J Hosp Med.; 1(5):272-276. doi: 10.1002/jhm.115 (Sep. 2006).

* cited by examiner

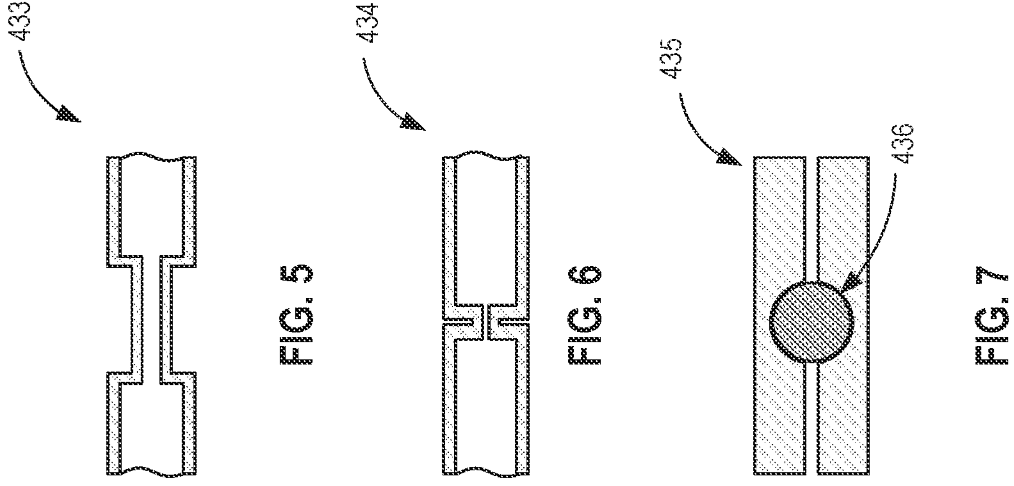
FIG. 5
FIG. 6
FIG. 7
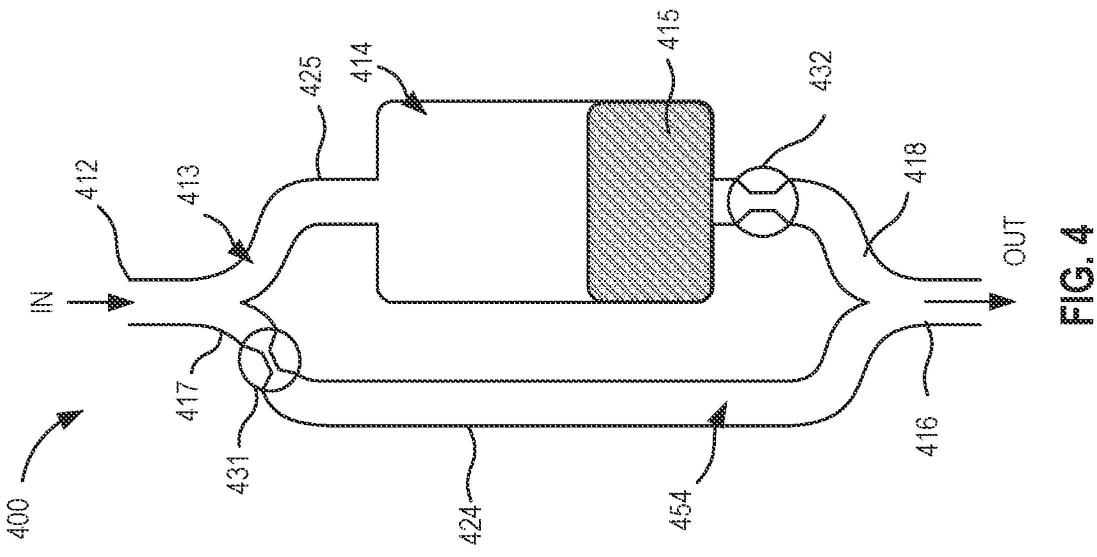
FIG. 4

FLUID CONTROL DEVICES AND METHODS OF USING THE SAME

CROSS-REFERENCE TO RELATED APPLICATIONS

This application is a continuation of U.S. patent application Ser. No. 17/516,887 entitled, "Fluid Control Devices and Methods of Using the Same," filed Nov. 2, 2021, which is a continuation of U.S. patent application Ser. No. 16/426,380 entitled, "Fluid Control Devices and Methods of Using the Same," filed May 30, 2019, which claims priority to and the benefit of U.S. Provisional Patent Application Ser. No. 62/678,637 entitled, "Fluid Control Devices and Methods of Using the Same," filed May 31, 2018, the disclosure of each of which is incorporated herein by reference in its entirety.

BACKGROUND

Embodiments described herein relate generally to the procurement of bodily fluid samples, and more particularly to fluid diversion, sequestration, and/or isolation devices and methods for procuring bodily fluid samples with reduced contaminants such as dermally residing microbes and/or other contaminants exterior to the bodily fluid source.

Health care practitioners routinely perform various types of microbial as well as other broad diagnostic tests on patients using parenterally obtained bodily fluids. As advanced diagnostic technologies evolve and improve, the speed, accuracy (both sensitivity and specificity), and value of information that can be provided to clinicians continues to improve. Maintaining the integrity of the bodily fluid sample during and/or after collection also ensures that analytical diagnostic results are representative of the in vivo conditions of a patient. Examples of diagnostic technologies that are reliant on high quality, non-contaminated, and/or unadulterated bodily fluid samples include but are not limited to microbial detection, molecular diagnostics, genetic sequencing (e.g., deoxyribonucleic acid (DNA), ribonucleic acid (RNA), next-generation sequencing (NGS), etc.), biomarker identification, and/or the like.

Inaccurate results from such testing can be due to the presence biological matter including cells external to the intended sample source and/or other external contaminants that inadvertently are included in the bodily fluid sample being analyzed. In short, when the purity of the bodily fluid sample is compromised during the specimen procurement process, resultant analytical test results may be inaccurate, distorted, adulterated, falsely positive, falsely negative, and/or otherwise not representative of the actual condition of the patient. In turn, these results can lead to faulty, inaccurate, confused, unsure, low-confidence, and/or otherwise undesired clinical decision making.

In some instances, devices and/or systems can be used to reduce the likelihood of contamination, adulteration, and/or the like of bodily fluid samples for testing. For example, some known devices can be configured to collect, divert, separate, and/or sequester (e.g., isolate) an initial volume of bodily fluid that may be more likely to contain contaminants such as dermally residing microbes or the like. Some such devices, however, can be cumbersome, non-intuitive, perceived as difficult to use, inappropriate or unusable for a target patient population, etc. In addition, some such devices can require training, user observation, intervention by more than one user, and/or can otherwise present challenges that can lead to limited efficacy. In some instances, these and/or other challenges can complicate the collection of consistently high quality samples that are non-contaminated, sterile, unadulterated, etc., which in turn, can influence the validity of test result outcomes.

As such, a need exists for fluid control and/or diversion devices and methods for procuring bodily fluid samples with reduced contaminants such as dermally residing microbes and/or other contaminants exterior to the bodily fluid source that result in consistent bodily fluid collection (e.g., from a general patient population and/or a challenging patient population). In addition, a need exists for devices and methods that can include, for example, bodily fluid collection with the assistance of various sources of external energy and/or negative pressure.

SUMMARY

Devices and methods for procuring bodily fluid samples with reduced contaminants such as dermally residing microbes and/or other contaminants exterior to the bodily fluid source are described herein. In some embodiments, a fluid control device includes an inlet and an outlet. The inlet is configured to be placed in fluid communication with a bodily fluid source and the outlet is configured to be placed in fluid communication with a fluid collection device. The coupling of the outlet to the fluid collection device can produce a negative pressure differential within the fluid control device between the outlet and the inlet. The fluid control device has a sequestration portion in fluid communication with the inlet and a sampling portion in fluid communication with the outlet. The sequestration portion includes a first flow controller configured to transition from a first state in which the sequestration portion is sequestered from the outlet to a second state in which the sequestration portion is in fluid communication with the outlet when the negative pressure differential has a first magnitude. The sampling portion includes a second flow controller configured to transition from a first state in which the sampling portion is sequestered from the inlet to a second state in which the sampling portion is in fluid communication with the inlet when the negative pressure differential has a second magnitude greater than the first magnitude.

BRIEF DESCRIPTION OF THE DRAWINGS

FIG. 4 is a schematic illustration of a fluid control device according to an embodiment.

FIGS. 5-7 are each a schematic illustration of a flow controller included in a fluid control device according to various embodiments.

DETAILED DESCRIPTION

Figure 1:
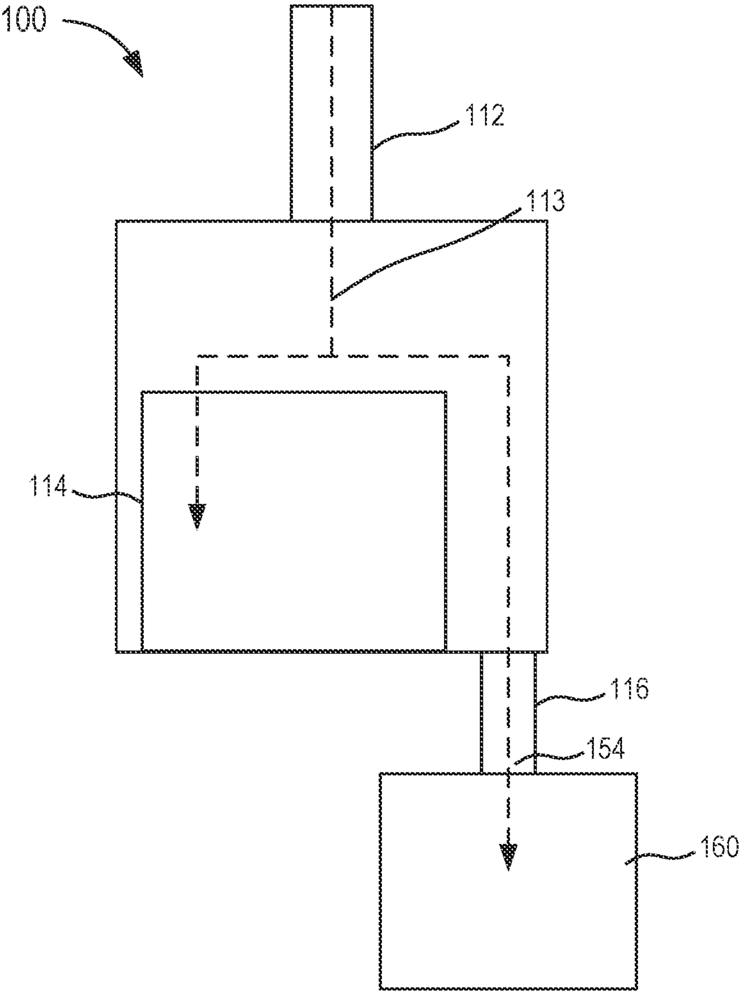
FIG. 1 is a schematic illustration of a fluid control device according to an embodiment.

Devices and methods for collecting, diverting, sequestering, isolating, etc. an initial volume of bodily fluid to reduce contamination in subsequently procured bodily fluid samples are described herein. Any of the fluid control devices described herein can be configured to receive, procure, and/or transfer a flow, bolus, volume, etc., of bodily fluid. A first reservoir, channel, flow path, chamber, and/or portion of the device can receive an initial amount of the bodily fluid flow, which then can be substantially or fully sequestered therein (e.g., contained or retained, circumvented, isolated, segregated, vapor-locked, separated, and/or the like). In some instances, contaminants such as dermally residing microbes or the like can be included and/or entrained in the initial amount of the bodily fluid and likewise are sequestered in or by the first reservoir, flow path, or portion of the device. Once the initial amount is sequestered, any subsequent amount of the bodily fluid flow can be diverted, channeled, directed, and/or otherwise allowed to flow to or through a second portion of the device and/or any additional flow path(s) thereof. Based at least in part on the initial amount being sequestered, subsequent amount(s) of bodily fluid can be substantially free from contaminants that may otherwise produce inaccurate, distorted, adulterated, and/or false results in some diagnostics and/or testing. In some instances, the initial amount of bodily fluid also can be used, for example, in other testing such as those less affected by the presence of contaminants, can be discarded as a waste volume, can be infused back into the patient, and/or can be used for any other suitable clinical application.

In some embodiments, a feature of the fluid control devices and/or methods described herein is the use of an external negative pressure source (e.g., provided by a fluid collection device or any other suitable means) that can (1) overcome physical patient challenges which can limit and/or prevent a sufficient pressure differential to fully engage the sequestration chamber or sequestration portion of the control device and/or to transition fluid flow to the fluid collection device; (2) result in proper filling of the sequestration chamber with a clinically validated and/or desirable volume of bodily fluid; (3) result in efficient, timely, and/or user-accepted consistency with bodily fluid collection process; and/or (4) provide a means of transitioning fluid flow (e.g., automatically or by manipulation to move any number of physical components of the system or by changing, switching, engaging, and/or otherwise providing desired fluid flow dynamics) to enable sequestration and/or isolation of the initial amount (e.g., pre-sample) and collection of a subsequent sample.

In some embodiments, a fluid control device includes an inlet and an outlet. The inlet is configured to be placed in fluid communication with a bodily fluid source and the outlet is configured to be placed in fluid communication with a fluid collection device. The coupling of the outlet to the fluid collection device can produce a negative pressure differential within the fluid control device between the outlet and the inlet. The fluid control device has a sequestration portion in fluid communication with the inlet and a sampling portion in fluid communication with the outlet. The sequestration portion includes a first flow controller configured to transition from a first state in which the sequestration portion is sequestered from the outlet to a second state in which the sequestration portion is in fluid communication with the outlet when the negative pressure differential has a first magnitude. The sampling portion includes a second flow controller configured to transition from a first state in which the sampling portion is sequestered from the inlet to a second state in which the sampling portion is in fluid communication with the inlet when the negative pressure differential has a second magnitude greater than the first magnitude.

In some embodiments, a fluid control device includes a housing, a first flow controller, and a second flow controller. The housing has an inlet configured to establish fluid communication with a bodily fluid source and an outlet configured to be coupled to a fluid collection device. The housing defines a sequestration flow path that is in fluid communication with the inlet and a sampling flow path that is in fluid communication with the outlet. The first flow controller has a flow state in which the sequestration flow path is in fluid communication with the outlet and a non-flow state in which the sequestration flow path is sequestered from the outlet. The second flow controller has a flow state in which sampling flow path is in fluid communication with the inlet and a non-flow state in which the sampling flow path is sequestered from the inlet. The first flow controller configured to be in the flow state when a negative pressure differential generated by coupling the outlet to the fluid collection device has a first magnitude such that an initial volume of bodily fluid flows through the sequestration flow path toward the first flow controller. The first flow controller is configured to transition to the non-flow state when the initial volume of bodily fluid is received in the sequestration flow path such that (1) the sequestration flow path is sequestered from the outlet and (2) the negative pressure differential is increased to a second magnitude operable to transition the second flow controller from the non-flow state to the flow state.

In some embodiments, a method of using a fluid control device to obtain a bodily fluid sample with reduced contamination includes coupling a fluid collection device to an outlet of the fluid control device. The coupling of the fluid collection device to the outlet is configured to produce a negative pressure differential within at least a portion of the fluid control device. A first flow controller is transitioned from a first state to a second state when the negative pressure differential has a first magnitude. The first flow controller is configured to sequester a sequestration portion of the fluid control device from the outlet when in the first state and to establish fluid communication between the sequestration portion and the outlet when in the second state. An initial volume of bodily fluid is received from an inlet of the fluid control device into the sequestration portion in response to the negative pressure differential when the first flow controller is in the second state. The first flow controller is configured to transition from the second state to a third state in response to the sequestration portion receiving the initial volume of bodily fluid. When the first flow controller is in the third state, the first flow controller sequesters the sequestration portion from the outlet the negative pressure differential increases from the first magnitude to a second magnitude. A second flow controller is transitioned from a first state to a second state when the negative pressure differential has the second magnitude. The second flow controller is configured to sequester a sampling portion of the fluid control device from the inlet when in the first state and to establish fluid communication between the sampling portion and the inlet when in the second state. A subsequent volume of bodily fluid is transferred from the inlet to the fluid collection device via the sampling portion and the outlet.

In some embodiments, a fluid control device includes an inlet and an outlet. The inlet is configured to be placed in fluid communication with a bodily fluid source or an intermediary bodily fluid transfer device. The outlet is configured to be placed in fluid communication with a fluid collection device such as, for example, a sample reservoir (bottle, container, dish, vial, etc.), a culture bottle, and evacuated container, a syringe, a lumen-containing device, and/or any other suitable bodily fluid collection and/or transfer device. The fluid control device has a first state in which a negative pressure differential produced from an external source (e.g., the fluid collection device such as a sample reservoir, a syringe, a vessel, and/or any suitable intermediary fluid reservoir) is applied to the fluid control device to draw an initial volume of bodily fluid from the bodily fluid source, through the inlet, and into a sequestration and/or diversion portion of the fluid control device (which can be formed by or in the fluid control device or coupled thereto). The fluid control device has a second state in which (1) the sequestration and/or diversion portion sequesters the initial volume, and (2) the negative pressure differential draws a subsequent volume of bodily fluid, being substantially free of contaminants, from the bodily fluid source, through the fluid control device, and into the fluid collection device.

Any of the embodiments and/or methods described herein can be used in the procurement of clean or substantially unadulterated bodily fluid samples such as, for example, blood samples. In some instances, bodily fluid samples (e.g., blood samples) can be tested for the presence of one or more potentially undesirable microbes, such as bacteria (e.g., Gram-Positive bacteria and/or Gram-Negative bacteria), fungi, yeast (e.g., *Candida*), and/or other undesirable microbes. Various technologies can be employed to assist in the detection of the presence of microbes as well as other types of biological matter, specific types of cells, biomarkers, proteins, antigens, enzymes, blood components, and/or the like during diagnostic testing. Examples include but are not limited to molecular polymerase chain reaction (PCR), magnetic resonance and other magnetic analytical platforms, automated microscopy, spatial clone isolation, flow cytometry, whole blood ("culture free") specimen analysis (e.g., NGS) and associated technologies, morphokinetic cellular analysis, and/or other common or evolving and advanced technologies to characterize patient specimens and/or to detect, identify, type, categorize, and/or characterize specific organisms, antibiotic susceptibilities, and/or the like.

For example, in some instances, microbial testing and/or detection can include incubating blood samples in one or more vessels that may contain culture media (e.g., a nutrient rich and/or environmentally controlled medium to promote growth and/or any number of other mediums), common additives, and/or other types of solutions conducive to microbial growth. Any of the microbes and/or organisms present in the blood sample flourish and/or grow over time in the culture medium (e.g., a variable amount of time from less than an hour to more than several days—which can be longer or shorter depending on the diagnostic technology employed). The presence of the microbes and/or organisms can be detected by automated, continuous monitoring, and/or other methods specific to the analytical platform and/or technology used for detection, identification, and/or the like (e.g., by observing carbon dioxide levels and/or any other suitable methods of detection).

The presence of microbes and/or organisms in the culture medium suggests the presence of the same microbes and/or organisms in the blood sample, which in turn, suggests the presence of the same microbes and/or organisms in the bodily fluid of the patient from whom the sample was obtained. In other instances, a bodily fluid sample may be analyzed directed (i.e., not incubated) for the presence of the microbes and/or organisms. Accordingly, when the microbes and/or organisms are determined to be present in the blood sample, the patient may be diagnosed and prescribed one or more antibiotics or other treatments specifically designed to treat or otherwise remove the undesired microbes and/or organisms from the patient.

Patient samples, however, can become contaminated during procurement and/or otherwise can be susceptible to false results. For example, microbes from a bodily surface (e.g., dermally residing microbes) that are dislodged during the specimen procurement process (e.g., either directly or indirectly via tissue fragments, hair follicles, sweat glands, and other skin adnexal structures) can be subsequently transferred to a culture medium, test vial, or other suitable specimen collection or transfer vessel with the patient sample and/or otherwise included in the specimen that is to be analyzed. Another possible source of contamination is from the person drawing the patient sample (e.g., a doctor, phlebotomist, nurse, technician, etc.) and/or the equipment used for drawing the patient sample. For example, equipment, supplies, and/or devices used during a patient sample procurement process often include multiple fluidic interfaces (e.g., patient to needle, needle to transfer adapter, transfer adapter to sample vessel, catheter hub to syringe, syringe to transfer adapter, needle/tubing to sample vessels, and/or any other fluidic interface or any combination(s) thereof) that can each introduce points of potential contamination. In some instances, such contaminants may thrive in a culture medium and/or may be otherwise identified, thereby increasing a risk or likelihood of false, compromised, and/or erroneous microbial test results, which may inaccurately reflect the presence or lack of such microbes within the patient (i.e., in vivo).

Such inaccurate results because of contamination and/or any other sources of adulteration are a concern when attempting to diagnose or treat a wide range of suspected illnesses, diseases, infections, patient conditions, and/or other maladies. For example, false results from microbial tests may result in a misdiagnosis and/or delayed treatment of a patient illness (which could result in the harm to and/or death of the patient or, on the other hand, may result in the patient being unnecessarily subjected to one or more anti-microbial therapies, which may cause serious side effects to and/or consequences for the patient including, for example, death. As such, false results produce an unnecessary burden and expense on the health care system due to extended length of patient stay and/or other complications associated with erroneous treatments. The use of diagnostic imaging equipment to arrive at these false results is also a concern from both a cost perspective and a patient safety perspective as unnecessary exposure to concentrated radiation associated with a variety of imaging procedures (e.g., CT scans) has many known adverse effects on long-term patient health.

As used in this specification and/or any of the claims included herein, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "about," "approximately," and/or "substantially" when used in connection with a stated value(s) and/or a geometric structure(s) or relationship(s) is intended to convey that the value or characteristic so defined is nominally the value stated and/or characteristic described. In some instances, the terms "about," "approximately," and/or "substantially" can generally mean and/or can generally contemplate a value or characteristic stated within a desirable tolerance (e.g., plus or minus 10% of the value or characteristic stated). For example, a value of about 0.01 would include 0.009 and 0.011, a value of about 0.5 would include 0.45 and 0.55, a value of about 10 would include 9 to 11, and a value of about 1000 would include 900 to 1100. While a value, structure, and/or relationship stated may be desirable, it should be understood that some variance may occur as a result of, for example, manufacturing tolerances or other practical considerations (such as, for example, the pressure or force applied through a portion of a device, conduit, lumen, etc.). Accordingly, the terms "about," "approximately," and/or "substantially" can be used herein to account for such tolerances and/or considerations.

As used herein, "bodily fluid" can include any fluid obtained directly or indirectly from a body of a patient. For example, "bodily fluid" includes, but is not limited to, blood, cerebrospinal fluid, urine, bile, lymph, saliva, synovial fluid, serous fluid, pleural fluid, amniotic fluid, mucus, sputum, vitreous, air, and the like, or any combination thereof.

As used herein, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used herein, the terms "pre-sample," "first," and/or "initial," can be used interchangeably to describe an amount, portion, or volume of bodily fluid that is collected and/or sequestered prior to procuring the "sample" volume. A "pre-sample," "first," and/or "initial" volume can refer to a predetermined, defined, desired, and/or given volume of bodily fluid. For example, a predetermined and/or desired pre-sample volume of bodily fluid can be a drop of bodily fluid, a few drops of bodily fluid, and/or a volume of bodily fluid equal to about 0.1 milliliter (mL), about 0.2 mL, about 0.3 mL, about 0.4 mL, about 0.5 mL, about 1.0 mL, about 2.0 mL, about 3.0 mL, about 4.0 mL, about 5.0 mL, about 10.0 mL, about 20.0 mL, about 50.0 mL, and/or any volume or fraction of a volume therebetween. Alternatively, a pre-sample volume can be greater than 50.0 mL or less than 0.1 mL. In some specific embodiments, a predetermined and/or desired pre-sample volume can be between about 0.1 mL and about 5.0 mL. In other embodiments, a pre-sample volume can be, for example, a combined volume of any number of lumen (e.g., lumen that form at least a portion of a flow path from the bodily fluid source to an initial collection chamber, portion, reservoir, etc.

As used herein, the terms "sample," "second," and/or "subsequent" can be used interchangeably to describe a volume, portion, or amount of bodily fluid that is used, for example, in one or more sample or diagnostic tests. A "sample" volume can be either a random volume or a predetermined or desired volume of bodily fluid collected after collecting, sequestering, and/or isolating a pre-sample volume of bodily fluid. A desired sample volume of bodily fluid can be, for example, between about 10.0 mL to about 60.0 mL. Alternatively, a desired sample volume of bodily fluid can be less than 10.0 mL or greater than 60.0 mL. In some embodiments, for example, a sample volume can be at least partially based on one or more tests, assays, analyses, and/or processes to be performed on the sample volume.

The embodiments described herein can be configured to transfer bodily fluid with reduced contamination and/or substantially free from contamination to one or more fluid collection device(s). In some embodiments, a fluid collection device can include, but is not limited to, any suitable vessel, container, reservoir, bottle, adapter, dish, vial, syringe, device, diagnostic and/or testing machine, and/or the like. In some embodiments, a fluid collection device can be substantially similar to or the same as known sample containers such as, for example, a Vacutainer® (manufactured by Becton Dickinson and Company (BD)), a BacT/ALERT® SN or BacT/ALERT® FA (manufactured by Biomerieux, Inc.), and/or any suitable reservoir, vial, microvial, microliter vial, nanoliter vial, container, microcontainer, nanocontainer, and/or the like. In some embodiments, a fluid collection device can be similar to and/or substantially the same as any of those described in U.S. Pat. No. 8,197,420 entitled, "Systems and Methods for Parenterally Procuring Bodily-Fluid Samples with Reduced Contamination," filed Dec. 13, 2007 ("the '420 patent"), the disclosure of which is incorporated herein by reference in its entirety.

In some embodiments, a fluid collection device can be devoid of contents prior to receiving a sample volume of bodily fluid. For example, in some embodiments, a fluid collection device or reservoir can define and/or can be configured to define or produce a vacuum or suction such as, for example, a vacuum-based collection tube (e.g., a Vacutainer®), a syringe, and/or the like. In some embodiments, a sample reservoir can include, for example, any suitable additives, substances, enzymes, oils, fluids, compounds, chemicals, etc. (e.g., heparin, citrate, acid citrate dextrose (ACD), ethylenediaminetetraacetic acid (EDTA), oxalate, sodium polyanethol sulfonate (SPS), and/or the like). In other embodiments, a sample reservoir can contain, for example, an aerobic culture medium or an anaerobic culture medium. The sample reservoir (e.g., culture bottle) can receive a bodily fluid sample, which can then be tested (e.g., after incubation via in vitro diagnostic (IVD) tests and/or any other suitable test) for the presence of, for example, Gram-Positive bacteria, Gram-Negative bacteria, yeast, fungi, and/or any other organism. If testing of the culture medium yields a positive result, the culture medium can be subsequently tested using, for example, a PCR-based system to identify a specific organism.

While the term "culture medium" can be used to describe a substance configured to react with organisms in a bodily fluid (e.g., microorganisms such as bacteria) and the term "additive" can be used to describe a substance configured to react with portions of the bodily fluid (e.g., constituent cells of blood, serum, synovial fluid, etc.), it should be understood that a sample reservoir can include any suitable substance, liquid, solid, powder, lyophilized compound, gas, etc. Moreover, when referring to an "additive" within a sample reservoir, it should be understood that the additive could be a culture medium, an additive, and/or any other suitable substance, and/or any combination(s) thereof. That is to say, the embodiments described herein can be used with any suitable fluid collection device, reservoir, and/or the like containing any suitable substance.

While some of the embodiments are described herein as being used for procuring bodily fluid for one or more culture sample testing, it should be understood that the embodiments are not limited to such a use. Any of the embodiments and/or methods described herein can be used to transfer a flow of bodily fluid to any suitable device that is placed in fluid communication therewith. Thus, while specific examples are described herein, the devices, methods, and/or concepts are not intended to be limited to such specific examples.

The embodiments described herein and/or portions thereof can be formed or constructed of one or more biocompatible materials. In some embodiments, the biocompatible materials can be selected based on one or more properties of the constituent material such as, for example, stiffness, toughness, durometer, bioreactivity, etc. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly (butyric acid), poly(valeric acid), polyurethanes, and/or blends and copolymers thereof. Examples of non-biodegradable polymers include nylons, polyesters, polycarbonates, polyacrylates, polysiloxanes (silicones), polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof.

The embodiments described herein and/or portions thereof can include components formed of one or more parts, features, structures, etc. When referring to such components it should be understood that the components can be formed by a singular part having any number of sections, regions, portions, and/or characteristics, or can be formed by multiple parts or features. For example, when referring to a structure such as a wall or chamber, the structure can be considered as a single structure with multiple portions, or multiple, distinct substructures or the like coupled to form the structure. Thus, a monolithically constructed structure can include, for example, a set of substructures. Such a set of substructures may include multiple portions that are either continuous or discontinuous from each other. A set of substructures can also be fabricated from multiple items or components that are produced separately and are later joined together (e.g., via a weld, an adhesive, and/or any other suitable method).

Referring now to the drawings, FIG. 1 is a schematic illustration of a fluid control device 100 according to an embodiment. Generally, the fluid control device 100 (also referred to herein as "control device" or "device") is configured to withdrawal bodily fluid from a patient. A first portion or amount (e.g., an initial amount) of the withdrawn bodily fluid is sequestered from a second portion or amount (e.g., a subsequent amount) of the withdrawn bodily fluid which can be subsequently used for additional testing, discarded, and/or reinfused into the patient. In this manner, contaminants or the like can be sequestered within the first portion or amount, leaving the second portion or amount substantially free of contaminants. The second portion or amount of bodily fluid can then be used as a biological sample in one or more tests for the purpose of medical diagnosis and/or treatment (e.g., a blood culture test or the like), as described in more detail herein. The first portion or amount of bodily fluid can be discarded as waste or can be used in any suitable test that is less likely to produce false, inaccurate, distorted, inconsistent, and unreliable results as a result of potential contaminants contained therein. In some circumstances, for example in patients with limited supply of the bodily fluid such as blood, the first portion or amount of bodily fluid can be reinfused back into the patient via any suitable method.

The control device 100 can be any suitable shape, size, and/or configuration. For example, in some embodiments, the control device 100 can have a size that is at least partially based on a volume of bodily fluid at least temporarily stored, for example, in a sequestration, diversion, isolation, and/or storage portion of the control device 100. As described in further detail herein, the control device 100 can be configured to transition between operating modes such that (1) the first portion or amount of bodily fluid selectively flows through at least a first portion of the fluid control device and is subsequently sequestered therein, and (2) the second portion or amount of bodily fluid selectively flows through at least a second portion of the fluid control device and into a fluid collection device or the like. In some embodiments, the control device 100 can be configured to transition between operating modes automatically (e.g., based on pressure differential, time, electronic signal or instruction, saturation of a membrane or member, an absorbent and/or barrier material, etc.) or via and/or in response to intervention (e.g., user intervention, mechanical intervention, or the like).

The control device 100 includes an inlet 112, at least one outlet 116, and a sequestration chamber 114. In addition, the control device 100 defines one or more fluid flow paths 113 between the inlet 112 and at least the sequestration chamber 114 and/or one or more fluid flow paths 154 between the inlet 112 and the outlet(s) 116.

The inlet 112 of the control device 100 is configured to be placed in fluid communication with a bodily fluid source such as, for example, the vasculature of a patient. In some embodiments, the inlet 112 can be coupled to and/or can include an inlet device such as, for example, an intravenous (IV) catheter, a needle, a peripherally inserted central catheter (PICC), a syringe, one or more pieces of sterile tubing, and/or any other suitable lumen-containing device and/or intermediary transfer device. In some embodiments, the inlet 112 can be a port, a valve, and/or the like such as, for example, a Luer Lok® or any other suitable coupler. In such embodiments, the inlet 112 (e.g., port or coupler) can be configured to couple to an access or inlet device in fluid communication with a patient (e.g., a placed or indwelling IV catheter or needle). In some embodiments, the inlet 112 can be physically and fluidically coupled to the access or inlet device via a lock, coupler, port, etc. In other embodiments, the inlet 112 can be in fluid communication with the access or inlet device via an intermediate lumen-containing device such as, for example, sterile tubing or the like. In still other embodiments, the inlet 112 of the control device 100 can form and/or can be integrally or monolithically formed with the access or inlet device.

The sequestration chamber 114 is at least temporarily placed in fluid communication with the inlet 112 via the fluid flow path(s) 113. As described in further detail herein, the sequestration chamber 114 is configured to (1) receive a flow and/or volume of bodily fluid from the inlet 112 and (2) sequester (e.g., separate, segregate, contain, retain, isolate, etc.) the flow and/or volume of bodily fluid therein.

Although not shown in FIG. 1, in some embodiments, the fluid control device 100 can have one or more flow path(s) 113 that include one or more flow modulating features (e.g., flow restrictors, fluid flow retardants, etc.) that selectively modulate the flow of bodily fluid drawn therethrough. In some embodiments, the flow modulating features can be structural and built into the fluid control device 100. In other embodiments, the flow modulating features can be separately formed or can be a material that can be introduced within the fluid control device 100, for example within the sequestration chamber 114, as described in further detail herein.

The sequestration chamber 114 can be any suitable shape, size, and/or configuration. For example, in some embodiments, the sequestration chamber 114 can be at least partially formed by a body portion of the control device 100 (not shown in FIG. 1). In other embodiments, the sequestration chamber 114 can be a reservoir placed and/or disposed within a portion of the control device 100. In other embodiments, the sequestration chamber 114 can be formed and/or defined by a portion of the fluid flow path 113. That is to say, the control device 100 can define one or more lumen and/or can include one or more lumen-defining device(s) configured to receive a flow of bodily fluid from the inlet 112, thereby defining the fluid flow path 113. In such embodiments, at least a portion of the lumen and/or a portion of the lumen-defining device(s) can form and/or can define the sequestration chamber 114.

The sequestration chamber 114 can have any suitable volume and/or fluid capacity. For example, in some embodiments, the sequestration chamber 114 can have a volume and/or fluid capacity between about 0.25 milliliters (mL) and about 5.0 mL. In some embodiments, the sequestration chamber 114 can have a volume measured in volumes as small as a microliter or less of bodily fluid (e.g., a volume as small as 20 drops of bodily fluid, 10 drops of bodily fluid, 5 drops of bodily fluid, a single drop of bodily fluid, or any suitable volume therebetween). In other embodiments, the sequestration chamber 114 can have a volume up to, for example, about 5.0 mL, 10.0 mL, 15.0 mL, 20.0 mL, 30.0 mL, 40.0 mL, 50.0 mL, or more. In some embodiments, the sequestration chamber 114 can have a volume that is equal to and/or that is based at least in part on the volumes of a lumen of the inlet device coupled to and/or included in the control device 100, the lumen of the inlet 112, and a portion of the fluid flow path 113 defined between the inlet 112 and the sequestration chamber 114 and/or any combination thereof. In other embodiments, the sequestration chamber 114 can have a volume that is equal to and/or that is based at least in part on the individual and/or combined volumes of a portion of the inlet device, the inlet 112 of the control device 100, and the portion of the fluid flow path 113 defined between the inlet 112 and the sequestration chamber 114.

Although not shown in FIG. 1, in some embodiments, the fluid control device 100 and/or the sequestration chamber 114 can include and/or can be formed of one or more features or materials configured to interact with a portion of the bodily fluid transferred into the sequestration chamber 114. For example, in some embodiments, the fluid control device 100 and/or the sequestration chamber 114 can include and/or define a valve, a membrane, a diaphragm, a restrictor, a vent, a selectively permeable member (e.g., a fluid impermeable barrier or seal that at least selectively allows the passage of air or gas therethrough), a port, a junction, an actuator, and/or the like, or any suitable combination thereof (collectively referred to herein as a "flow controller"). Such flow controllers can be configured to selectively control (at least in part) a flow of fluids into and/or out of the sequestration chamber 114 and/or any other suitable portion of the fluid control device 100. In this context, the flow of fluids, for example, can be a liquid such as water, oil, dampening fluid, bodily fluid, and/or any other suitable liquid, and/or can be a gas such as air, oxygen, carbon dioxide, helium, nitrogen, ethylene oxide, and/or any other suitable gas.

In some embodiments, one or more openings and/or one or more flow controllers can be configured to facilitate air displacement into or out of the sequestration chamber 114. In some embodiments, the air displacement from the sequestration chamber 114 as an initial portion of the bodily fluid is transferred into the sequestration chamber 114 can allow for a redistribution of pressure in the sequestration chamber 114 and/or between the sequestration chamber 114 and, for example, the fluid source and/or a portion of the fluid flow path outside of the sequestration chamber 114, or a pressure of an ambient environment into which the sequestration chamber 114 is vented. In some embodiments, the redistribution of pressure can be a factor in determining and/or defining how bodily fluid flows through the control device 100 and/or the amount or volume of bodily fluid to be transferred into the sequestration chamber 114.

In other embodiments, the sequestration chamber 114 and/or control device 100 can include a flow controller operable to selectively control a flow of bodily fluid through the fluid flow paths 113 in any suitable manner. For example, in some embodiments, the control device 100 can be configured to selectively transfer a volume of bodily fluid to the sequestration chamber 114 or to the outlet 116 based at least in part on a pressure differential between two or more portions of the control device 100. In some embodiments, the pressure differential can result from fluidically coupling the outlet 116 to an evacuated fluid collection device 160 (e.g., a sample reservoir, a syringe, a pressure charged canister, and/or other source or potential energy to create a vacuum or pressure differential). In other embodiments, the pressure differential can result from a change in volume and/or temperature. In still other embodiments, the pressure differential can result from at least a portion of the control device 100, and/or other portions of the flow paths 113 and/or 154 being evacuated and/or charged (e.g., the sequestration chamber 114 and/or any other suitable portion). In some embodiments, the pressure differential can be established automatically or via direct or indirect intervention and/or manipulation (e.g., by the user). Moreover, a flow of a fluid (e.g., gas and/or liquid) resulting from a pressure differential can be selectively controlled via one or more flow controllers that can, for example, transition between one or more operating conditions to control the fluid flow. It should be understood that the flow controllers included in the embodiments described herein are presented by way of example and not limitation. Thus, while specific flow controllers are described herein, it should be understood that fluid flow can be controlled through the control device 100 by any suitable means.

In some embodiments, a wall or structure of the fluid control device 100 can define an opening, aperture, port, orifice, and/or the like that is in fluid communication with the sequestration chamber 114. In some embodiments, the control device 100 can include a semi-permeable member, film, membrane, or material such as a hydrophobic or hydrophilic membrane disposed in or about the opening or elsewhere in the flow paths 113 to selectively allow a flow of air or gas through the opening while limiting or substantially preventing a flow of fluid (e.g., bodily fluid such as blood) through the opening.

In some embodiments, for example, the control device 100 can include an absorbent and/or hydrophilic material disposed within the sequestration chamber 114. Accordingly, when bodily fluid is transferred into the sequestration chamber 114, the absorbent and/or hydrophilic material can absorb, attract, retain, expand, and/or otherwise interact with at least a portion of the bodily fluid, which in turn, can sequester and/or retain at least an initial portion of the bodily fluid within the sequestration chamber 114, as described in further detail herein.

In some embodiments, the fluid control device 100 can include one or more self-sealing vent materials that permit the flow of air or air pressure (e.g., vacuum) but not the flow of fluid (i.e., liquid). For example, the self-sealing material when wetted or when in contact with a fluid may absorb or otherwise become saturated and transition to a sealed configuration such that the self-sealing material does not permit air or liquid therethrough. The transitioning of the self-sealing material (e.g., vent) may be associated with the fluid control device 100 moving from a first state (e.g., wherein an initial portion of the bodily fluid is being transferred into the sequestration chamber 114) to a second state (e.g., after the initial portion of the bodily fluid is transferred into the sequestration chamber 114).

In some embodiments, the sequestration chamber 114 or any other portion of the fluid control device 100 can include and/or can be formed of an expandable or collapsible material configured to transition between a first state (e.g., while an initial portion of the bodily fluid is being transferred into the sequestration chamber 114) to a second state (e.g., after the initial portion of the bodily fluid is transferred into the sequestration chamber 114). For example, the collapsible material can be in the form of a dissolvable substance that initially blocks the flow path 113 within which it is present and does not permit the flow of fluid (e.g., gas or liquid) therethrough. Upon coming into contact with a predetermined amount of fluid, however, the material can be dissolved or otherwise transitioned to a dissolved configuration to release the obstruction of the fluid flow path 113 in which the material is disposed. In some embodiments, the change in configuration resulting from such a material expanding, collapsing, dissolving, etc. can be operable to transition the control device 100 and/or any suitable portion of the control device 100 from a first state, mode, position, configuration, etc., to a second state, mode, position, configuration, etc., as described in further detail herein.

In some embodiments, the control device 100 and/or the sequestration chamber 114 can include a valve such as, for example, a duckbill valve, a butterfly valve, a one-way check valve, etc. and can be made from any suitable material with any suitable cracking pressure (e.g., an amount of pressure or force sufficient to open the valve) to be used to direct fluid flow as desired. For example, the fluid control device 100 can include two or more valves with varying cracking pressure such that they open sequentially with increasing pressure. Such a configuration can be used, for example, in conjunction with a suitable source of negative pressure and suitable flow controllers to direct fluid flow.

The outlet(s) 116 is/are in fluid communication with and/or is/are configured to be placed in fluid communication with the fluid flow paths 113 and/or 154. The outlet 116 can be any suitable outlet, opening, port, stopcock, lock, seal, coupler, valve (e.g., a one-way check valve, duckbill valve, umbrella valve, and/or the like), etc. and is configured to be fluidically coupled to the fluid collection device 160. In some embodiments, the outlet 116 can be monolithically formed with the collection device 160, a syringe, and/or other intermediary bodily-fluid transfer device. In other embodiments, the outlet 116 can be at least temporarily coupled to the collection device 160 via an adhesive, a resistance fit, a mechanical fastener, a threaded coupling, a piercing or puncturing arrangement, any number of mating recesses, and/or any other suitable coupling or combination thereof. Similarly stated, the outlet 116 can be physically (e.g., mechanically) and/or fluidically coupled to the collection device 160 such that an interior volume defined by the collection device 160 is in fluid communication with the outlet 116. In still other embodiments, the outlet 116 can be operably coupled to the collection device 160 via an intervening structure (not shown in FIG. 1), such as a flexible sterile tubing. In still other embodiments, the outlet 116 can be fluidically coupled to a downstream source of negative pressure that suitably directs the flow of fluid into the collection device 160.

In some embodiments, the arrangement of the outlet 116 can be such that the outlet 116 is physically and/or fluidically sealed prior to coupling to the collection device 160. In some embodiments, the outlet 116 can be transitioned from a sealed configuration to an unsealed configuration in response to being coupled to the collection device 160 and/or in response to a negative pressure differential between an environment within the outlet 116 and/or control device 100 and an environment within the collection device 160.

The fluid collection device 160 can be any suitable device for at least temporarily containing a bodily fluid, such as, for example, those described above. For example, in some embodiments, the fluid collection device 160 can be a single-use disposable collection tube(s), a syringe, a vacuum-based collection tube(s), an intermediary bodily-fluid transfer device, and/or the like. In some embodiments, the fluid collection device 160 can be substantially similar to or the same as known sample containers such as, for example, a Vacutainer®, a BacT/ALERT® SN or BacT/ALERT® FA, and/or any other suitable reservoir, vial, microvial, microliter vial, nanoliter vial, container, microcontainer, nanocontainer, and/or the like. In some embodiments, the collection device 160 can be a sample reservoir that includes a vacuum seal that maintains negative pressure conditions (vacuum conditions) inside the sample reservoir, which in turn, can facilitate withdrawal of bodily fluid from the patient, through the fluid control device 100, and into the sample reservoir, via a vacuum or suction force, as described in further detail herein. In embodiments in which the fluid collection device 160 is an evacuated container or the like, the user can couple the collection device 160 to the outlet 116 to initiate a flow of bodily fluid from the patient such that a first or initial portion of the bodily fluid is transferred into and sequestered by the sequestration chamber 114 and such that any subsequent portion or volume of bodily fluid bypasses and/or is otherwise diverted away from the sequestration chamber 114 and flows into the fluid collection device 160.

Although the outlet 116 of the control device 100 is described above as being fluidically coupled to and/or otherwise placed in fluid communication with the fluid collection device 160 (e.g., a sample reservoir, syringe, etc.), in other embodiments, the control device 100 can be used in conjunction with any suitable bodily fluid collection device, system, and/or the like. For example, in some embodiments, the fluid control device 100 can be used in any suitable fluid transfer device such as those described in U.S. Patent Publication No. 2015/0342510 entitled, "Sterile Bodily-Fluid Collection Device and Methods," filed Jun. 2, 2015 (referred to herein as the "'510 publication"), the disclosure of which is incorporated herein by reference in its entirety. More particularly, the control device 100 can be used in an "all-in-one" or pre-assembled device (e.g., such as those described in the '510 publication) to receive and sequester an initial volume of bodily fluid such that contaminants in subsequent volumes of bodily fluid are reduced and/or eliminated. In other embodiments, the outlet 116 can include and/or can be coupled to an adapter, outlet needle, and/or the like. For example, in some embodiments, the outlet 116 can be coupled to and/or can include a transfer adapter and/or the like such as, for example, the transfer adapters described in U.S. Patent Publication No. 2015/0246352 entitled, "Apparatus and Methods for Disinfection of a Specimen Container," filed Mar. 3, 2015 (referred to henceforth as the "'352 publication"), the disclosure of which is incorporated herein by reference in its entirety.

As described above, the device 100 can be used to procure a bodily fluid sample having reduced contamination from microbes such as, for example, dermally residing microbes and/or the like. For example, in some instances, a user such as a doctor, physician, nurse, phlebotomist, technician, etc. can manipulate the device 100 to establish fluid communication between the inlet 112 and the bodily fluid source (e.g., a vein of a patient, cerebral spinal fluid (CSF) from the spinal cavity, urine collection, and/or the like). As a specific example, in some instances, the inlet 112 can be coupled to and/or can include a needle or the like that can be manipulated to puncture the skin of the patient and to insert at least a portion of the needle in the vein of the patient, thereby placing the inlet 112 in fluid communication with the bodily fluid source (e.g., the vein, an IV catheter, a PICC, etc.).

In some embodiments, once the inlet 112 is placed in fluid communication with the bodily fluid source (e.g., the portion of the patient), the outlet 116 can be fluidically coupled to the collection device 160. As described above, the collection device 160 can be any suitable reservoir, container, and/or collection system configured to receive a volume of bodily fluid. More particularly, the collection device 160 can be, for example, an evacuated reservoir or container that defines a negative pressure and/or can be a syringe that can be manipulated to produce a negative pressure. In some instances, coupling the outlet 116 to the collection device 160 selectively exposes at least a portion of the fluid flow paths 113 and/or 154 to the negative pressure, thereby resulting in a negative pressure differential operable in drawing bodily fluid from the bodily fluid source (e.g., the patient), through the inlet 112, and into the fluid control device 100.

In some embodiments, the arrangement of the control device 100 is such that when a volume of bodily fluid is transferred to and/or through the inlet 112, an initial portion of the volume of bodily fluid (also referred to herein as an "initial volume" or a "first volume") flows from the inlet 112, through at least a portion of the fluid flow path 113, and into the sequestration chamber 114. That is to say, in some embodiments, the control device 100 can be in first or initial state in which the initial portion or volume of bodily fluid can flow in or through at least a portion the fluid flow path 113 and into the sequestration chamber 114. For example, in some embodiments, the initial state of the control device 100 can be one in which one or more flow controllers (e.g., valves, membranes, diaphragms, restrictors, vents, air permeable and fluid impermeable barriers, ports, and/or the like) are in a first state in which the fluid flow path 113 is exposed to the negative pressure differential via the sequestration chamber 114. In other words, the negative pressure within the sample reservoir 160 (or created by a syringe or other source of negative pressure) can result in a negative pressure (or negative pressure differential) within at least a portion of the sequestration chamber 114 that is operable in drawing an initial flow of bodily fluid into the sequestration chamber 114 when one or more flow controllers is in a first or initial state.

For example, in some embodiments, the control device 100 can include one or more flow controller(s) such as those described above that is at least temporarily fluidically coupled to a flow path between the fluid collection device 160 and the sequestration chamber 114. In some embodiments, the flow controller(s) can be at least temporarily fluidically coupled to a flow path between the fluid collection device 160 and the inlet 112. While in some embodiments the flow controller examples noted above can be, for example, known off-the-shelf components that are used in medical devices to control the flow of fluids and air, in other embodiments, the flow controller can be a custom, proprietary, and/or specifically tailored component integrated into the device 100. When the flow controller is in the first or initial state, the flow controller can allow a flow of fluid therethrough in response to the negative pressure of the collection device 160. In some embodiments, the flow controller is configured to allow only a flow of air or gas through the flow controller and is configured to limit and/or substantially prevent a flow of liquid (e.g., bodily fluid) through the flow controller. As such, the collection device 160 can produce a negative pressure differential that is operable to draw an initial portion and/or amount of bodily fluid into the sequestration chamber 114 when the flow controller is in a first or initial state without allowing the initial portion of bodily fluid to flow into the fluid flow path 154 and/or otherwise out of the sequestration chamber 114.

Although not shown in FIG. 1, in some embodiments, the control device 100 can include a member, device, mechanism, etc. configured to modulate a magnitude of the negative pressure to which the sequestration chamber 114 is exposed. For example, in some embodiments, the control device 100 can include a valve, a membrane, a porous material, a restrictor, and/or any other suitable member and/or device configured to modulate pressure. In some embodiments, modulating and/or controlling a magnitude of the pressure to which the sequestration chamber 114 is exposed can, in turn, modulate a magnitude of pressure exerted on the bodily fluid and/or within a vein of a patient. In some instances, such pressure modulation can reduce, for example, hemolysis of a blood sample and/or a likelihood of collapsing a vein (e.g., which is particularly important in fragile patients needing microbial and/or other diagnostic testing associated with use of the control device 100). In addition, the modulation of the negative pressure can, for example, at least partially control a rate at which the fluid control device 100 transitions between a first configuration or state and a second configuration or state. In some embodiments, modulating the negative pressure can act like a timer. For example, a time between the introduction of the negative pressure differential and the transitioning of the diverter from the first state to the second state can be known, predetermined, calculated, and/or controlled. As such, in some instances, modulating the negative pressure can at least partially control an amount or volume of bodily fluid transferred into the sequestration chamber 114 (e.g., can control a volume of the initial amount of bodily fluid).

The initial portion and/or amount of bodily fluid can be any suitable volume of bodily fluid, as described above. For example, in some instances, the control device 100 can remain in the first state until a predetermined and/or desired volume (e.g., the initial volume) of bodily fluid is transferred to the sequestration chamber 134. In some embodiments, the initial volume can be associated with and/or at least partially based on a volume of the sequestration chamber 114. In other embodiments, the initial volume can be associated with and/or at least partially based on an amount or volume of bodily fluid that can be transferred into the device prior to one or more portions of the control device 100 transitioning from a first operating state or mode to a second operating state or more (e.g., an amount of bodily fluid that can be absorbed by an absorbent, expandable, hydrophilic, and/or a wicking material, an amount of bodily fluid sufficient to fully wet or saturate a vent material or semi-permeable member or membrane, an amount sufficient to equalize one or more pressure differentials within the control device 100, an amount sufficient to transition a valve or actuator, and/or the like).

After the initial volume of bodily fluid is transferred and/or diverted into the sequestration chamber 114, the initial volume is sequestered, segregated, retained, contained, isolated, etc. in the sequestration chamber 114. For example, in some embodiments, the transitioning of the one or more flow controllers from a first state to a second state can be operable to sequester and/or retain the initial portion of the bodily fluid in the sequestration chamber 114. As described in further detail herein, in some instances, contaminants such as, for example, dermally residing microbes or the like dislodged during the venipuncture event, other external sources of contamination, colonization of catheters and PICC lines that are used to collect samples, and/or the like can be entrained and/or included in the initial volume of the bodily fluid and thus, are sequestered in the sequestration chamber 114 when the initial volume is sequestered therein.

With the initial volume transferred and/or diverted into the sequestration chamber 114, the device 100 can transition to the second state in which a subsequent volume(s) of bodily fluid can flow through at least a portion the fluid flow paths 113 and/or 154 from the inlet 112 to the outlet 116. In some embodiments, the control device 100 can passively and/or automatically transition (e.g., without user intervention) from the first state to the second state once the initial volume of bodily fluid is sequestered in the sequestration chamber 114. For example, in some embodiments, filling the sequestration chamber 114 to capacity and/or fully saturating, wetting, and/or impregnating an absorbent or similar material disposed between the sequestration chamber 114 and the sample reservoir 160 can be such that further transfer of bodily fluid into the sequestration chamber 114 is limited and/or substantially prevented due to a removal or diversion of the negative pressure. In other embodiments, the control device 100 can be manually transitioned or transitioned in response to at least an indirect interaction by a user. For example, in some embodiments, a user can at least partially obstruct the opening and/or vent. In other embodiments, the user can actuate an actuator or the like (not shown in FIG. 1) to transition the control device 100 from the first state to the second state. In still other embodiments, at least a portion of the initial volume of bodily fluid can transition the control device 100 from the first state to the second state. For example, the control device 100 can include a bodily fluid activated switch, valve, port, and/or the like. In other embodiments, a volume of bodily fluid can move and/or displace one or more actuators or the like that can, for example, open a port, flow path, and/or outlet. In still other embodiments, a user can manipulate such a switch, valve, port, actuator, etc. to transition the control device 100 from the first state to the second state.

With the collection device 160 fluidically coupled to the outlet 116 and with the control device 100 being in the second state (e.g., the initial volume of bodily fluid is sequestered in or by the sequestration chamber 134), any subsequent volume(s) of the bodily fluid can flow from the inlet 112, through at least one of the fluid flow paths 113 and/or 154, through the outlet 116, and into the collection device 160. Thus, as described above, sequestering the initial volume of bodily fluid in the sequestration chamber 114 prior to collecting or procuring one or more sample volumes of bodily fluid reduces and/or substantially eliminates an amount of contaminants in the one or more sample volumes. Moreover, in some embodiments, the arrangement of the control device 100 can be such that the control device 100 cannot transition to the second state prior to collecting and sequestering the initial volume in the sequestration chamber 114.

Figure 2:
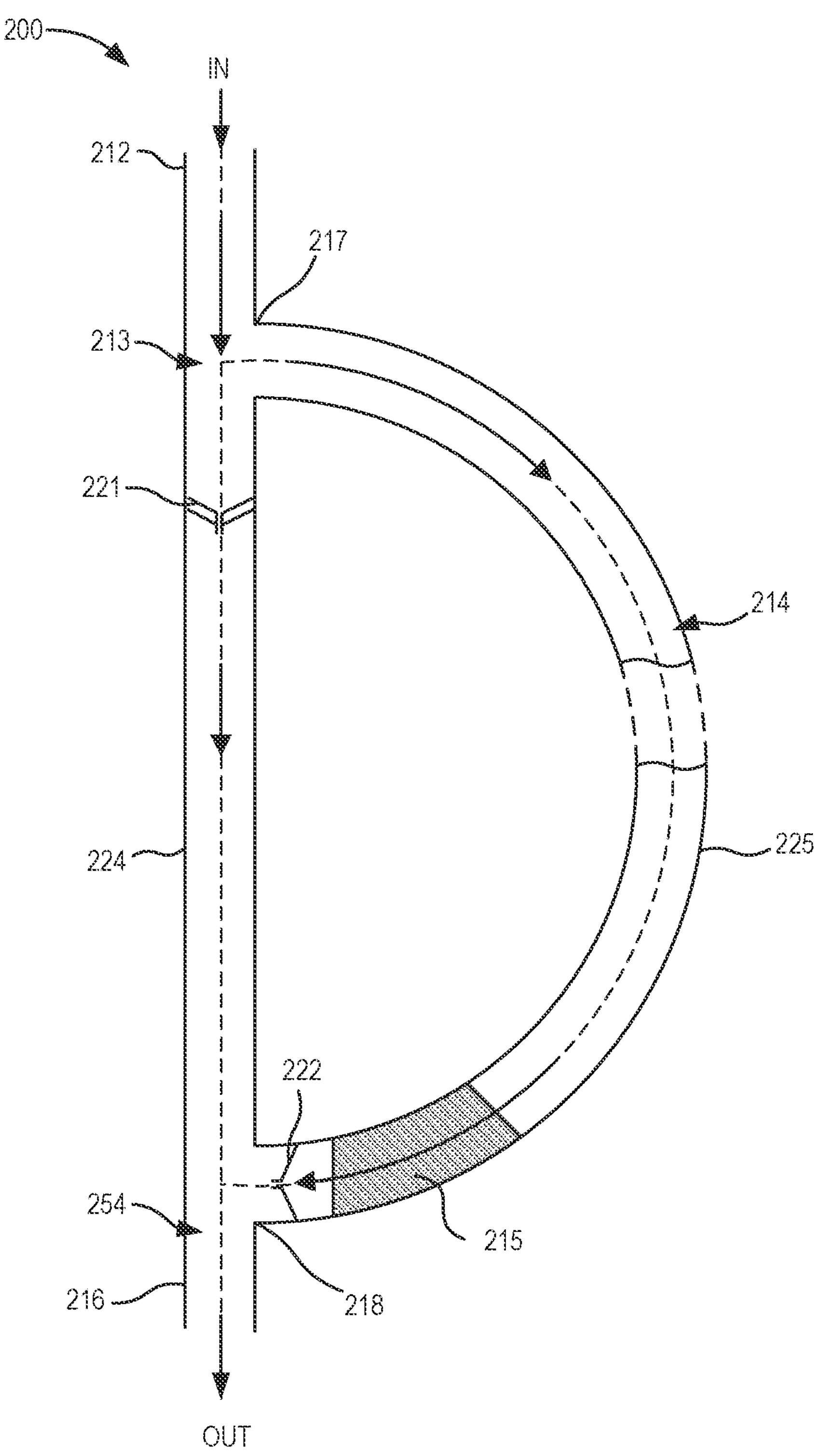
FIG. 2 is a schematic illustration of a fluid control device according to an embodiment.

FIG. 2 illustrates a cross-sectional side-view of a fluid control device 200 according to an embodiment. The fluid control device 200 can be similar in at least form and/or function to the fluid control device 100 described above with reference to FIG. 1. Accordingly, portions of the fluid control device 200 that can be similar to portions of the fluid control device 100 are not described in further detail herein.

As shown in FIG. 2, the fluid control device 200 (also referred to herein as "control device" or "device") includes an inlet 212, an outlet 216, and a sequestration chamber 214. As described above with reference to the control device 100, the inlet 212 is configured to be placed in fluid communication with a bodily fluid source to receive a flow of bodily fluid therefrom (e.g., via a lumen-containing device such as a needle, IV catheter, PICC line, or the like). The outlet 216 is configured to be fluidically coupled to a fluid collection device, a syringe, and/or other intermediary bodily fluid transfer device or vessel (not shown in FIG. 2) such as, for example, a transfer device similar to those described in the '510 publication.

As described above with reference to the fluid control device 100, the control device 200 includes one or more fluid flow paths 213 between the inlet 212 and a sequestration chamber 214 and/or one or more fluid flow paths 254 between the inlet 212 and the outlet 216. The device 200 can have any suitable shape, size, and/or configuration. For example, in some embodiments, the device 200 can be substantially similar in at least form and/or function to the device 100 described above with reference to FIG. 1. In some embodiments, the device 200 can include a first portion 224 and a second portion 225. As shown in FIG. 2, in some embodiments, the second portion 225 can be, for example, a bypass and/or diversion portion that is physically coupled to and selectively in fluid communication with the first portion 224. Moreover, the device 200 includes and/or forms a first junction 217 at a position where a first end (e.g., an inlet end) of the second portion 225 is coupled to the first portion 224 and includes and/or forms a second junction 218 at a position where a second end (e.g., an outlet end) of the second portion 225 is coupled to the first portion 224. That is to say, the device 200 can be configured to have and/or form a bifurcation (e.g., the second portion 225) at the first junction 217 which is rejoined at, for example, the second junction 218. In some embodiments, the second portion 225 can form and/or can have a D-shaped configuration and/or arrangement. In other embodiments, the first portion 224 and/or the second portion 225 can form and/or can have any suitable configuration and/or arrangement (e.g., a serpentine configuration, a looping configuration, a spiraled configuration, any suitable geometric configuration, and/or the like). In some embodiments, the first portion 224 and/or the second portion 225 of the device 200 can include and/or can be formed by flexible tubing or the like having any suitable shape and/or size and being reconfigurable or movable to be placed in any suitable configuration and/or arrangement.

In some embodiments, the sequestration chamber 214 of the device 200 can be formed by and/or included in the second portion 225 of the device 200. The coupling of the second portion 225 to the first portion 224 (e.g., at the first junction 217) is such that the sequestration chamber 214 can be selectively placed in fluid communication with the inlet 212 via the fluid flow path 213 and the first junction 217. Similarly, the coupling of the second portion 225 to the first portion 224 (e.g., at the second junction 218) is such that the sequestration chamber 214 can be selectively placed in fluid communication with the outlet 216 and/or a fluid collection device coupled to the outlet 216 via the fluid flow path 254 and the second junction 218.

As described in further detail herein, the sequestration chamber 214 is configured to (1) selectively receive a flow and/or volume of bodily fluid from the inlet 212 and (2) sequester (e.g., separate, segregate, contain, retain, isolate, etc.) the flow and/or volume of bodily fluid therein. The sequestration chamber 214 can have any suitable shape, size, and/or configuration. For example, in some embodiments, the sequestration chamber 214 can have any suitable size, volume, and/or fluid capacity such as, for example, those described above with reference to the sequestration chamber 114. In some embodiments, at least a portion of the fluid flow path 213 can extend through a portion of the device 200 and/or the first junction 217 to form and/or define at least a portion of the sequestration chamber 214. In other embodiments, the first junction 217 and/or the sequestration chamber 214 can include a flow control mechanism and/or the like that can at least temporarily separate the fluid flow path 213 from the sequestration chamber 214. In some embodiments, the device 200 can include, form, and/or define one or more flow controllers such as flow controllers 221, 222, and/or 215. The flow controllers 221, 222, and/or 215 can be, for example, a valve, membrane, diaphragm, restrictor, vent, a selectively permeable member (e.g., a fluid impermeable barrier or seal that allows at least selective passage of gas or air such as, for example, a blood barrier like Porex®, and/or the like), port, etc. (collectively referred to herein as a "flow controller") placed in one or more desired positions and configured to selectively control (at least in part) a flow of fluids into and/or out of the sequestration chamber 214 and/or any other suitable portion of the device 200.

More particularly, in the embodiment shown in FIG. 2, the flow controllers 221 and 222 each can be a valve configured to have a specific, desired, and/or predetermined cracking pressure or the like. The valves 221 and/or 222 can be, for example, inline or Lined Pipe Insert (LP) valves that can configured to be suitably placed in any position along pipe or tubing systems. In some embodiments, the valves 221 and/or 222 can be configured to stay in a closed state, limiting or substantially preventing the flow of air or liquid, until a specific amount of pressure greater than the cracking pressure is applied on the valves 221 and/or 222 to transition the valve 221 and/or 222, respectively, from a closed state to an open state.

In some embodiments, the valves 221 and/or 222 and other additional valves (not shown) each can be configured to have a variable cracking pressure and to be placed in any suitable position in and/or along the device 200. For example, in some embodiments, as shown in FIG. 2, the valve 221 can be disposed in the first portion 224 of the device 200 and downstream of the first junction 217 and the valve 222 can be disposed in the second portion 225 of the device 200 upstream and/or before the second junction 218. In some embodiments, the device 200 can be configured such that the valve 221 has a greater cracking pressure than the valve 222 such that an applied vacuum source may be used to result in a sequential opening of the valves 221 and 222. For example, the cracking pressure of each of the valves 221 and 222 and the pressure exerted by the source of negative pressure can be collectively configured to achieve a sequential and/or otherwise desired first flow of bodily fluid towards and/or into the sequestration chamber 214 and then a desired second flow of bodily fluid towards the outlet 216 and the fluid collection device.

By way of specific example, in some embodiments, a source of negative pressure (e.g., a fluid collection device and/or the like) can define a vacuum having a magnitude of approximately 8 pounds per square inch (psi). Thus, when the source of negative pressure is coupled to the outlet 216, the pressure is communicated to both valves 221 and 222. In some embodiments, the valve 221 may have, for example, a cracking pressure of 3.4 psi and the valve 222 may have, for example, a cracking pressure of 0.017 psi. As such, the negative pressure differential produced as a result of coupling the negative pressure source to the outlet 216, in turn, can transition the valve 222 (having the lower cracking pressure) from a substantially closed configuration or state to a substantially open configuration or state prior to transitioning the valve 221 (having the higher cracking pressure) from a substantially closed configuration or state to a substantially open configuration or state. In some instances, this sequential opening of the valves (i.e., valve 222 before valve 221), can be operable to direct a flow of fluid (e.g., a first flow) towards the sequestration chamber 214 and then direct the flow of fluid (e.g., a second flow) towards the fluid collection device and/or negative pressure source coupled to the outlet 216, as described further below.

The device 200, can in some embodiments, include one or more flow controllers in the form of materials that are selectively permeable to air but impermeable or at least selectively permeable to fluid (e.g., liquid). For example, the device 200 can include one or more membranes made of material that permit the flow of air or convey a vacuum from a source of negative pressure but do not permit or convey a flow of bodily fluid (e.g., hydrophobic). In some embodiment, the device 200 can include flow controllers that can be in a first or initial state or configuration before interaction with a bodily fluid or any other suitable form of actuation, and then transition and/or be transitioned to a second state or configuration upon interaction with the bodily fluid or a suitable form of actuation. For example, in some embodiments, such flow controllers can be in an initial or first state that selectively permits a flow of air therethrough while substantially limiting and/or preventing a flow of bodily fluid therethrough. Upon interaction with a bodily fluid (or any other suitable fluid), the flow controller can transition to a second state, in which the flow controller can be substantially impermeable to the flow of air and the flow of bodily fluid therethrough.

As shown in the embodiment illustrated in FIG. 2, the device 200 can include a flow controller 215 in the form of a membrane, porous material, absorbent material, etc. The flow controller 215 can be any suitable shape, size, and/or configuration. In some embodiments, the flow controller 215 can be formed of a porous material having any suitable pore size to, for example, permit a flow of air therethrough while limiting and/or substantially preventing a flow of liquid therethrough. For example, in some embodiments, the flow controller 215 can be a membrane or the like having a diameter of about 17 mm and having a pore size of about 0.45 micrometers (μm). In other embodiments, the flow controller 215 can be a membrane and/or the like having any suitable diameter (e.g., 1 mm, 2 mm, 3 mm, 4 mm, 5 mm, 10 mm, 15 mm, 20 mm, 30 mm, or more, and/or any diameter therebetween). Likewise, in other embodiments, the flow controller 215 can be a membrane and/or the like having any suitable pore size. In some embodiments, a pore size for a flow controller, membrane, and/or the like can be based on, for example, the type of fluid (e.g., bodily fluid) to be withdrawn, collected, and/or sequestered, the amount or type of particulate matter expected in the fluid flow (e.g., in the flow of the bodily fluid and/or the flow of air), the vacuum source to be used and/or a magnitude of an expected negative pressure differential, and/or any other suitable factor or consideration.

As shown, the flow controller 215 is positioned within the device 200 to selectively establish fluid communication between the second portion 225 and/or the sequestration chamber 214 and the outlet 216 via the junction 218. Thus, with the flow controller 215 being configured as a semi-permeable member, the flow controller 215 can be configured to at least temporarily allow a gas or air to transfer from the second portion 225 of the device 200 and/or the sequestration chamber 214, through the flow controller 215 and the junction 218, and into the fluid flow path 254 and can be configured to limit and/or substantially prevent a flow of liquid (e.g., bodily fluid) between the second portion 225 and/or the sequestration chamber and the fluid flow path 254 (e.g., via the junction 218), as described in further detail herein. Although not shown, in some embodiments, the device 200 can include one or more actuators or the like configured to control and/or transition the state of the flow controller 215. The outlet 216 of the device 200 is in fluid communication with and/or is configured to be placed in fluid communication with the fluid flow paths 213 and/or 254. The outlet 216 can be any suitable outlet, opening, port, lock, seal, coupler, etc. and is configured to be fluidically coupled to a fluid collection device, such as a sample reservoir, a syringe, container, and/or other sample vessel. In some embodiments, the outlet 216 can be monolithically formed with the fluid collection device or can be at least temporarily coupled to the fluid collection device, as described above with reference to the outlet 116 of the device 100. The fluid collection device can be any suitable collection system for containing a bodily fluid, such as, for example, any of those described in detail above with reference to the collection device 160. More particularly, in some embodiments, the outlet 216 can be configured to couple to an evacuated sample reservoir. In some other embodiments, the outlet 216 can be configured to couple to a source of negative pressure downstream of the outlet 216, while also coupled to the fluid collection device. As such, the user can couple the fluid collection device to the outlet 216 to initiate a flow of bodily fluid from the patient such that a first or initial portion of the bodily fluid is transferred into and sequestered by the sequestration chamber 214 and such that any subsequent portion or volume of bodily fluid bypasses and/or is otherwise diverted away from the sequestration chamber 214 and flows into the fluid collection device.

In operation, the device 200 can be used to procure a bodily fluid sample having reduced contamination from microbes such as, for example, dermally residing microbes and/or the like. For example, in some instances, a user such as a doctor, physician, nurse, phlebotomist, technician, etc. can manipulate the device 200 to establish fluid communication between the inlet 212 and the bodily fluid source (e.g., a vein of a patient). Once the inlet 212 is placed in fluid communication with the bodily fluid source (e.g., the portion of the patient), the outlet 216 can be fluidically coupled to the fluid collection device. As described above, in the embodiment shown in FIG. 2, the fluid collection device can be a negative pressure source and/or can be configured to produce a negative pressure differential. For example, the fluid collection device can be an evacuated reservoir or container that defines a negative pressure, a syringe, a pump, and/or any other negative pressure source. In other embodiments, the fluid collection device can be a container, reservoir, or device configured to be coupled to a separate negative pressure source.

Coupling the outlet 216 to the fluid collection device and/or the source of negative pressure selectively exposes at least a portion of the fluid flow path 254 to the negative pressure within or passing through the fluid collection device. As described above, the flow controller 215 and/or the valves 221 and 222 can be configured to selectively control the flow of fluid through the device 200. More particularly, coupling the outlet 216 to the fluid collection device and/or source of negative pressure results in a negative pressure differential within the fluid flow path 254, which in turn, exposes the valves 221 and 222 to the negative pressure. As described above, in some embodiments, the valve 221 can have a greater cracking pressure (e.g., 3.4 psi) compared to that of the valve 222 (e.g., 0.017 psi). Furthermore, the flow controller 215 upstream of the valve 222 can be a membrane in an initial or first state, in which the flow controller 215 is permeable to a flow of air or gas. In some instances, such an arrangement results in the valve 222 being transitioned from a closed state to an open state such that the negative pressure is communicated through the valve 222 and the flow controller 215 and into the sequestration chamber 214.

Accordingly, a negative pressure differential is produced that is operable in drawing bodily fluid from the bodily fluid source (e.g., the patient), through the inlet 212, and into the fluid flow path 213. Moreover, with the valve 222 in the open state and the valve 221 in the closed state, the bodily fluid can flow through the fluid flow path 213 and into the sequestration chamber 214 (e.g., via the junction 217). As described above with reference to the control device 100, the arrangement of the device 200 is such that when a volume of bodily fluid is transferred to and/or through the inlet 212, an initial portion of the volume of bodily fluid (also referred to herein as an "initial volume" or a "first volume") flows from the inlet 212, through at least a portion of the fluid flow path 213 and/or the junction 217, and into the sequestration chamber 214. That is to say, in some embodiments, the control device 200 can be in first or initial state in which the initial portion or volume of bodily fluid can flow in or through at least a portion the fluid flow path 213 and/or junction 217 and into the sequestration chamber 214. When the device 200 is in the first or initial state, the valve 221 is in a closed state and as such, the bodily fluid does not pass through the valve 221 nor substantially enter the fluid flow path 254.

As described above, the control device 200 can be in the initial state when the flow controller 222 (valve) is in an open state, which in turn, allows the negative pressure differential to draw the initial amount of bodily fluid into the sequestration chamber 214. In some instances, the bodily fluid can flow through the second portion 225 (e.g., the sequestration chamber 214) until the flow reaches the flow controller 215 (e.g., a selectively permeable membrane or member, as described above). The membrane 215 can be in its initial or first state and therefore can be permeable to air but impermeable to liquids. As such, the membrane 215 isolates, separates, segregates, sequesters and/or otherwise prevents direct liquid communication between the fluid flow paths 213 and the sequestration chamber 214. In addition, the inlet 212 is exposed to the negative pressure differential via the sequestration chamber 214. In other words, the negative pressure within the fluid collection device can result in a negative pressure (or negative pressure differential) within at least the second portion 225 of the device 200 (e.g., the sequestration chamber 214) that is operable in drawing an initial flow of bodily fluid from the inlet 212, through at least a portion of the fluid flow path 213 and/or the junction 217, and into the sequestration chamber 214 when the control device 200 is in the first or initial state.

When the flow controller 215 is in the first or initial state, the flow controller 215 can allow a flow of fluid (e.g., a gas or air) therethrough in response to the negative pressure of the sample reservoir (or a syringe or other source of potential energy used to create negative pressure), as described above with reference to the device 100. The flow controller 215 (e.g., selectively permeable membrane or member) can be configured to transition from the first state of being permeable to air and impermeable to liquid, to a second state of being impermeable to air and liquid in response to the flow of the initial amount of bodily fluid into the sequestration chamber 214. For example, the filling of the sequestration chamber 214 to capacity can correspond to and/or otherwise result in the bodily fluid saturating, wetting, and/or impregnating the flow controller 215 (e.g., membrane material), which can transition the flow controller 215 from the first state to the second state. In the second state the flow controller 215 is impermeable to air and liquid, thereby limiting and/or substantially preventing fluid communication between the sequestration chamber 214 and the source of negative pressure (e.g., the fluid collection device). In other words, the sequestration chamber 214 can be sequestered from the negative pressure source in response to initial volume of bodily fluid filling the sequestration chamber 214.

The initial portion and/or amount of bodily fluid can be any suitable volume of bodily fluid, as described in detail above with reference to the control device 100. For example, in some instances, the initial volume can be associated with and/or at least partially based on an amount or volume of bodily fluid that is sufficient to fully wet or saturate the flow controller 215 (e.g., selectively permeable membrane or member). In other words, in some embodiments, the initial volume of bodily fluid can be a volume sufficient to transition the flow controller 215 to a second state (e.g., a saturated or fully wetted state). In some embodiments, the flow controller 215 is placed in a sealed configuration when transitioned to the second state. That is to say, saturating and/or fully wetting the flow controller 215 (e.g., the semi-permeable material) places the flow controller 215 in a sealed configuration in which the flow controller 215 substantially prevents a flow of a liquid and a gas therethrough.

After the initial volume of bodily fluid is transferred and/or diverted into the sequestration chamber 214, the control device 200 can be transitioned to its second state or operating mode to sequester, segregate, retain, contain, isolate, etc. the initial volume in the sequestration chamber 214. For example, as described above, the flow controller 215 is placed in the sealed configuration, which fluidically isolates the sequestration chamber 214 from the fluid flow path 254. In addition, the transitioning of the flow controller 215 can be in response to the initial amount of bodily fluid filling the sequestration chamber 214. Accordingly, the initial amount of bodily fluid in the sequestration chamber 214 can limit and/or substantially prevent further amounts of bodily fluid from being transferred into the sequestration chamber 214. Thus, the initial amount and/or portion of bodily fluid is sequestered and/or retained within the sequestration chamber 214. As described above, in some instances, contaminants such as, for example, dermally residing microbes or the like dislodged during the venipuncture event, can be entrained and/or included in the initial volume of the bodily fluid and thus, are sequestered in the sequestration chamber 214 when the initial volume of bodily fluid is sequestered therein.

With the flow controller 215 in the second state (e.g., an impermeable or sealed state), the negative pressure otherwise exerted on or through the sequestration chamber 214 is now exerted on or through the fluid flow path 254 and thus, on the flow controller 221. In some instances, a magnitude of the negative pressure can build and/or increase within the fluid flow path 254 until the negative pressure becomes sufficient to transition the flow controller 221 from its first state to its second state. More specifically, when the flow controller 221 is a valve, the negative pressure can increase until it becomes sufficient to overcome the cracking pressure of the valve 221. As such, when the valve is placed in its open state (and/or when the flow controller 221 is otherwise in its second state), the inlet 212 is exposed to the negative pressure differential via the fluid flow path 213. With the fluid collection device fluidically coupled to the outlet 216 and with the control device 200 being in the second state (e.g., the initial volume of bodily fluid is sequestered in or by the sequestration chamber 214), any subsequent volume(s) of the bodily fluid can flow from the inlet 212, through the fluid flow paths 213 and 254, through the flow controller 221 (e.g., valve), through the outlet 216, and into the fluid collection device. Thus, as described above, sequestering the initial volume of bodily fluid in the sequestration chamber 214 prior to collecting or procuring one or more sample volumes of bodily fluid reduces and/or substantially eliminates an amount of contaminants in the one or more sample volumes. Moreover, in some embodiments, the arrangement of the control device 200 can be such that the control device 200 cannot transition to the second state prior to collecting and sequestering the initial volume in the sequestration chamber 214.

Although not shown in FIG. 2, in some embodiments, the control device 200 can include an actuator and/or the like configured to be moved (e.g., via a force applied by a user) between a first state and a second state. In other embodiments, a control device can include any suitable member, device, mechanism, etc. configured to selectively establish fluid communication between two or more fluid flow paths (e.g., the fluid flow paths 213 and 254).

In some instances, it may be desirable to modulate and/or control a magnitude of the negative pressure differential to which the sequestration chamber 214 is exposed. Although not shown in FIG. 2, the device 200 can include one or more means for reducing and/or controlling a magnitude of the negative pressure differential. For example, in some embodiments, the device 200 can include a restricted flow path path(s) or portions of flow path(s) having a smaller diameter than the fluid flow paths 213 and/or 254. For example, in some embodiments, the one or more restricted flow paths can have a diameter of about 1.0 micrometers (μm), about 10.0 μm, about 100.0 μm, about 1000.0 μm, about 10,000.0 μm, about 100,000.0 μm, and/or any suitable diameter therebetween. In other embodiments, the restricted flow path(s) can have a diameter smaller than 1.0 μm or larger than 100,000.0 μm. In such embodiments, a restricted flow path having a smaller diameter may result in a lower magnitude of negative pressure being applied through the sequestration chamber 214 than a magnitude of negative pressure when the restricted flow path has a larger diameter. Moreover, in some such embodiments, the one or more restricted flow paths can be, for example, gas flow path(s) configured to receive a flow of gas or air but not a flow of a liquid (e.g., bodily fluid). In some embodiments, the diameter of the restricted flow path can be sufficiently small to limit and/or prevent a flow of a liquid therethrough.

In some embodiments, the restricted flow path can be, for example, disposed between the junction 218 and the flow controller 215, such that a flow of bodily fluid and/or any other liquid is substantially prevented by the flow controller 215 (e.g., a selectively permeable barrier or seal). More specifically, in some embodiments, the restricted flow path can be disposed between, for example, the flow controller 222 (e.g., valve) and the flow controller 215 (e.g., selectively permeable membrane or member). Accordingly, the flow controller 222 can be exposed to a greater magnitude of negative pressure than the magnitude of negative pressure to which the flow controller 215 is exposed. In such embodiments, the greater magnitude of negative pressure can facilitate the transition of the flow controller 222 from its first state to its second state. For example, in some embodiments, when the flow controller 222 is a valve, this arrangement can allow for the valve to be exposed to a negative pressure differential that is sufficient to overcome the cracking pressure of the valve.

Although the pressure modulation is described above as being based on a diameter of a restricted flow path, it should be understood that this is presented by way of example only and not limitation. For example, in some embodiments, a control device can include any suitable number of restricted flow paths, each of which can have substantially the same diameter or can have varied diameters. For example, in some embodiments, a control device can include up to 100 restricted flow paths or more. In such embodiments, each of the restricted flow paths can have a diameter of between about 1.0 μm and about 100.0 μm, between about 1.0 μm and about 10.0 μm, or between about 1.0 μm and about 5.0 μm. In some embodiments, multiple restricted flow paths can be configured to (1) selectively provide a flow path between the outlet 216 and the sequestration chamber 214 that exposes the sequestration chamber 214 to the negative pressure differential, and (2) act as a flow controller configured to selectively allow the passage of a gas and/or air while substantially preventing the passage of a liquid (e.g., bodily fluid). Other means of modulating the magnitude of negative pressure to which the sequestration chamber is exposed can include, for example, a porous material, a valve, a membrane, a diaphragm, a specific restriction, a vent, a deformable member or flow path, and/or any other suitable means. In some embodiments, the flow controller 215 can be a selectively permeable membrane or member having a predetermined and/or desired porosity to provide the desired amount of negative pressure modulation.

In some embodiments, modulating and/or controlling a magnitude of the pressure to which the sequestration chamber 214 is exposed can, in turn, modulate a magnitude of pressure exerted on the bodily fluid and/or within a vein of a patient. In some instances, such pressure modulation can reduce, for example, hemolysis of a blood sample and/or a likelihood of collapsing a vein. In some instances, the ability to modulate and/or control an amount or magnitude of negative pressure can allow the control device 200 to be used across a large spectrum of patients that may have physiological challenges whereby negative pressure is often needed to facilitate collection of bodily fluid such as, for example, blood (e.g., a pressure differential between atmospheric pressure and a patient's vascular pressure may not be sufficient to facilitate consistent and sufficiently forceful flow) but not so much pressure that a rapid force flattens, collapses, caves-in, and/or otherwise inhibits patency and ability to collect blood.

Figure 3:
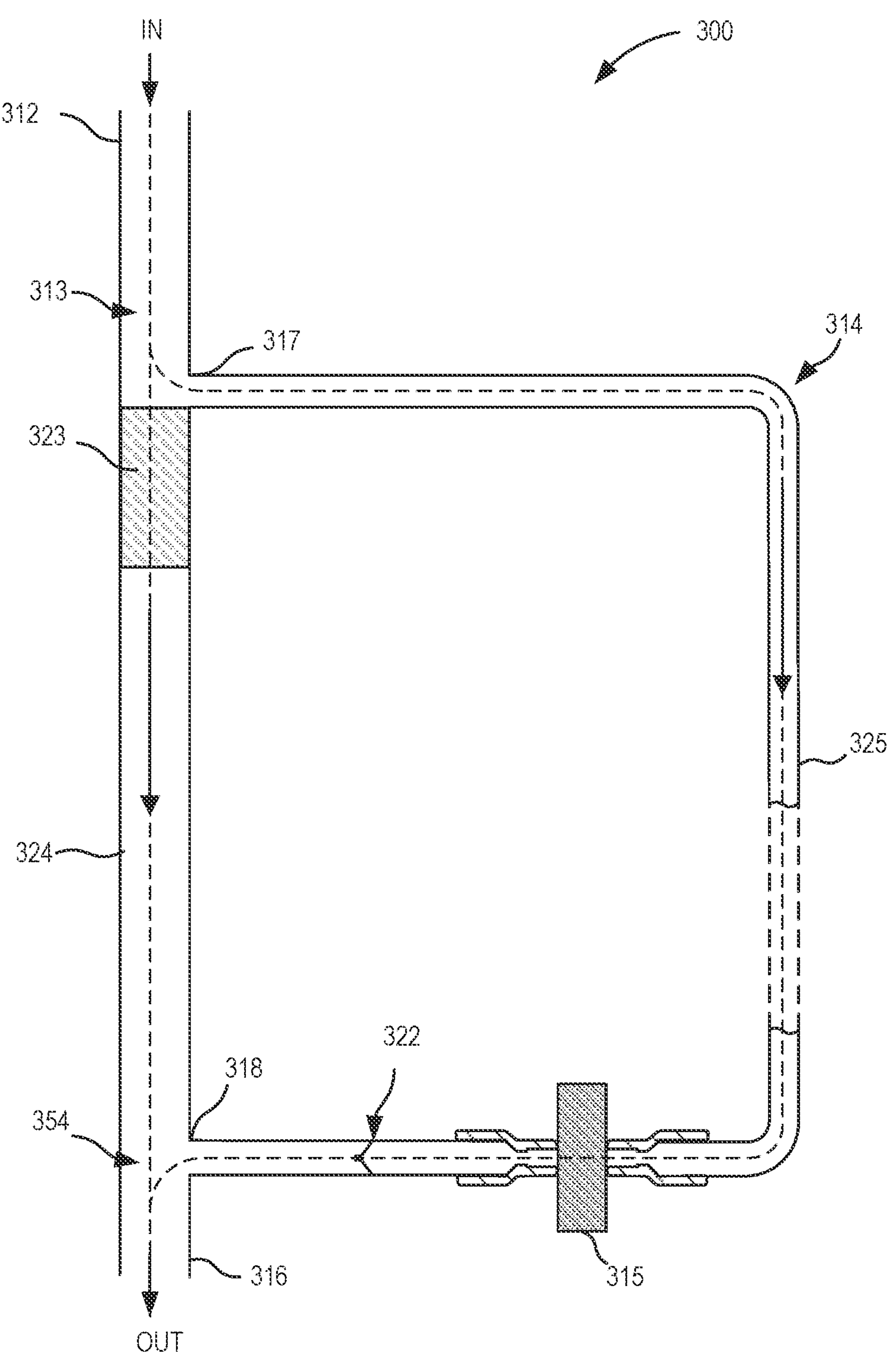
FIG. 3 is a schematic illustration of a fluid control device according to an embodiment.

FIG. 3 illustrates a fluid control device 300 according to another embodiment. The fluid control device 300 (also referred to herein as "control device" or "device") can be of any suitable shape, size, and/or configuration. For example, in some embodiments, the fluid control device 300 can be similar in at least form and/or function to the fluid control device 100 described above with reference to FIG. 1 and/or the fluid control device 200 described above with reference to FIG. 2. Accordingly, portions of the fluid control device 300 that can be similar to portions of the fluid control devices 100 and/or 200 are not described in further detail herein.

As described above with reference to the fluid control device 200 shown in FIG. 2, the fluid control device 300 shown in FIG. 3 includes an inlet 312, an outlet 316, and a sequestration chamber 314. The inlet 312 is configured to be placed in fluid communication with a bodily fluid source to receive a flow of bodily fluid therefrom (e.g., via a lumen-containing device such as a needle, IV catheter, PICC line, or the like). The outlet 316 is configured to be fluidically coupled to a fluid collection device, a syringe, an evacuated container, and/or other intermediary bodily fluid transfer device or vessel (not shown in FIG. 3) such as, for example, a transfer device similar to those described in the '510 publication. Furthermore, the control device 300 includes and/or defines one or more fluid flow paths 313 between the inlet 312 and the sequestration chamber 314 and/or one or more fluid flow paths 354 between the inlet 312 and the outlet 316.

In some embodiments, the device 300 can include a first portion 324 and a second portion 325. As shown in FIG. 3, in some embodiments, the second portion 325 can be, for example, a bypass and/or diversion portion that is physically coupled to and selectively in fluid communication with the first portion 324. Moreover, the device 300 includes and/or forms a first junction 317 at a position where a first end (e.g., an inlet end) of the second portion 325 is coupled to the first portion 324 and includes and/or forms a second junction 318 at a position where a second end (e.g., an outlet end) of the second portion 325 is coupled to the first portion 324. That is to say, the device 300 can be configured to have and/or form a bifurcation (e.g., the second portion 325) at the first junction 317 which is rejoined at, for example, the second junction 318. In some embodiments, the first portion 324 and/or the second portion 325 of the device 300 can include and/or can be formed by flexible tubing or the like having any suitable shape and/or size and being reconfigurable or movable to be placed in any suitable configuration and/or arrangement.

As described in further detail herein, the sequestration chamber 314 is configured to (1) receive a flow and/or volume of bodily fluid from the inlet 312 and (2) sequester (e.g., separate, segregate, contain, retain, isolate, etc.) the flow and/or volume of bodily fluid therein. The sequestration chamber 314 can have any suitable shape, size, and/or configuration. For example, in some embodiments, the sequestration chamber 314 can have any suitable size, volume, and/or fluid capacity such as, for example, those described above with reference to the sequestration chamber 114 and/or 214. In some embodiments, at least a portion of the fluid flow path 313 can extend through a portion of the device 300 to form and/or define at least a portion of the sequestration chamber 314. In some embodiments, the sequestration chamber 314 of the device 300 can be substantially similar in form and/or function to one or more of the sequestration chambers 114 and/or 214. Accordingly, portions of the sequestration chamber 314 may not be described in further detail herein.

As shown in FIG. 3, the sequestration chamber 314 can be formed by and/or included in the second portion 325 of the device 300 and can be selectively placed in fluid communication with (1) the inlet 312 via the fluid flow path 313 and the first junction 317, and (2) the outlet 316 via the fluid flow path 354 and the second junction 318. As such, the sequestration chamber 314 can be configured to (1) selectively receive a flow and/or volume of bodily fluid from the inlet 312 and (2) sequester (e.g., separate, segregate, contain, retain, isolate, etc.) the flow and/or volume of bodily fluid therein.

In some embodiment, the fluid control device 300 can include and/or define one or more flow controllers. Flow controllers can include for example, valves, membranes, diaphragms, restrictors, vents, selectively permeable members (e.g., a fluid impermeable barrier or seal that allows at least selective passage of gas or air such as, for example, a blood barrier like Porex®, and/or the like), ports, etc. (collectively referred to herein as a "flow controller") placed suitably and configured to selectively control (at least in part) a flow of fluids into and/or out of the sequestration chamber 314 and/or any other suitable portion of the device 300. Some embodiments of the device 300, as shown in FIG. 3, can include flow controllers such as a selectively permeable member 315, a check valve 322, and a dissolvable member 323 that are arranged to, under certain states of function and/or under certain conditions, permit, direct, control, and/or obstruct the flow of fluid in one or more specific directions.

As shown in FIG. 3, the second portion 325 of the device 300 can include the check valve 322 and the selectively permeable member 315. For example, in some embodiments, the check valve 322 and/or the selectively permeable member 315 can be disposed on, at, or near a proximal or second end of the sequestration chamber 314. In other words, the check valve 322 and the selectively permeable member 315 can be positioned at, on, or near an outlet or outlet portion of the sequestration chamber 314. Said another way, the check valve 322 and/or the selectively permeable member can be positioned at, on, or near an end portion of the sequestration chamber 314 that is closer to the second junction 318 than it is to the first junction 317. In some embodiments, the check valve 322 and/or the selectively permeable member 315 can be integrated into at least a portion of the second junction 318. In some embodiments, the check valve 322 can be substantially similar to the valve 222 described above with reference to the device 200. For example, in some embodiments, the check valve 322 can be configured to have a desired cracking pressure such as those described above with reference to the valve 222. Accordingly, the check valve 322 can be configured to selectively control a flow of fluid between, for example, the fluid flow path 354 and the sequestration chamber 314, as described above with reference to the device 200. As such, the check valve 322 is not described in further detail herein. Moreover, in some embodiments, the device 300 need not include a check valve and/or any other suitable valve.

The selectively permeable member can be any suitable shape, size, and/or configuration. For example, in some embodiments, the selectively permeable member 315 can be, for example, a membrane, a porous material, an absorbent material, a hydrophilic or hydrophobic material, a selectively permeable barrier, etc. In some embodiments, the selectively permeable member 315 can be substantially similar to the flow controller 215 (e.g., selectively permeable member and/or membrane) and thus, aspects of the selectively permeable member 315 are not described in further detail herein. The selectively permeable member 315 can be configured to at least temporarily allow a gas or air to transfer from the second portion 325 of the device 300 and/or the sequestration chamber 314, through the selectively permeable member 315 and the junction 318, and into the fluid flow path 354 and can be configured to limit and/or substantially prevent a flow of liquid (e.g., bodily fluid) between the second portion 325 and/or the sequestration chamber and the fluid flow path 354 (e.g., via the junction 318). In some embodiments, the selectively permeable member 315 can be in a first or initial state, in which the selectively permeable member 315 allows a flow of air or gas to transfer therethrough, when the device 300 is in its first state and/or configuration. As described in further detail herein, the selectively permeable member 315 can be transitioned to and/or otherwise can be in a second state or configuration, in which the selectively permeable member 315 is substantially impermeable to all fluids (gasses and/or liquids), when the device 300 is in its second state and/or configuration.

In some embodiments, the dissolvable member 323 can be situated at a suitable position within the first portion of the device 300. For example, in some embodiments, the dissolvable member 323 can be positioned at and/or near the first junction 317, as shown in FIG. 3. In some embodiments, the dissolvable member 323 can be integrated into the junction 317 and/or at least a portion of the junction 317. As such, the dissolvable member 323 can be, for example, upstream of the selectively permeable member 315.

As described in further detail herein, the dissolvable member 323 can be configured to transition from a first or initial state to a second state in response to contact with a fluid such as, for example, bodily fluid. In some embodiments, for example, the dissolvable member 323 can be disposed within and/or near the first junction 317 to isolate the inlet 312 from the fluid flow path 354 when the device 300 is in the first or initial state. In response to and/or after transferring an initial volume of bodily fluid to the sequestration chamber 314, the device 300 can be transitioned from the first or initial state to the second state. In some embodiments, when the device 300 is in the second state, the dissolvable member 323 can be substantially dissolved, which in turn, can allow fluid communication to be established between the inlet 312 and the fluid flow path 354. In some instances, for example, a portion of the bodily fluid can contact the dissolvable member 323 as the initial volume of bodily fluid flows into the sequestration chamber 314. The contact with the bodily fluid can, in turn, begin to dissolve the dissolvable member 323 such that when the device 300 is transitioned to its second state and/or configuration, the dissolvable member 323 is at least substantially dissolved, thereby placing the inlet 312 in fluid communication with the fluid flow path 354, as described in further detail herein.

As described above, the device 300 can be used to procure a bodily fluid sample having reduced contamination from microbes such as, for example, dermally residing microbes and/or the like. For example, in some instances, a user such as a doctor, physician, nurse, phlebotomist, technician, etc. can manipulate the device 300 to establish fluid communication between the inlet 312 and the bodily fluid source (e.g., a vein of a patient). Once the inlet 312 is placed in fluid communication with the bodily fluid source (e.g., the portion of the patient), the outlet 316 can be fluidically coupled to the fluid collection device. As described above, in the embodiment shown in FIG. 3, the fluid collection device can be, for example, an evacuated reservoir, a syringe, and/or any container that defines a negative pressure, or is coupled to a downstream source of negative pressure.

Coupling the outlet 316 to the fluid collection device selectively exposes at least a portion of the fluid flow path 354 to the negative pressure within the fluid collection device. The arrangement of the device 300 when in its first or initial state includes one or more flow controllers in their first state or configuration. For example, the selectively permeable member 315, the check valve 322, and the dissolvable member 323 can each be in their first states and/or configurations when the outlet 316 is coupled to the fluid collection device. In response to the negative pressure, the check valve 322 can be configured to transition from a substantially closed state (e.g., its first configuration or state) to a substantially open state (e.g., its second configuration and/or state). For example, in some instances, establishing fluid communication between the outlet 316 and the fluid collection device can expose the check valve 322 to a negative pressure differential that exceeds, for example, a cracking pressure of the check valve 322. Thus, the check valve 322 can be placed in its second state and/or configuration. In other embodiments, the device 300 need not include a check valve and/or other suitable valve. In such embodiments, the negative pressure differential otherwise operable to transition the check valve 322 would instead be exerted on the selectively permeable member 315, which is substantially similar to when the check valve 322 is in the second or opened state.

As described above, the selectively permeable member 315 and the dissolvable member 323 are each in their first state or configuration when the outlet 316 is coupled to the fluid collection device. As such, the selectively permeable member 315 can be configured to permit a flow of air, gas, and/or negative pressure therethrough while blocking and/or preventing a flow of liquid therethrough, as described above with reference to the flow controller 215. Furthermore, with the dissolvable member 323 in its first state or configuration, the dissolvable member 323 can be configured to block, isolate, and/or obstruct fluid communication between, for example, the inlet 312 and the fluid flow path 354 such that it does not permit any flow of fluid (air or liquid or negative pressure) therethrough. Thus, coupling the outlet 316 to the fluid collection device exposes the sequestration chamber 314 to the negative pressure of the fluid collection device, thereby resulting in a negative pressure differential operable in drawing bodily fluid from the bodily fluid source (e.g., the patient), through the inlet 312, and into the sequestration chamber 314.

As described above with reference to the control devices 100 and 200, the arrangement of the device 300 is such that when a volume of bodily fluid is transferred to and/or through the inlet 312, an initial portion of the volume of bodily fluid (also referred to herein as an “initial volume” or a “first volume”) flows from the inlet 312 and into the sequestration chamber 314. That is to say, in some embodiments, the device 300 is in its first or initial state in which the initial portion or volume of bodily fluid can flow from the inlet 312 and into the sequestration chamber 314 in response to the negative pressure differential associated with the fluid collection device. In other words, the negative pressure within the fluid collection device can result in a negative pressure (or negative pressure differential) within at least a portion of the sequestration chamber 314 that is operable in drawing an initial flow of bodily fluid from the inlet 312 into the sequestration chamber 314 when the control device 300 is in the first or initial state. As described in detail above, in some instances, it may be desirable to modulate and/or control a magnitude of the negative pressure differential by any suitable means such as those described herein.

The initial portion and/or amount of bodily fluid can be any suitable volume of bodily fluid, as described in detail above with reference to the control devices 100 and/or 200. For example, in some instances, the initial volume can be associated with and/or at least partially based on an amount or volume of bodily fluid that is sufficient to fully wet or saturate the membrane 315. In other words, in some embodiments, the initial volume of bodily fluid can be a volume sufficient to transition the selectively permeable member 315 to a second state (e.g., a saturated or fully wetted state). As described above with reference to the flow controller 215, the selectively permeable member 315 is placed in a sealed configuration when transitioned to the second state. Thus, transitioning the selectively permeable member 315 to the second state sequesters, blocks, isolates, separates, segregates, and/or otherwise prevents flow through the selectively permeable member 315.

After the initial volume of bodily fluid is transferred and/or diverted into the sequestration chamber 314, the control device 300 can be transitioned to its second state or operating mode to sequester, segregate, retain, contain, isolate, etc. the initial volume in the sequestration chamber 314. As described above, the selectively permeable member 315 is placed in the sealed configuration and thus, substantially prevents a flow of fluid therethrough. In this embodiment, the arrangement of the control device 300 is such that when the selectively permeable member 315 is placed in the sealed configuration, at least a portion of the negative pressure otherwise being exerted through the selectively permeable member 315 is instead exerted on and/or in the fluid flow path 354. The negative pressure, however, can be isolated within the fluid flow path 354 until the dissolvable member 323 is transitioned from its first state and/or configuration to its second state and/or configuration (e.g., until it is at least partially dissolved).

With the selectively permeable member 315 sealed in its second state and the filling of the sequestration chamber 314 to capacity by the initial volume of bodily fluid drawn, the amount of bodily fluid held at least temporarily at and/or near the junction 317 can place a sufficient amount of bodily fluid in contact with the dissolvable member 323 to transition the dissolvable member 323 from its first state to its second state. In other words, filing the sequestration chamber 314 can place a sufficient volume or amount of bodily fluid into contact with the dissolvable member 323 to substantially dissolve the dissolvable member 323, thereby transitioning it to its second state or configuration. The transition of the dissolvable member 323, in turn, is sufficient to transition the fluid control device 300 from its first state to its second state.

With the dissolvable member 323 in its second state and/or configuration (e.g., at least partially dissolved), the negative pressure within the fluid flow path 354 can be exerted on the fluid flow path 313 and/or the inlet 312. In some embodiments, the arrangement of the dissolvable member 323 can be such that as the dissolvable member 323 is dissolved, the inlet 312 is exposed to a greater amount and/or magnitude of negative pressure. In other words, the dissolvable member 323 can be configured to dissolve of a predetermined and/or desired period of time, which in turn, can modulate and/or control an amount of negative pressure to which the inlet 312 is exposed. In some embodiments, the dissolvable member 323 can include one or more characteristics that can be tuned, adjusted, and/or the like configured to adjust (e.g., increase or decrease) a rate at which the dissolvable member 323 transitions to its second state (e.g., dissolves). As the dissolvable member 323 is transitioned to its second state and/or configuration, the negative pressure within the fluid flow path 354, urges, draws, and/or induces a flow of bodily fluid from the inlet 312 and the first junction 317, through the fluid flow path 354 and the outlet 316, and into the fluid collection device. Moreover, the sealed state of the selectively permeable member 315 and the presence of check valves 322 (or other suitable flow controller) can limit and/or substantially prevent flow of bodily fluid from the fluid flow path 354, through the second junction 318, and toward the sequestration chamber 314. In some embodiments, the transitioning of the selectively permeable member 315 and the dissolvable member 323 from their respective first states to their respective second states is operable to sequester and/or retain the initial portion of the bodily fluid in the sequestration chamber 314. As described in further detail herein, in some instances, contaminants such as, for example, dermally residing microbes or the like dislodged during the venipuncture event, can be entrained and/or included in the initial volume of the bodily fluid and thus, are sequestered in the sequestration chamber 314 when the initial volume is sequestered therein.

With the fluid collection device fluidically coupled to the outlet 316 and with the control device 300 in the second state (e.g., the initial volume of bodily fluid is sequestered in or by the sequestration chamber 314), any subsequent volume(s) of the bodily fluid can flow from the inlet 312, through the fluid flow paths 313 and 354, through the outlet 316, and into the fluid collection device. Thus, as described above, sequestering the initial volume of bodily fluid in the sequestration chamber 314 prior to collecting or procuring one or more sample volumes of bodily fluid reduces and/or substantially eliminates an amount of contaminants in the one or more sample volumes. Moreover, in some embodiments, the arrangement of the fluid control device 300 can be such that the device 300 cannot transition to the second state prior to collecting and sequestering the initial volume in the sequestration chamber 314.

FIG. 4 illustrates a fluid control device 400 according to an embodiment. The fluid control device 400 can be of any suitable shape, size, and/or configuration. For example, in some embodiments, the fluid control device 400 can be similar in at least form and/or function to one or more of the devices 100, 200, and/or 300 described above with reference to FIG. 1, FIG. 2, and FIG. 3, respectively. Accordingly, portions of the fluid control device 400 that can be similar to portions of the fluid control devices 100, 200, and/or 300 are not described in further detail herein.

As shown in FIG. 4, the fluid control device 400 (also referred to herein as "control device" or "device") includes an inlet 412, an outlet 416, and a sequestration chamber 414. As described above with reference to the control devices 100, 200, and/or 300, the inlet 412 is configured to be placed in fluid communication with a bodily fluid source to receive a flow of bodily fluid therefrom (e.g., via a lumen-containing device such as a needle, IV catheter, PICC line, and/or the like). The outlet 416 is configured to be fluidically coupled to fluid collection device, a syringe, a transfer adapter, and/or the like (not shown in FIG. 4). Furthermore, the control device 400 includes and/or defines one or more fluid flow paths 413 between the inlet 412 and at least the sequestration chamber 414 and/or one or more fluid flow paths 454 between the inlet 412 and the outlet 416.

In some embodiments, the device 400 can include a first portion 424 and a second portion 425. As shown in FIG. 4, in some embodiments, the second portion 425 can be, for example, a bypass and/or diversion portion that is physically coupled to and selectively in fluid communication with the first portion 424. Moreover, the device 400 includes and/or forms a first junction 417 at a position where a first end (e.g., an inlet end) of the second portion 425 is coupled to the first portion 424 and includes and/or forms a second junction 418 at a position where a second end (e.g., an outlet end) of the second portion 425 is coupled to the first portion 424. That is to say, the device 400 can be configured to have and/or form a bifurcation (e.g., the second portion 425) at the first junction 417 which is rejoined at, for example, the second junction 418. In some embodiments, the first portion 424 and/or the second portion 425 of the device 400 can include and/or can be formed by flexible tubing or the like having any suitable shape and/or size and being reconfigurable or movable to be placed in any suitable configuration and/or arrangement.

The sequestration chamber 414 can have any suitable shape, size, and/or configuration. For example, in some embodiments, the sequestration chamber 414 can have any suitable size, volume, and/or fluid capacity such as, for example, those described above with reference to the sequestration chamber 114. In some embodiments, the sequestration chamber 414 of the device 400 can be substantially similar in form and/or function to one or more of the sequestration chambers 114, 214, and/or 314. Accordingly, portions of the sequestration chamber 414 may not be described in further detail herein.

As shown in FIG. 4, the sequestration chamber 414 can be formed by and/or included in the second portion 425 of the device 400 and can be selectively placed in fluid communication with (1) the inlet 412 via the fluid flow path 413 and the first junction 417, and (2) the outlet 416 via the fluid flow path 454 and the second junction 418. As such, the sequestration chamber 414 can be configured to (1) selectively receive a flow and/or volume of bodily fluid from the inlet 412 and (2) sequester (e.g., separate, segregate, contain, retain, isolate, etc.) the flow and/or volume of bodily fluid therein.

The second portion 425 of the device 400 and/or the sequestration chamber 414 specifically, can include, form, and/or define a flow controller 415 disposed on, at, or near a proximal or second end of the sequestration chamber 414. In other words, the flow controller 415 can be positioned at, on, or near an outlet or outlet portion of the sequestration chamber 414. Said another way, the flow controller can be positioned at, on, or near an end portion of the sequestration chamber 414 that is closer to the second junction 418 than it is to the first junction 417. In some embodiments, the flow controller 415 can be, for example, a membrane, a porous material, an absorbent material, a hydrophilic or hydrophobic material, a selectively permeable barrier, etc. The flow controller 415 can be any suitable shape, size, and/or configuration. In some embodiments, the flow controller 415 can be substantially similar to the flow controller 215 and/or the flow controller 315 and thus, is not described in further detail herein.

As described in detail above, the flow controller 415 is positioned within the second portion 425 of the device to selectively establish fluid communication between the second portion 425 and/or the sequestration chamber 414 and the outlet 416 via the junction 418. Thus, with the flow controller 415 configured to selectively control fluid flow therethrough (e.g., configured as a semi-permeable member), the flow controller 415 can be configured to at least temporarily allow a gas or air to transfer from the second portion 425 of the device 400 and/or the sequestration chamber 414, through the flow controller 415 and the junction 418, and into the fluid flow path 454 and can be configured to limit and/or substantially prevent a flow of liquid (e.g., bodily fluid) between the second portion 425 and/or the sequestration chamber and the fluid flow path 454 (e.g., via the junction 418), as described in further detail herein.

As described above with reference to the devices 100, 200, and/or 300, the device 400 can include one or more flow controllers that is/are configured to selectively control a flow of gas or liquid (e.g., air or bodily fluid, respectively) through the device 400. For example, in the embodiment illustrated in FIG. 4, the device 400 includes a first flow restrictor 431 and a second flow restrictor 432. The flow restrictors 431 and 432 (and/or any other suitable flow controllers that may be included but not illustrated in FIG. 4) can be included at predetermined and/or desired positions along the first portion 424 and/or the second portion 425 of the device 400 to control, manipulate, divert, and/or direct the flow of air, liquid (e.g., bodily fluid), and/or negative pressure. The flow restrictors 431 and 432 can be configured with varying flow permitting or flow obstructing properties. For example, in some embodiments, the flow restrictor 431 and/or the flow restrictor 432 can have and/or can define any suitable inner cross-sectional shape, size, and/or configuration to selectively allow fluid flow therethrough, as described in further detail herein.

In the embodiment shown in FIG. 4, the flow restrictors 431 and 432 each can be a flow restrictor configured to define a flow path therethrough having one or more specific, desired, and/or predetermined characteristics. Moreover, in some embodiments, the second flow restrictor 432 (e.g., the flow restrictor positioned between the second junction 418 and the sequestration chamber 414) can have a flow path that is less restrictive than the flow path of the first flow restrictor 431 (e.g., the flow restrictor positioned between the outlet 416 and the first junction 417). In other words, a pressure differential sufficient to allow fluid (e.g., a gas or liquid) to pass through the second flow restrictor 432 can be less than a pressure differential sufficient to allow fluid (e.g., gas or liquid) to pass through the first flow restrictor 431. Accordingly, the first flow restrictor 431 and the second flow restrictor 431 can be similar to the first valve 221 and second valve 222 described above with reference to FIG. 2.

As described in further detail herein, the arrangement of the flow restrictors 431 and 432 can be such that when a source of negative pressure (e.g., a fluid collection device and/or the like) is coupled to the outlet 416, the negative pressure differential can result in a flow through the second flow restrictor 432 prior to a flow through the first flow restrictor 431. In some instances, this sequential opening of the flow restrictors (e.g., the flow restrictor 432 before the flow restrictor 431), can be operable to direct a flow of fluid (e.g., a first flow) towards the sequestration chamber 414 and then direct the flow of fluid (e.g., a second flow) towards the fluid collection device and/or negative pressure source coupled to the outlet 416. Said another way, in some embodiments, the device 400 can be configured to transition between a first state in which (1) the inlet 412 is placed in fluid communication with the second portion 425 of the device 400 (e.g., the sequestration chamber 414) and (2) the second flow restrictor 432 establishes selective fluid communication between the sequestration chamber 414 and the outlet 416, and a second state in which (1) the second flow restrictor 432 isolates the sequestration chamber 414 from the outlet 416 and (2) the first flow restrictor 431 establishes selective fluid communication between the inlet 412 and the first portion 424 of the device 400 and/or the outlet 416.

As described above, with respect to devices 100, 200, and 300, the device 400 can be used to procure a bodily fluid sample having reduced contamination. In some instances, a user such as a doctor, physician, nurse, phlebotomist, technician, etc. can manipulate the device 400 to establish fluid communication between the inlet 412 and the bodily fluid source (e.g., a vein of a patient). For example, in some embodiments, the user can couple the inlet 412 to an inlet device, a needle, an indwelling catheter or IV, and/or any other suitable lumen-containing device. Once the inlet 412 is placed in fluid communication with the bodily fluid source (e.g., the portion of the patient), the outlet 416 can be fluidically coupled to the fluid collection device. As described herein, the fluid collection device can be any suitable reservoir, syringe, pump, and/or device configured to define and/or produce a negative pressure. In other embodiments, the outlet 416 can be coupled to the fluid collection device, which in turn, is coupled to a downstream source of negative pressure.

The control device 400 can be in a first or initial state prior to coupling the outlet 416 to the fluid collection device. Coupling the outlet 416 to the fluid collection device selectively exposes at least a portion of the fluid flow path 454 to the negative pressure within the fluid collection device. For example, with the device 400 in its initial or first state, the flow controller 415 can be in its first state or configuration such that the flow controller 415 is permeable to a flow of air or gas but impermeable to a flow of liquid (e.g., bodily fluid). Moreover, the arrangement of the flow restrictors 431 and 432 is such that the first flow restrictor 431 is more restrictive toward a flow of liquid or air therethrough than is the second flow restrictor 432.

The negative pressure differential defined and/or produced by the fluid collection device results in a suction or drawing of fluid (e.g., air or gas) from the fluid flow path 454. In other words, the negative pressure within and/or produced by the fluid collection device results in a negative pressure differential within the fluid flow path 454. The arrangement of the flow restrictors 431 and 432, and the flow controller 415 can be such that the negative pressure differential within the fluid flow path 454, results in a negative pressure differential through and/or across the outlet 416, the second junction 418, the second flow restrictor 432, the flow controller 415, and the sequestration chamber 414. Moreover, with the first flow restrictor 431 configured to be more restrictive than the second flow restrictor 432, the flow through the second flow restrictor 432 can at least partially maintain a magnitude of the negative pressure within the fluid flow path 454 below a threshold magnitude of negative pressure otherwise operable to induce a flow of fluid through the first flow restrictor 431. That is to say, when the device 400 is in the first state, the negative pressure within the fluid flow path 454 is sufficient to result in a flow through the second flow restrictor 432 but is insufficient to result in a flow through the first flow restrictor 431. Accordingly, the negative pressure within and/or produced by the fluid collection device (coupled to the outlet 416) can draw air and/or gas through the flow controller 415 and the second flow restrictor 432 and into the fluid flow path 454. Although not shown in FIG. 4, in some embodiments, the device 400 can include a vent or one-way valve configured to allow the air or gas withdrawn from the sequestration chamber 414 to be vented to the atmosphere. In other embodiments, the air and/or gas can be transferred to the fluid collection device, which in turn, can directly or indirectly allow the air or gas to be vented. Thus, the negative pressure within and/or produced by the fluid collection device can result in a negative pressure (or negative pressure differential) within at least a portion of the sequestration chamber 414.

The negative pressure within the sequestration chamber 414 can be operable in drawing an initial flow of bodily fluid from the inlet 412, through the fluid flow path 413 and the first junction 417, and into the sequestration chamber 414 when the control device 400 is in the first or initial state. In some instances, it may be desirable to modulate and/or control a magnitude of the negative pressure differential by any suitable means such as those described herein, including manipulating the permissibility and/or permeability of flow restrictors 431 and/or 432 and/or the flow controller 415. In some embodiments, the flow restrictors 431 and/or 432 can be configured to have one or more external actuators, controllers, and/or adjusters configured to control the amount of flow through the flow restrictors 431 and/or 432 (e.g., by altering or adjusting an inner diameter of the flow restrictors 431 and/or 432). In some other embodiments, the flow restrictors 431 and/or 432 can be configured to adjust and/or alter their properties of permitting fluid flow therethrough based on time, interaction with one or more fluids, and/or any other suitable parameter. In some embodiments, the structure of the flow restrictors 431 and/or 432 can be manipulated (e.g., squeezed, squished, pinched, compressed, etc.) to modulate the degree of negative pressure.

In some embodiments, modulating and/or controlling a magnitude of the pressure to which the sequestration chamber 414 is exposed can, in turn, modulate a magnitude of pressure (i.e., negative pressure) exerted on the bodily fluid and/or within a vein of a patient. In some instances, such pressure modulation can reduce, for example, hemolysis of a blood sample and/or a likelihood of collapsing a vein. In some instances, the ability to modulate and/or control an amount or magnitude of negative pressure can allow the control device 400 to be used across a large spectrum of patients that may have physiological challenges whereby negative pressure is often needed to facilitate collection of bodily fluid such as, for example, blood but not so much pressure that a rapid force flattens, collapses, caves-in, and/or otherwise inhibits patency and ability to collect blood, as described above.

The initial portion and/or amount of bodily fluid can be any suitable volume of bodily fluid, as described in detail above with reference to the control devices 100, 200, and/or 300. For example, in some instances, the initial volume can be associated with and/or at least partially based on an amount or volume of bodily fluid that is sufficient to fully wet or saturate the flow controller 415. In other words, in some embodiments, the initial volume of bodily fluid can be a volume sufficient to transition the flow controller 415 to a second state (e.g., a saturated or fully wetted state or a sealed state), in which the flow controller 415 is placed in a sealed state and/or configuration. In some embodiments, transitioning the flow controller 415 to the second state sequesters, blocks, isolates, separates, segregates, and/or otherwise prevents a flow of air, gas, and/or liquid (e.g., bodily fluid) through the flow controller 415.

After the initial volume of bodily fluid is transferred and/or diverted into the sequestration chamber 414, the control device 400 can be in and/or can be placed in its second state or operating mode to sequester, segregate, retain, contain, isolate, etc. the initial volume in the sequestration chamber 414. As described above, the flow controller 415 in its second state or sealed state substantially prevents a flow of fluid including air and liquid therethrough (e.g., and into the second flow restrictor 432 and/or fluid flow path 454). Therefore, the sequestration chamber 414 is fluidically isolated from the fluid collection device and/or source of negative pressure, which in turn, can allow a pressure differential between the sequestration chamber 414 and, for example, the inlet 412 to equalize such that the flow of bodily fluid to the sequestration chamber 414 is limited and/or substantially stops.

As described previously, an amount of negative pressure sufficient to induce and/or allow a flow of fluid through the first flow restrictor 431 can be greater than an amount of negative pressure sufficient to induce and/or allow a flow of fluid through the second flow restrictor 432. In this embodiment, the arrangement of the control device 400 is such that when the flow controller 415 is placed in the second or sealed configuration, at least a portion of the negative pressure otherwise being exerted through the flow controller 415 builds and/or increases within the fluid flow path 454 to an extent sufficient to induce and/or allow a flow of fluid through the first flow restrictor 431. Thus, with the device 400 in its second state, the negative pressure exerted by the fluid collection device and/or negative pressure source can result in negative pressure within the fluid flow path 454 sufficient to allow bodily fluid to flow from the inlet 412, through the first flow restrictor 431, the fluid flow path 454, and the outlet 416, and into the fluid collection device. As described above, in some instances, contaminants such as, for example, dermally residing microbes or the like dislodged during the venipuncture event, can be entrained and/or included in the initial volume of the bodily fluid and thus, are sequestered in the sequestration chamber 414. Moreover, as described for devices 100, 200, 300, in some embodiments, the arrangement of the fluid control device 400 can be such that the device cannot transition to the second state prior to collecting and sequestering the initial volume in the sequestration chamber 414.

While the flow restrictors 431 and 432 are particularly described above with reference to FIG. 4, in other embodiments, a fluid control device can include other forms of flow controllers and/or restrictors in addition to and/or instead of those described in association with device 400. In some embodiments, a fluid control device can include any other suitable means or combination of means for controlling fluid flow therethrough. For example, FIGS. 5-7 illustrate three different embodiments of flow controllers and/or flow restrictors, each according to a different embodiment. FIG. 5 shows a flow restrictor 433 defining an orifice or channel for the passage of air and/or fluid. In this embodiment, the fluid restrictor 433 can have a relatively large inner diameter and a relatively long length. FIG. 6, on the other hand, shows a flow restrictor 434 defining an orifice or channel having a relatively small inner diameter (e.g., smaller than the inner diameter of the flow restrictor 433) and a relatively short length (e.g., shorter than the length of the flow restrictor 433).

As will be understood, adjusting a length and/or diameter of an orifice or channel of a flow restrictor can allow for an adjusting of a magnitude of a pressure differential sufficient to induce and/or result in a flow of fluid (e.g., bodily fluid) through the orifice or channel. For example, in some embodiments, a flow restriction and/or a restricted flow path can have a diameter of about 1.0 micrometers (μm), about 10.0 μm, about 100.0 μm, about 1000.0 μm, about 10,000.0 μm, about 100,000.0 μm, and/or any suitable diameter therebetween. In other embodiments, the restricted flow path can have a diameter smaller than 1.0 μm or larger than 100,000.0 μm. In such embodiments, a restricted flow path having a smaller diameter may be designed such that a magnitude of a pressure (e.g., negative pressure) sufficient to induce or draw a flow of fluid through the restricted flow path is greater than a magnitude of a pressure sufficient to induce or draw a flow of fluid through a restricted flow path having a larger diameter. Similarly, a longer restricted flow path may be designed such that a magnitude of a pressure (e.g., negative pressure) sufficient to induce or draw a flow of fluid through the restricted flow path is greater than a magnitude of a pressure sufficient to induce or draw a flow of fluid through a restricted flow path having a shorter length.

FIG. 7 shows a flow controller 435 including a porous material 436 disposed within the flow controller 435. In such embodiments, a porosity and/or permeability of the porous material 436 can be adjusted to adjust a magnitude of a pressure differential sufficient to induce and/or result in a flow of fluid (e.g., bodily fluid) through the orifice or channel. Other examples of flow restrictors and/or flow controllers can include but are not limited to, flow controllers where the restricted or restrictive regions include regions with varying diameter of the cross-section permitting fluid flow or include structures (e.g., porous material) designed to selectively allow or deter fluid flow or air flow as desired. Other embodiments can include, for example, valves, actuators, selectively permeable membranes and/or materials, and/or the like.

Figure 8:
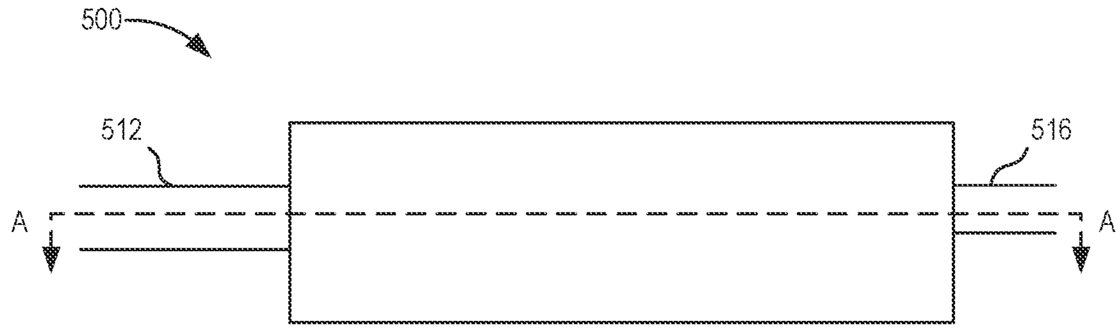
FIG. 8 is a schematic illustration of a fluid control device according to an embodiment.
Figure 9:
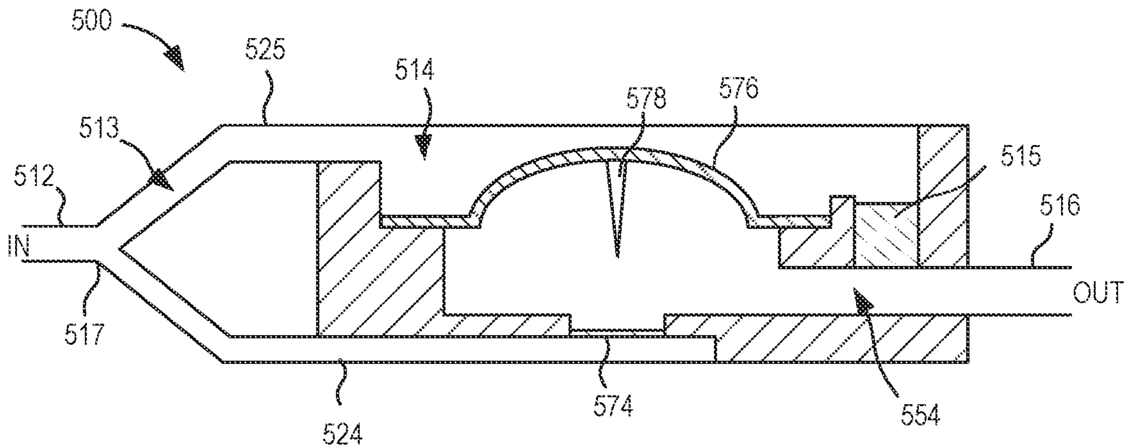
FIGS. 9 and 10 are schematic cross-sectional illustrations of the fluid control device illustrated in FIG. 8, taken along the line A-A, and shown in a first state and a second state, respectively.
Figure 10:
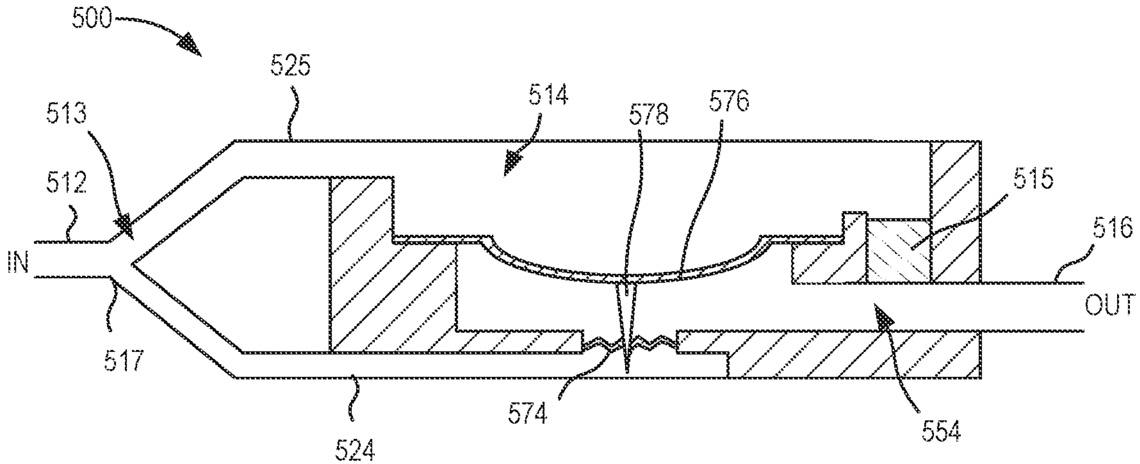

FIGS. 8-10 illustrate a fluid control device 500 according to an embodiment. FIG. 8 shows, for example, a top view of the device 500 and FIGS. 9 and 10 each show a cross-sectional view of the device 500, in a first state and a second state, respectively. The fluid control device 500 can be similar in at least form and/or function to any of the fluid control devices 100, 200, 300, and/or 400. Accordingly, portions of the fluid control device 500 that can be similar to portions of the fluid control devices 100, 200, 300, and/or 400 are not described in further detail herein.

As shown in FIGS. 8-10, the fluid control device 500 (also referred to herein as "control device" or "device") includes an inlet 512 and an outlet 516, and a sequestration chamber 514. As described above with reference to the control devices 100, 200, 300, and/or 400, the inlet 512 is configured to be placed in fluid communication with a bodily fluid source to receive a fluid of bodily fluid therefrom (e.g., via a lumen-containing device such as a needle or the like). The outlet 516 is configured to be fluidically coupled to a fluid collection device (not illustrated). The inlet 512, the outlet 516, and the fluid collection device can be substantially similar to those described above and thus, are not described in further detail herein.

As described above, the control device 500 is configured to (1) receive an initial flow and/or volume of bodily fluid via the inlet 512 and (2) sequester (e.g., separate, segregate, contain, retain, isolate, etc.) the flow and/or volume of bodily fluid within the sequestration chamber 514. The device 500 can be any suitable shape, size, and/or configuration. In some embodiments, the device 500 can have a size that is at least partially based on a volume of bodily fluid at least temporarily stored, for example, in the sequestration chamber 514. For example, in the embodiment shown in FIGS. 8-10, the device 500 can be arranged in and/or can have a substantially "inline" configuration in which portions of the device 500 are at least partially aligned.

The device 500 includes and/or defines one or more fluid flow paths 513 between the inlet 512 and at least the sequestration chamber 514 and/or one or more fluid flow paths 554 between the inlet 512 and the outlet 516. In some embodiments, the device 500 can include a first portion 524 and a second portion 525. As shown in FIGS. 9 and 10, in some embodiments, the second portion 525 can be, for example, a bypass and/or diversion portion that is physically coupled to and selectively in fluid communication with the first portion 524. Moreover, the device 500 includes and/or forms a junction 517 at a position where each of a first end (e.g., an inlet end) of the first portion 524 and a first end (e.g., an inlet end) of the second portion 525 couple to the inlet 512. In some embodiments, the first portion 524 and the second portion 525 can be collectively disposed in a housing or otherwise at least partially enclosed by a common structure. In other embodiments, the first portion 524 and/or the second portion 525 of the device 500 can include and/or can be formed by flexible tubing or the like having any suitable shape and/or size and being reconfigurable or movable to be placed in any suitable configuration and/or arrangement.

The sequestration chamber 514 can have any suitable shape, size, and/or configuration. For example, in some embodiments, the sequestration chamber 514 can have any suitable size, volume, and/or fluid capacity such as, for example, those described above with reference to the sequestration chamber 114. The sequestration chamber 514 can be formed by and/or included in the second portion 525 of the device 500 and can be selectively placed in fluid communication with (1) the inlet 512 via the fluid flow path 513 and the first junction 517, and (2) the outlet 516 via the fluid flow path 554 and a flow controller 515 (described in further detail herein). In some embodiments, the sequestration chamber 514 of the device 500 can be substantially similar in form and/or function to one or more of the sequestration chambers 114, 214, 314, and/or 414. Accordingly, portions of the sequestration chamber 514 may not be described in further detail herein.

As shown in FIGS. 9 and 10, the second portion 525 of the device 500 and/or the sequestration chamber 514 specifically, can include, form, and/or define the flow controller 515 disposed on, at, or near a proximal or second end of the sequestration chamber 514. In other words, the flow controller 515 can be positioned at, on, or near an outlet or outlet portion of the sequestration chamber 514 to establish selective fluid communication between the sequestration chamber 514 and the fluid flow path 554. The flow controller 515 can be any suitable shape, size, and/or configuration. In some embodiments, the flow controller 515 can be, for example, a membrane, a porous material, an absorbent material, a hydrophilic or hydrophobic material, a selectively permeable barrier, etc. In some embodiments, the flow controller 515 can be configured to at least temporarily allow a gas or air to transfer from the second portion 525 of the device 500 and/or the sequestration chamber 514, through the flow controller 515, and into the fluid flow path 554 and can be configured to limit and/or substantially prevent a flow of liquid (e.g., bodily fluid) between the second portion 525 and/or the sequestration chamber 514 and the fluid flow path 554. In some embodiments, the flow controller 515 can be substantially similar in at least form and/or function to the flow controllers 215, 315, and/or 415 and thus, aspects of the flow controller 515 are not described in further detail herein.

In some embodiments, the device 500 can include one or more flow controllers in addition to the flow controller 515 configured to selectively control, direct, divert, and/or manipulate fluid flow through at least a portion of the flow paths 513 and/or 554. In some embodiments, such flow controllers can be configured to selectively control a flow of fluid through the device 500 in response to, for example, an external force or actuation (e.g., manual intervention by the user), or automatically (e.g., after a period of time and/or in response to a predetermined force, pressure, flow rate, volume of fluid, saturation level, etc. For example, in this embodiment, the device 500 includes a diaphragm 576 movably disposed within the body of the device 500 and configured to at least partially define the sequestration chamber 514. In some embodiments, the diaphragm 576 can be configured to transition, flip, move, switch, deform, etc., from a first configuration or state (FIG. 9) to a second configuration or state (FIG. 10) in response to a negative pressure differential within and/or across at least a portion of the device 500 (e.g., a negative pressure differential associated with and/or resulting from the coupling of the fluid collection device to the outlet 516).

In some embodiments, the diaphragm 576 can be coupled to a piercing member 578 and configured to move through at least a portion of the device 500 in response to movement of the diaphragm 576. As shown in FIGS. 9 and 10, the device 500 includes a film, barrier, and/or frangible member 574 (referred to herein as "barrier") configured to at least temporarily isolate, separate, and/or sequester the fluid flow path 513 (e.g., an inlet fluid flow path) from the fluid flow path 554 (e.g., an outlet fluid flow path). In some embodiments, the arrangement of the diaphragm 576 and/or the piercing member 578 can be such that as the diaphragm 576 is transitioned from its first state, configuration, and/or position to its second state, configuration, and/or position, the piercing member 578 is transitioned and/or moved through a portion of the device 500 to pierce, puncture, rupture, break, and/or otherwise reconfigure the barrier 574.

More specifically, as shown in FIG. 9, the diaphragm 576 can have, for example, a concave shape relative to the barrier 574 when in its first or initial state and the piercing member 578 coupled to the diaphragm 576 is disengaged with and/or separated from the barrier 574. As such, the barrier 574 can be in a first or initial state in which the barrier 574 is sealed, unbroken, not punctured, and/or otherwise acting to fluidically isolate the fluid flow path 513 from the fluid flow path 554. As shown in FIG. 10, the diaphragm 576 can have, for example, a convex shape relative to the barrier 574 when in its second or subsequent state and the piercing member 578 coupled to the diaphragm 576 is engaged with, in contact with, and/or otherwise reconfiguring the barrier 574, thereby piercing through and/or defining an opening through the barrier 574. In other words, as illustrated in FIGS. 9 and 10 respectively, the device 500 and/or the diaphragm 576 is configured to move between a first or initial state in which the fluid flow path 513 is fluidically isolated and/or sequestered from the fluid flow path 554 such that a flow of fluid (e.g., bodily fluid) can flow from the inlet 512, through at least a portion of the fluid flow path 513, and into the sequestration chamber 514, and a second or subsequent state in which the fluid flow path 513 is in fluid communication with the fluid flow path 554 such that a flow of fluid (e.g., bodily fluid) can flow from the inlet 512, through the barrier 574 and the fluid flow path 554, and to the outlet 516. In some embodiments, the transitioning of the device 500 and/or diaphragm 576 from the first state to the second state can be such that a volume of the device 500 defined between the diaphragm 576, the flow controller 515, and the one or more walls of the sequestration chamber 514 is increased (i.e., a volume of the sequestration chamber 514 is increased), which in turn, results in a negative pressure therein that can be operable in drawing at least a portion of the initial volume of bodily fluid through the inlet 512 and into the sequestration chamber 514, as described further below.

As described above, with respect to devices 100, 200, 300, and/or 400, the device 500 can be used to procure a bodily fluid sample having reduced contamination. For example, in some instances, the control device 500 can be in the first or initial state and a user can manipulate the device 500 to establish fluid communication between the inlet 512 and the bodily fluid source (e.g., a vein of a patient) and to establish fluid communication between the outlet 516 and the fluid collection device (e.g., a sample vessel, syringe, reservoir, etc.). With the device 500 in its initial or first state, coupling the outlet 516 to the fluid collection device selectively exposes at least a portion of the fluid flow path 554 to the negative pressure within the fluid collection device. Moreover, when the device 500 is in its initial or first state, the flow controller 515 can be in its first state or configuration such that the flow controller 515 is permeable to a flow of air or gas but impermeable to a flow of liquid (e.g., bodily fluid). The barrier 574 is also in its first or initial state such that the barrier 574 fluidically isolates the fluid flow path 513 from the fluid flow path 554. As such, the negative pressure differential defined and/or produced by the fluid collection device results in a suction force within the fluid flow path 554, which in turn, is exerted on or through the flow controller 515. Thus, coupling the outlet 516 to the fluid collection device exposes the sequestration chamber 514 to the negative pressure defined and/or produced by the fluid collection device, thereby resulting in a negative pressure differential operable in drawing the initial volume and/or amount of bodily fluid from the bodily fluid source (e.g., the patient's vasculature), through the inlet 512, at least a portion of the fluid flow path 513, and the junction 517, and into the sequestration chamber 514. Although not shown in FIGS. 8-10, in some embodiments, the device 500 can include any suitable device and/or mechanism configured to modulate the negative pressure to which the sequestration chamber 514 is exposed, as described in detail above.

The initial portion and/or amount of bodily fluid can be any suitable volume of bodily fluid, as described in detail above with reference to the control devices 100, 200, 300, and/or 400. For example, in some instances, the initial volume can be associated with and/or at least partially based on an amount or volume of bodily fluid that is sufficient to fully wet or saturate the flow controller 515 (e.g., transition the flow controller 515 from its first or selectively open state to its second or sealed state). With the flow controller 515 in its second state or sealed state, the flow controller 515 substantially prevents a flow of fluid including air and liquid therethrough, thereby sequestering and/or fluidically isolating the sequestration chamber 514 from the fluid flow path 554. As a result, in some instances, a pressure differential between, for example, the sequestration chamber 514 and the inlet 512 can equalize such that the flow of bodily fluid to the sequestration chamber 514 is limited and/or substantially stops.

In this embodiment, the arrangement of the control device 500 is such that when the flow controller 515 is placed in the second or sealed configuration, at least a portion of the negative pressure otherwise being exerted through the flow controller 515 builds and/or increases within the fluid flow path 554 to an extent sufficient to transition the diaphragm 576 from its first state or configuration (FIG. 9) to its second state or configuration (FIG. 10). In some embodiments, for example, the diaphragm 576 can flip and/or can be moved from a concave configuration relative to the barrier 574 to a convex configuration relative to the barrier 574. Moreover, as described above, the transitioning of the diaphragm 576, in turn, moves the piercing member 578 such that the piercing member 578 engages, pierces, punctures, opens, breaks, and/or otherwise reconfigures the barrier 574, thereby placing the fluid flow path 513 in fluid communication with the fluid flow path 554. Thus, with the device 500 in its second state, the negative pressure exerted by the fluid collection device and/or negative pressure source can result in negative pressure within the fluid flow path 554 sufficient to allow bodily fluid to flow from the inlet 512, through the fluid flow path 513, barrier 574, fluid flow path 554, and outlet 516, and into the fluid collection device.

As described above, in some instances, contaminants such as, for example, dermally residing microbes or the like dislodged during the venipuncture event, can be entrained and/or included in the initial volume of the bodily fluid and thus, are sequestered in the sequestration chamber 514. Moreover, as described for devices 100, 200, 300, and/or 400, in some embodiments, the arrangement of the fluid control device 500 can be such that the device cannot transition to the second state prior to collecting and sequestering the initial volume in the sequestration chamber 514.

Figure 11:
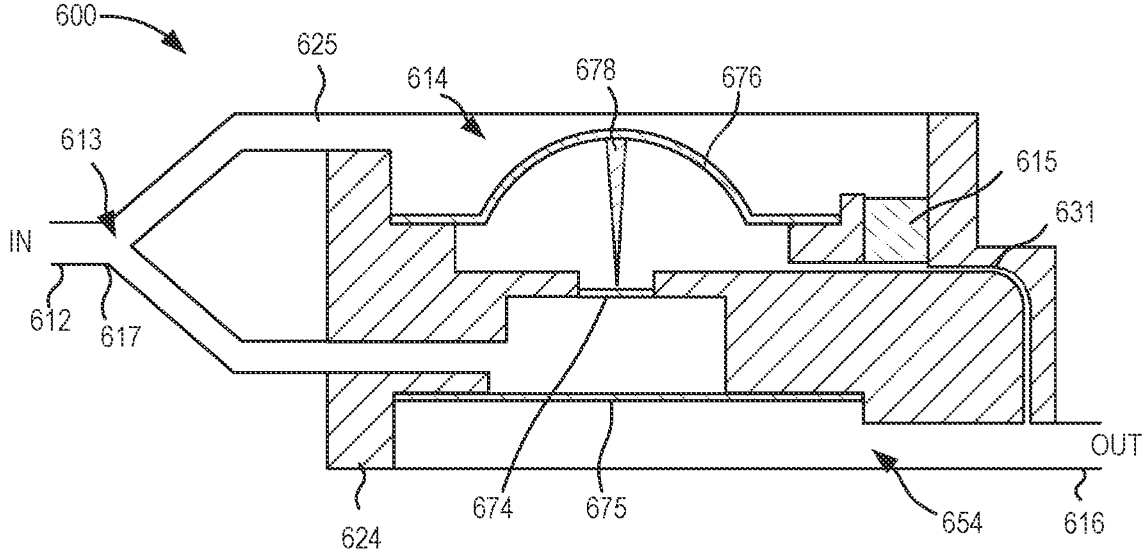
FIGS. 11 and 12 are schematic cross-sectional illustrations of a fluid control device in a first state and a second state, respectively, according to an embodiment.
Figure 12:
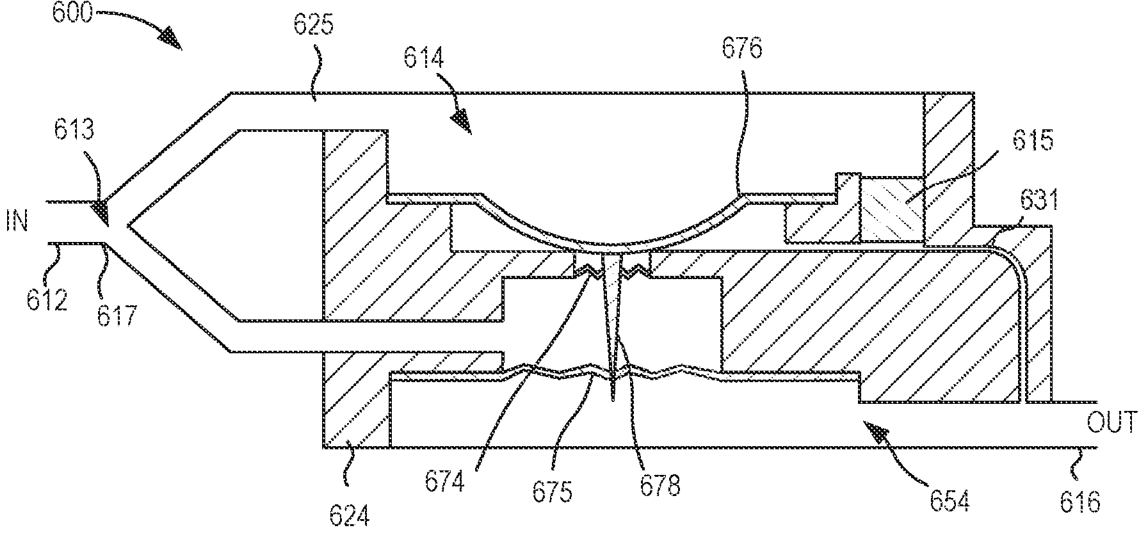

While the flow controller 515 is shown in FIGS. 8-10 as being in fluid communication with the fluid flow path 554 without a feature, device, mechanism, and/or means to modulate an amount of negative pressure disposed therebetween, in other embodiments, a fluid control device can include any suitable feature, device, mechanism, and/or means configured to modulate an amount or magnitude of negative pressure to which a flow controller is exposed. For example, FIGS. 11 and 12 are schematic illustrations of a fluid control device 600 in a first state and a second state, respectively, according to another embodiment. The fluid control device 600 (also referred to herein as "control device" or "device") can be any suitable shape, size, and/or configuration. For example, in some embodiments, the device 600 can be substantially similar in at least form and/or function to any of the devices 100, 200, 300, 400, and/or 500 described herein. More particularly, the device 600 can be substantially similar in at least form and/or function to the device 500 described above with reference to FIGS. 8-10. Accordingly, portions and/or aspects of the fluid control device 600 are not described in further detail herein.

As shown in FIGS. 11 and 12, the device 600 includes an inlet 612, an outlet 616, and a sequestration chamber 614. In addition, the device 600 includes and/or defines one or more fluid flow paths 613 between the inlet 612 and at least the sequestration chamber 614 and/or one or more fluid flow paths 654 between the inlet 612 and the outlet 616. The inlet 612 is configured to be placed in fluid communication with a bodily fluid source to receive a fluid of bodily fluid therefrom. The outlet 616 is configured to be fluidically coupled to a fluid collection device substantially similar to those described above. The sequestration chamber 614 can be included in and/or formed by a portion of the device 600 and can be selectively placed in fluid communication with (1) the inlet 612 via the fluid flow path 613, and (2) the outlet 616 via the fluid flow path 654 and a flow controller 615. The flow controller 615 can be any suitable shape, size, and/or configuration and can be configured to selectively control, permit, allow, and/or transfer a flow of fluid therethrough. For example, as described above, the flow controller 615 can be a selectively permeable member configured to be selectively permeable to a gas (e.g., air) and substantially impermeable to a liquid (e.g., bodily fluid). In some embodiments, the inlet 612, the outlet 616, the sequestration chamber 614, and the flow controller 615 can be substantially similar to the inlet 512, the outlet 516, the sequestration chamber 514, and the flow controller 515, respectively, described above with reference to the device 500 shown in FIGS. 8-10. Accordingly, portions and/or aspects of the inlet 612, the outlet 616, the sequestration chamber 614, and/or the flow controller 615 are not described in further detail herein.

In some embodiments, the device 600 can include a first portion 624 and a second portion 625. As shown in FIGS. 11 and 12, in some embodiments, the second portion 625 can be, for example, a bypass and/or diversion portion that (1) is physically coupled to and selectively in fluid communication with the first portion 624 and (2) includes and/or forms the sequestration chamber 614. Moreover, the device 600 includes and/or forms a junction 617 at a position where each of a first end (e.g., an inlet end) of the first portion 624 and a first end (e.g., an inlet end) of the second portion 625 couple to the inlet 612. In some embodiments, the first portion 624 and the second portion 625 can be collectively disposed in a housing or otherwise at least partially enclosed by a common structure. In other embodiments, the first portion 624 and/or the second portion 625 of the device 600 can include and/or can be formed by flexible tubing or the like having any suitable shape and/or size and being reconfigurable or movable to be placed in any suitable configuration and/or arrangement.

As described above with reference to the device 500, the device 600 includes a diaphragm 676 movably disposed within at least a portion of the device 600 and a piercing member 678 coupled to the diaphragm 676. In some embodiments, the diaphragm 676 can define at least a portion of the sequestration chamber 614. In some embodiments, the diaphragm 676 and the piercing member 678 can be substantially similar in at least form and/or function to the diaphragm 576 and piercing member 578, respectively, of the device 500. For example, as described above with reference to the diaphragm 576 of the device 500, the diaphragm 676 is configured to transition between a first state, in which the fluid flow path 613 is fluidically isolated from the fluid flow path 654, and a second state, in which the fluid flow path 613 is in fluid communication with the fluid flow path 654, as described in further detail herein.

While the device 500 is shown and described above as including a single barrier 574 configured to selectively isolate and/or otherwise selectively prevent fluid communication between the fluid flow paths 513 and 554, in the embodiment shown in FIGS. 11 and 12, the device 600 includes a set of barriers configured to selectively prevent or selectively allow fluid flow through the device 600. For example, in some embodiments, the device 600 can include two barriers 674 and 675. Each of the barriers 674 and 675 can be substantially similar in at least form and/or function to the barrier 574 of the device 500 described above with reference to FIGS. 9 and 10. Accordingly, the arrangement of the device 600 can be such that when the diaphragm 676 is in its first state, the piercing member 678 can be disengaged and/or separated from the barriers 674 and 675, which in turn, remain in a sealed, closed, and/or substantially undeformed state (FIG. 11). As the diaphragm 676 is transitioned to its state, however, the piercing member 678 can be moved within the device 600 such that the piercing member 678 engages, contacts, pierces, punctures, and/or otherwise reconfigures each of the barriers 674 and 675, thereby transitioning the barriers 674 and 675 to an unsealed, opened, pierced, and/or deformed state (FIG. 12), as described in further detail herein.

As described above, the device 600 can include one or more features, mechanisms, devices, and/or means of modulating a negative pressure exerted through one or more portions of the device 600. For example, as shown in FIGS. 11 and 12, the device 600 includes and/or defines a restricted flow path 631 (also referred to herein as a "flow restrictor") configured to establish fluid communication between, for example, the flow controller 615 and the fluid flow path 654. As described above with reference to the flow restrictors 431 and 432 of the device 400 shown in FIG. 4, the flow restrictor 631 can be configured to define a restricted and/or limited flow path therethrough having one or more specific, desired, and/or predetermined characteristics. As described in further detail herein, the arrangement of the flow restrictor 631 can be such that when a source of negative pressure (e.g., a fluid collection device and/or the like) is coupled to the outlet 616, a negative pressure differential can result in a restricted and/or modulated flow or suction force through the flow restrictor 631, which in turn, results in a restricted and/or modulated negative pressure being exerted on the flow controller 615. Accordingly, the flow restrictor 631 can be substantially similar in at least form and/or function to the flow restrictor 432 described above with reference to FIG. 4.

As described above with respect to devices 100, 200, 300, 400, and/or 500, the device 600 can be used to procure a bodily fluid sample having reduced contamination. For example, in some instances, the control device 600 can be in the first or initial state (see e.g., FIG. 11) and a user can manipulate the device 600 to establish fluid communication between the inlet 612 and the bodily fluid source (e.g., a vein of a patient) and to establish fluid communication between the outlet 616 and the fluid collection device (e.g., a sample vessel, syringe, reservoir, etc.). With the control device 600 in its first or initial state, coupling the outlet 616 to the fluid collection device selectively exposes at least a portion of the fluid flow path 654 to the negative pressure within the fluid collection device. When the control device 600 is in the first state, the diaphragm 676, the flow controller 615, and the barriers 674 and 675 each can be in their respective first states. Accordingly, the diaphragm 676 can be disposed in a position and/or state such that the piercing member 678 is separated and/or disengaged from the barriers 674 and 675. As such, the barriers 674 and 675 are in their first or sealed state such that the barrier 674 (e.g., a first barrier) fluidically isolates and/or sequesters the fluid flow path 613 from the flow restrictor 631 (e.g., restricted flow path) and such that the barrier 675 (e.g., a second barrier) fluidically isolates and/or sequesters the fluid flow path 613 (e.g., an inlet flow path) from the fluid flow path 654 (e.g., an outlet flow path), as shown in FIG. 11.

With the fluid collection device coupled to the outlet 616, the negative pressure within the fluid collection device can result in a negative pressure (or negative pressure differential) within at least a portion of the fluid flow path 654. As shown in FIG. 11, however, the barrier 675 fluidically isolates at least a portion of the fluid flow path 654 from other portions of the device 600 and thus, the negative pressure within the fluid flow path 654 is transferred and/or exerted through the flow restrictor 631. Accordingly, a modulated and/or desired portion of the negative pressure within and/or produced by the fluid collection device (coupled to the outlet 616) is transferred through the flow restrictor 631 and in turn, exerted on the flow controller 615. Moreover, with the flow controller 615 in its first state (e.g., a selectively permeable state), the modulated and/or desired portion of the negative pressure within and/or produced by the fluid collection device can result in a negative pressure (or negative pressure differential) within at least a portion of the sequestration chamber 614 that is operable in drawing an initial flow of bodily fluid from the inlet 612, through at least a portion of the fluid flow path 613, and into the sequestration chamber 614, as described above with reference to, for example, the devices 100, 200, 300, 400, and/or 500.

The initial portion and/or amount of bodily fluid can be any suitable volume of bodily fluid, as described in detail above with reference to the control devices 100, 200, 300, 400, and/or 500. For example, in some instances, the initial volume can be associated with and/or at least partially based on an amount or volume of bodily fluid that is sufficient to fully wet or saturate the flow controller 615 (e.g., transition the flow controller 615 from its first or selectively open state to its second or sealed state). With the flow controller 615 in its second or sealed state, the flow controller 615 substantially sequesters, blocks, isolates, separates, segregates, and/or otherwise prevents a flow of fluid (e.g., gas and liquid) through the flow controller 615, thereby sequestering and/or fluidically isolating the sequestration chamber 614 from the fluid flow path 654. As a result, in some instances, a pressure differential between, for example, the sequestration chamber 614 and the inlet 612 can equalize such that the flow of bodily fluid to the sequestration chamber 614 is limited and/or substantially stops.

As described above with reference to the device 500, the arrangement of the control device 600 is such that when the flow controller 615 is placed in its second or sealed state, at least a portion of the negative pressure otherwise being exerted through the flow controller 615 is instead exerted on a concave side or surface of the diaphragm 676. The increased negative pressure on the concave side and/or surface of the diaphragm 676 can be operable to flip, switch, and/or transition the diaphragm 676 from its first state (e.g., a concave state relative to the barrier 674) to its second state (e.g., a convex state relative to the barrier 674). In some embodiments, the flow restrictor 631 can be configured to modulate and/or regulate a magnitude or change in magnitude of the negative pressure being exerted on the diaphragm 676 in substantially the same manner as the modulation and/or regulation of the negative pressure being exerted on or through the flow controller 615. In some instances, modulating the negative pressure exerted on the diaphragm 676 can in turn, modulate, reduce, and/or control a rate at which the diaphragm 676 is transitioned from its first state to its second state.

As described above, the transitioning of the diaphragm 676, in turn, moves the piercing member 678 coupled thereto such that the piercing member 678 engages, pierces, punctures, opens, breaks, and/or otherwise reconfigures each of the barriers 674 and 675 such that each barrier 674 and 675 is placed in an open state and/or otherwise defines an opening through which fluid can flow. In other embodiments, the barrier 674 can be configured to form a substantially fluid tight seal with an outer surface of the piercing member 678 as the piercing member 678 extends therethrough. Moreover, as described above with reference to the device 500, the opening of the barrier 675 places the fluid flow path 613 in fluid communication with the fluid flow path 654. As such, the device 600 can be in and/or can be placed in its second state, and the negative pressure exerted by the fluid collection device and/or negative pressure source can result in negative pressure within the fluid flow path 654 sufficient to allow bodily fluid to flow from the inlet 612, through the fluid flow path 613, barrier 675, fluid flow path 654, and outlet 616, and into the fluid collection device (not shown). As described above, in some instances, contaminants such as, for example, dermally residing microbes or the like dislodged during the venipuncture event, can be entrained and/or included in the initial volume of the bodily fluid and thus, are sequestered in the sequestration chamber 614. Moreover, as described for devices 100, 200, 300, 400, and/or 500, in some embodiments, the arrangement of the fluid control device 600 can be such that the device cannot transition to the second state prior to collecting and sequestering the initial volume in the sequestration chamber 614.

Figure 13:
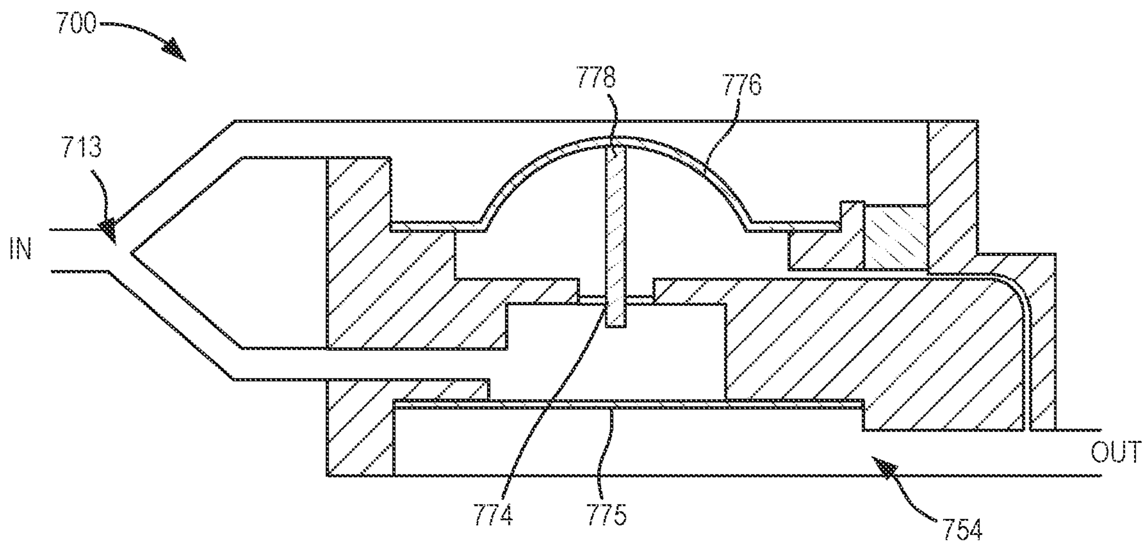
FIGS. 13 and 14 are schematic cross-sectional illustrations of a fluid control device in a first state and a second state, respectively, according to an embodiment.
Figure 14:
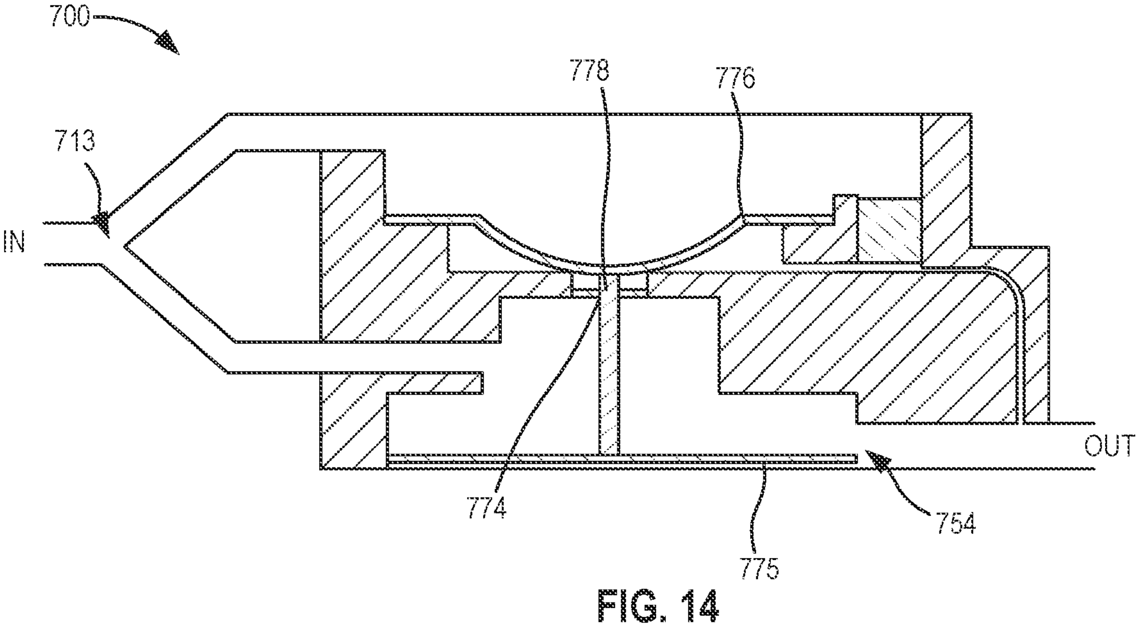

While the device 600 is described above as including the piercing member 678 that pierces the barrier 675 to place the device 600 in the second state, in other embodiments, a device can include any suitable member configured to transition any suitable barrier. For example, FIGS. 13 and 14 illustrate a device 700 according to an embodiment. The device 700 can be substantially similar to the device 600 and thus, similar portions are not described in further detail herein. The device 700 (FIGS. 13 and 14) can differ from the device 600 (FIGS. 11 and 12), however, by including a diaphragm 776 that includes and/or that is coupled to a rod, a pusher, a plunger, an actuator, and/or the like (referred to herein for simplicity as an "actuator"). Moreover, rather than including the barriers 674 and 675 that are configured to be pierced, as described above with reference to the device 600), the device 700 includes barriers 774 and 775 that can have any suitable shape, size, and/or configuration and that can be transitioned, in some instances, in any suitable manner. For example, the barrier 774 can be configured and/or otherwise disposed to form a substantially fluid tight seal with one or more inner surfaces of the device 700 and with one or more outer surfaces of the actuator 778. In this manner, the barrier 774 can limit and/or substantially prevent bodily fluid from undesirably flowing out of a fluid flow path 754 and into other portions of the device 700 (e.g., in a manner similar to that described above with reference to the barrier 674).

As shown in FIG. 13, when the device 700 is in a first state, the diaphragm 776 can be in a first state (e.g., a non-flipped, unactuated, and/or initial state). Similarly, the actuator 778 coupled to the diaphragm 776 and the barrier 775 can be in a first or initial state. As described in detail above with reference to the device 600, when the barrier 775 is in the first state, a flow path 713 of the device 700 (e.g., an inlet flow path or the like) can be sequestered from the flow path 754 (e.g., an outlet flow path or the like). In other words, the barrier 775 (e.g., a flow controller) can be configured to sequester the flow path 713 from the flow path 754. Thus, when a negative pressure is generated within a portion of the device 700 (e.g., in response to coupling a fluid collection device to an outlet of the device 700), an initial volume of bodily fluid can flow into a sequestration chamber of the device 700 (e.g., a sequestration portion of the device 700, a sequestration flow path, a sequestration reservoir or container, etc.), as described in detail above with reference to the device 600.

After the initial volume of bodily fluid is received in the sequestration chamber, the arrangement of the device 700 can be such that the diaphragm 776 flips, actuates, moves, and/or otherwise transitions from the first state (FIG. 13) to a second state (FIG. 14). As described in detail above, the movement of the diaphragm can result in a similar movement of the actuator 778 such that the actuator 778 is placed in contact with and moves and/or otherwise transitions the barrier 775 within the device 700. For example, as shown in FIG. 14, the actuator 778 can move the barrier 775 in a substantially linear motion from a first position to a second position, which in turn, can be a position in which the barrier 775 no longer sequesters the flow path 713 from the flow path 754. Thus, a subsequent volume of bodily fluid that is substantially free of contaminants can flow through the device 700 and into the fluid collection device coupled thereto. In this manner, the device 700 can be substantially similar in at least form and/or function to the device 600 and thus, is not described in further detail herein.

Figure 15:
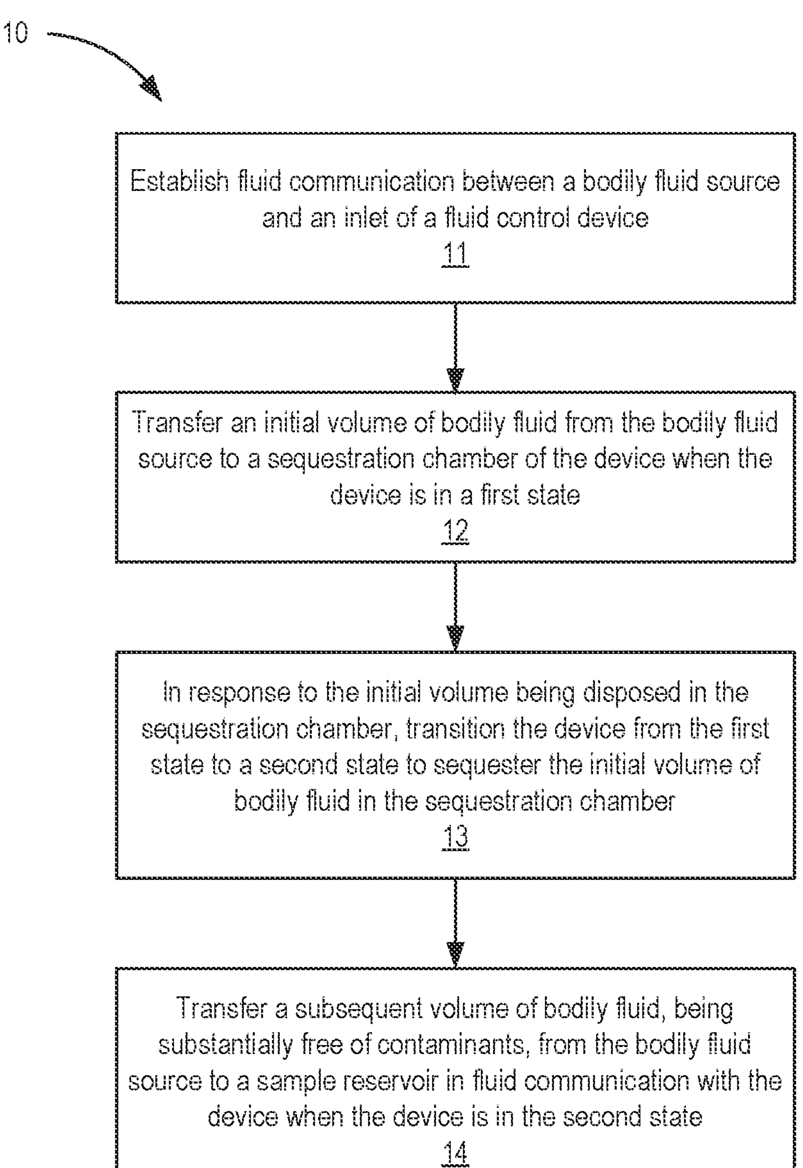
FIGS. 15 and 16 are flowcharts, each of which illustrates a method of using a fluid control device to divert an initial volume of bodily fluid to procure bodily fluid samples with reduced contamination, according to different embodiments.

Referring now to FIG. 15, a flowchart is shown illustrating a method 10 of using a fluid control device, such as those described herein, to divert an initial volume of bodily fluid to procure bodily fluid samples with reduced contamination, according to an embodiment. The fluid control device (also referred to herein as "control device") can be similar to and/or substantially the same as any of the control devices 100, 200, 300, 400, 500, 600, and/or 700 described herein.

The method 10 includes establishing fluid communication between a bodily fluid source and an inlet of the control device, at 11. In some instances, for example, the bodily fluid source can be a fluid source within a patient's body. More specifically, in some instances, the bodily fluid source can be a vein and/or vascular structure in the patient's body. As described above, the control device can be configured to couple to and/or include an inlet device such as, for example, an intravenous catheter, a butterfly needle, and/or the like. In other embodiments, the inlet device can be any suitable coupler, port, etc. configured to fluidically couple to the bodily fluid source. As such, the inlet device can be manipulated to establish fluid communication between the bodily fluid source and the fluid control device, as described in detail above.

Having established fluid communication with the bodily fluid source, an initial volume of bodily fluid is transferred from the bodily fluid source to a sequestration chamber included in and/or defined by the control device when the control device is in a first state, at 12. In some embodiments, the control device or a portion thereof (e.g., the sequestration chamber, a junction, an actuator, a flow controller, etc.) is in a first state and/or configuration prior to use. As such, establishing fluid communication with the bodily fluid source automatically establishes fluid communication with the sequestration chamber. More particularly, in some embodiments, a flow controller such as, for example, a valve, a flow restrictor, a selectively permeable member, and/or the like can be in a first state and/or configuration such a flow of at least a gas can pass and/or can be conveyed therethrough.

As described in detail herein, the initial volume can be any suitable volume of bodily fluid. For example, in some instances, the initial volume can be as small as one drop of bodily fluid (or a relatively few drops of bodily fluid). In other instances, the initial volume can be, for example, up to about 30 mL, 40 mL, 50 mL, or more. Moreover, as described in detail above with reference to specific embodiments, the initial volume can be at least partially based on and/or can be associated with an amount of bodily fluid that can be contained and/or sequestered in the sequestration chamber. In some instances, the initial volume can be at least partially based on and/or associated with a desired amount of fluid sufficient to transition the control device from an initial or first state to a subsequent or second state, using a negative pressure differential defined and/or produced by a negative pressure source coupled to the outlet of the fluid control device. In some instances, the initial volume can be at least partially based on and/or associated with a desired amount of fluid sufficient to transition one or more flow controllers included in the fluid control device from its/their first state to its/their second state. For example, in some instances one or more flow controllers can be driven and/or transitioned by a pressure differential, a predetermined and/or desired fluid volume, a fluid contact, the passage of predetermined and/or desired time, and/or the like, as described herein. In some instances, the initial volume can be a volume that is sufficient to entrain and/or contain substantially all the undesired microbes that may have been dislodged and/or the like as the fluid communication was being established between the bodily fluid source and the inlet device.

In response to the initial volume of bodily fluid being disposed in the sequestration chamber, the control device is transitioned (e.g., automatically, passively, or in response to an actuation) from the first state to the second state to sequester the initial volume of bodily fluid in the sequestration chamber, at 13. In some embodiments, for example, the initial volume of bodily fluid can fill the sequestration chamber such that any additional volume of bodily fluid is substantially prevented from entering and/or being contained in the sequestration chamber. In such embodiments, the filled sequestration chamber can form, for example, a fluid lock or the like that substantially prevents additional amounts of bodily fluid from entering the sequestration chamber and/or that substantially prevents bodily fluid from exiting the sequestration chamber. In some embodiments, the sequestration chamber can include a membrane or material interacting with the bodily fluid (e.g., a semi-permeable membrane or the like such as described above with reference to the control devices 100, 200, 300, 400, 500, 600, and/or 700). In some embodiments, the sequestration chamber and/or device can include one or more flow controllers that can be activated (e.g., diaphragms as described with reference to control device 500, 600, and/or 700, and/or any other suitable flow controller) that are activated using any suitable mechanism to draw, divert, and/or sequester bodily fluid. For example, such flow controllers can use a change in a pressure differential (e.g., a pressure differential that can occur when portions of the flow path are sealed and/or closed off from interacting with bodily fluid), as described with reference to control device 500, 600, and/or 700, or can be user activated or activated on the basis of other variables like time, gravity, or the like.

In some instances, two or more of these mechanisms can be used in combination. For example, in some embodiments, the diversion and/or sequestration of bodily fluid can be carried out using passive mechanisms (e.g., based on one or more pressure differentials and/or filling of the sequestration chamber). In other embodiments, the diversion and sequestration or fluid can also result from one or more active methods such as, for example, one or more actuators operated with or without user intervention. In some embodiments, one or more user mediated mechanisms, actuators, controllers, etc. can be included to provide additional control functions such as, for example, a supervisory or safety override function that may be used in certain settings such as, for example, during training of personnel on the use of the control devices. In other embodiments, the sequestration chamber can retain and/or sequester the initial volume of bodily fluid in any suitable manner such as those described herein and/or any suitable combination(s) thereof.

With the control device being transitioned to the second state (e.g., passively or through user intervention), a subsequent volume of bodily fluid is transferred from the bodily fluid source to a fluid collection device (e.g., any of those described herein) in fluid communication with the control device, at 14. As described in detail above, the sequestering of the initial volume of bodily fluid in the sequestration chamber can be operable to sequester any contaminants contained in the initial volume of bodily fluid in the sequestration chamber. Accordingly, the subsequent volume of bodily fluid transferred to the fluid collection device is substantially free of contaminants.

Figure 16:
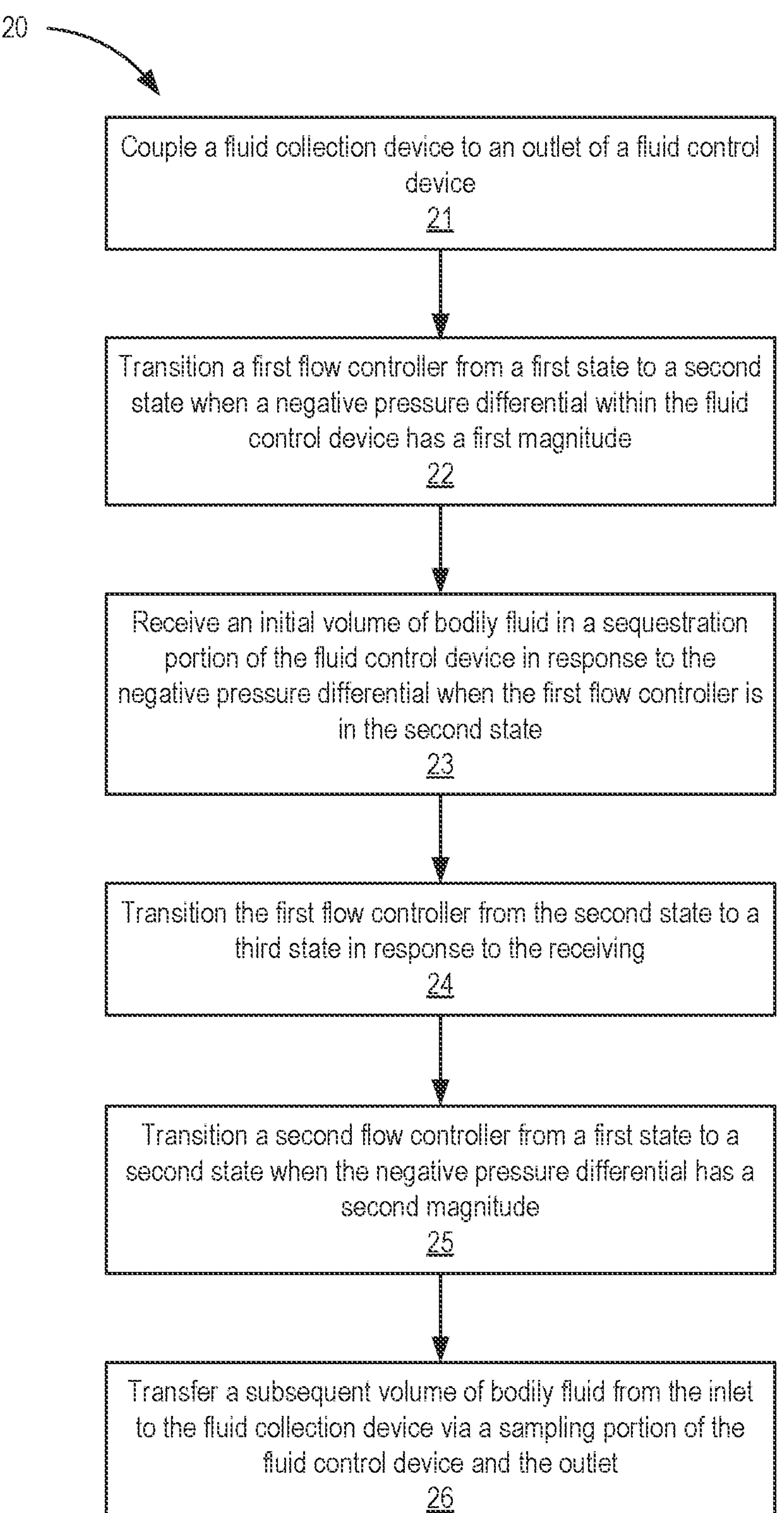

Referring now to FIG. 16, a flowchart is shown illustrating a method 20 of using a fluid control device, such as those described herein, to divert an initial volume of bodily fluid to procure bodily fluid samples with reduced contamination, according to an embodiment. The fluid control device (also referred to herein as "control device") can be similar to and/or substantially the same as any of the control devices 100, 200, 300, 400, 500, 600, and/or 700 described herein. In some embodiments, for example, the fluid control device can include an inlet configured to be placed in fluid communication with a bodily fluid source and an outlet configured to be coupled to a fluid collection device. Moreover, the fluid control device can include a sequestration portion that is in fluid communication with the inlet and a sampling portion that is in fluid communication with the outlet.

The method 20 includes coupling a fluid collection device to the outlet of the fluid control device, at 21. The fluid collection device can be any of those described herein. For example, in some embodiments, the fluid collection device can be an evacuated container, sample bottle, syringe, and/or the like. Moreover, the coupling of the fluid collection device to the outlet can be such that a negative pressure differential is produced and/or generated within at least a portion of the fluid control device, as described in detail above.

A first flow controller of the fluid control device is transitioned from a first state to a second state when the negative pressure differential within the fluid control device has a first magnitude, at 22. As described above, the first flow controller can be a valve, selectively permeable material, restricted flow path, and/or the like configured to sequester the sequestration portion of the fluid control device from the outlet when in the first state and to establish fluid communication between the sequestration portion and the outlet when in the second state, as described in detail above.

An initial volume of bodily fluid is received from the inlet of the fluid control device and into the sequestration portion of the fluid control device in response to the negative pressure differential when the first flow controller is in the second state, at 23. In some instances, for example, the inlet can be in fluid communication with a bodily fluid source such as a bodily fluid source within a patient's body (e.g., a vein and/or vascular structure in the patient's body). In some embodiments, for example, the inlet can be coupled to an inlet device such as, for example, an intravenous catheter, a butterfly needle, and/or the like, which in turn, is inserted into a portion of the patient. Thus, bodily fluid can flow from the bodily fluid source, through the inlet of the fluid control device, and into the sequestration portion.

The first flow controller is transitioned from the second state to a third state in response to the sequestration portion receiving the initial volume of bodily fluid, at 24. As described in detail herein, the initial volume can be any suitable volume such as, for example, a volume as small as one drop of bodily fluid (or a relatively few drops of bodily fluid) up to, for example, 50.0 mL or more. In some instances, the initial volume can be at least partially based on and/or associated with a desired amount of fluid sufficient to transition the first flow controller from the second state to the third state. In some instances, the initial volume can be a volume of bodily fluid that is transferred into the sequestration portion until a negative pressure differential (e.g., between the first flow controller and the inlet) is in substantial equilibrium or the like. In such instances, the first flow controller can automatically transition from the second state to the third state when the negative pressure differential operable to draw the initial volume of bodily fluid is in substantial equilibrium. In some embodiments, the first flow controller can include, for example, a selectively permeable material that can be saturated by at least a portion of the initial volume of bodily fluid to transition the first flow controller from the second state to the third state, as described in detail above. As such, the first flow controller can sequester the sequestration portion from the outlet when in the third state.

With the first flow controller in the third state, the negative pressure differential within a portion of the fluid control device can increase from the first magnitude to a second magnitude. When the negative pressure differential has the second magnitude, a second flow controller is transitioned from a first state to a second state, at 25. The second flow controller can be configured to, for example, sequester the sampling portion of the fluid control device from the inlet when in the first state and is configured to establish fluid communication between the sampling portion and the inlet when in the second state. As described above with reference to specific embodiments, the second flow controller can be any suitable control device or mechanism such as, for example, a valve, a selectively permeable material, a restricted flow path, a dissolvable material, a frangible barrier, a movable barrier, and/or the like.

As described above, a pressure differential sufficient to transition the second flow controller from the first state (e.g., a non-flow state) to the second state (e.g., a flow state) is greater than a pressure differential sufficient to transition the first flow controller from the first state (e.g., a non-flow state) to the second state (e.g., a flow state). As such, the second flow controller can be configured to transition to the second state after the first flow controller has transitioned between its first, second, and third states. Thus, a subsequent volume of bodily fluid is transferred from the inlet to the fluid collection device via the sampling portion and the outlet, at 26. As described in detail above, receiving the initial volume of bodily fluid in the sequestration portion and sequestering the sequestration portion from the outlet can be operable to sequester any contaminants contained in the initial volume of bodily fluid in the sequestration portion of the fluid control device. Accordingly, the subsequent volume of bodily fluid transferred to the fluid collection device can have reduced contamination and/or can be substantially free of contaminants.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. For example, while the control devices 100, 200, 300, 400, 500, 600, and/or 700, are described as transferring a bodily fluid into the device as a result of a negative pressure within a fluid collection device, in other embodiments, the devices described herein can be used with any suitable device configured to establish a pressure differential (e.g., a negative pressure differential). For example, in some embodiments, an outlet of a control device can be coupled to a syringe or pump. In other embodiments, a control device can include a pre-charged sequestration chamber, a vented sequestration chamber, a manually activated device configured to produce a negative pressure, an energy source, and/or any other suitable means of defining and/or forming a pressure differential within a portion of the control device.

In some other embodiments, the source of negative pressure can be associated with but independent of the fluid collection device. For example, a source of negative pressure such as a syringe, a pump, a passive source like a gravity aided or structurally aided container, etc., can be placed downstream of the outlet of the fluid control device such that the negative pressure imparted is communicated to the fluid collection device and the outlet. For example the source of negative pressure may be in fluid communication with the outlet via the fluid collection device. In other embodiments, under some circumstances, the source of negative pressure may be placed in fluid communication with the outlet to impart the pressure differential and the outlet may then be placed in fluid communication with the collection device to collect the fluid drawn by the pressure differential imparted, as described in further detail herein.

In some embodiments, any of the fluid control devices described herein can be formed from any suitable components that can be manufactured, sterilized, and packaged as individual parts or components. In such embodiments, a user can, for example, open one or more packages containing one or more components, can assemble the components to form the fluid control device, and can use the fluid control device as described above. In other embodiments, any of the fluid control devices described herein can be formed from any suitable components that can be manufactured, sterilized, assembled, and packaged as an assembly or integrated device. In such embodiments, a user can, for example, open a packaging containing such an assembly or integrated device and can use the device as described above without further assembly of components. In some embodiments, any of the control devices can be monolithically formed in whole or at least in part.

In some embodiments, any of the control devices can be physically and/or fluidically coupled to a collection device (e.g., a sample reservoir, a syringe, a blood culture bottle, a collection vial, a fluid transfer container, and/or any other suitable reservoir, collection device, and/or transfer device) by a user prior to or during use, as described in detail above. In other embodiments, any of the control devices can be physically coupled, attached, formed, and/or otherwise mated to a fluid collection device during a manufacturing process. This can be done prior to sterilization so the collection pathway(s) and connection interface(s) (e.g., where the control device couples to the fluid collection device) maintain a closed-system, mechanical diversion device within a sterile environment that is not subject to touch-point contamination from external sources.

In some embodiments, the pre-assembly of the control device and the collection device can be such that the user is forced first to sequester, segregate, and/or isolate at least a portion of the initial bodily fluid volume or flow prior to transferring a sample volume to the pre-assembled fluid collection device. For example, the control device can include an actuator that is configured to isolate an outlet from other portions of the control device, thereby isolating the collection device from such portions of the control device. Moreover, after transferring the initial volume of bodily fluid, the actuation of the actuator can result in sequestration of the initial volume of bodily fluid and the fluidic coupling of the outlet to additional portions of the control device (e.g., an inlet). In some embodiments, pre-assembling the control device and the collection device (e.g., during manufacturing) can, for example, force compliance with a sample procurement protocol that calls for the sequestration of an initial amount of bodily fluid prior to collecting a sample volume of bodily fluid.

In some embodiments, the coupling, mating, and/or attachment of the fluid control device to the fluid collection device (e.g., during manufacturing) can be executed such that the control device can be removed (physically decoupled, removed with a specific "key," and/or any other approach used to separate the control device from the fluid collection device) after use to allow access to the fluid collection device. After decoupling, the collection device can be placed in an incubator and/or any other type of analytical machine, and accessed for analysis and/or otherwise further processed. In some embodiments, such decoupling may be blocked, limited, and/or substantially prevented prior to use and unblocked or allowed after use. In other embodiments, the fluid control device and the fluid collection device can be permanently coupled and/or monolithically formed (at least in part) to prevent such decoupling.

Any of the embodiments described herein can be used in conjunction with any suitable fluid transfer, fluid collection, and/or fluid storage device such as, for example, the fluid reservoirs described in the '420 patent, the transfer devices described in the '510 publication, and/or the transfer adapters described in the '352 publication. In some embodiments, any of the embodiments described herein can be used in conjunction with fluid transfer, fluid collection, and/or fluid storage devices such as, for example, the devices described in U.S. Pat. No. 8,535,241 entitled, "Fluid Diversion Mechanism for Bodily-Fluid Sampling," filed Oct. 12, 2012; U.S. Pat. No. 9,060,724 entitled, "Fluid Diversion Mechanism for Bodily-Fluid Sampling," filed May 29, 2013; U.S. Pat. No. 9,155,495 entitled, "Syringe-Based Fluid Diversion Mechanism for Bodily-Fluid Sampling," filed Dec. 2, 2013; U.S. Patent Publication No. 2016/0361006 entitled, "Devices and Methods for Syringe Based Fluid Transfer for Bodily-Fluid Sampling," filed Jun. 13, 2016; U.S. Patent Publication No. 2018/0140240 entitled, "Systems and Methods for Sample Collection with Reduced Hemolysis," filed Nov. 20, 2017; and/or U.S. Patent Publication No. 2017/0065733 entitled, "Apparatus and Methods for Maintaining Sterility of a Specimen Container," filed Sep. 6, 2016, the disclosures of each of which are incorporated herein by reference in their entireties.

While some of the embodiments described above include a flow controller that selectively establishes fluid communication between a sequestration chamber and a fluid collection device (or other source of negative pressure) in other embodiments, a control device can be arranged to transfer a flow of bodily fluid in response to negative pressure differentials resulting from any suitable portion(s) of the device. For example, while the control device 200 is described above as including the flow controllers (e.g., the membrane 215, and/or the like) that place the sequestration chamber 214 in selective fluid communication with the fluid collection device (e.g., a sample reservoir or syringe) until the membrane 215 is transitioned to a sealed or closed state (e.g., until the membrane 215 is sufficiently wetted), in other embodiments, a control device can include a sequestration chamber that is a pre-sealed, evacuated, and/or pre-charged chamber such that establishing fluid communication between an inlet and the sequestration chamber results in a negative pressure differential that is sufficient to draw an initial volume of bodily fluid into the sequestration chamber. In such embodiments, the control device can be configured to transfer bodily fluid to the sequestration chamber until the pressure differential is sufficiently reduced and/or until pressures otherwise substantially equalize. Moreover, in some such embodiments, the sequestration chamber and/or the inlet can include a coupler, an actuator, a needle, a septum, a port, and/or any other suitable member that can establish fluid communication therebetween (e.g., that can transition the sequestration chamber from a sealed to an unsealed configuration).

While the embodiments have been described above as including particular means for modulating and/or controlling a magnitude of negative pressure applied on or through at least a portion of the device(s), in other embodiments, a control device can include any suitable feature, mechanism, and/or device configured to modulate, create, and/or otherwise control one or more pressure differentials through at least a portion of the control device. For example, in some embodiments, a user can transition and/or move an actuator to change (e.g., reduce or increase) the size of one or more portions of a fluid flow path or fluid flow interface within a portion of the control device to manually modulate and/or otherwise control an amount or magnitude of negative pressure within one or more portions of a control device.

By way of another example, any of the embodiments described herein can include any suitable actuator and/or flow controller configured to selectively control fluid flow through at least a portion of the device. Specifically, a flow controller or the like can be one or more of a selectively permeable material or membrane, a valve, a diaphragm, and/or any other suitable flow controller. While some of the embodiments have been described as including an actuator rod configured to be transitioned from a first configuration or position to a second configuration or position, in other embodiments, any actuator described herein can include an actuator rod configured to transition from between a first position and second position to at least temporarily isolate an outlet from of the device from one or more other portions of the device. In some embodiments, such an actuator can be configured for use with a given and/or predetermined collection device such as, for example, a syringe. In other embodiments, such an actuator can be used with any suitable collection device.

While the embodiments have been described above as including or coupling to an inlet device such as a needle or the like that is configured to puncture the skin of a patient to place the lumen of the needle in fluid communication with a vein in the patient, in other embodiments, a fluid control device can include and/or can couple to any suitable inlet device. For example, in some embodiments, an inlet device can include a trocar or the like and a catheter. The trocar is configured to puncture the skin of a patient and then configured to be withdrawn from the patient, leaving the catheter of the inlet device placed within the patient. In other embodiments, the inlet device need not puncture the skin of a patient. For example, in some embodiments, the inlet device can include a needle or catheter that can be placed in a dish, well, sample volume, container, reservoir, etc. In still other embodiments, the inlet device can be and/or can include a coupler or port configured to couple to an indwelling needle or intravenous catheter. In other embodiments, such a coupler or port can be configured to couple to any suitable bodily fluid source (or port thereof) such as, for example, a syringe, a reservoir, a container, etc.

Accordingly, while the embodiments are described above as withdrawing and sequestering an initial volume of bodily fluid to sequester contaminants such as, for example, dermally-residing microbes, in other embodiments, the inlet device can be coupled to any suitable bodily fluid source and the control device can be configured to sequester an initial volume of bodily fluid withdrawn from that bodily fluid source to sequester contaminants that may be present within the source and/or any an interface of the container or reservoir containing the bodily fluid. For example, in some embodiments, a needle of an inlet device can be configured to puncture a port or surface of a reservoir to place the needle in fluid communication with an interior volume of the container or device. In such embodiments, the devices described herein can be used to sequester an initial volume of bodily fluid from the bodily fluid source, which in turn, can sequester contaminants or the like that may have been present on the interface, port, or surface that was punctured. Thus, the devices and methods described herein can be used to procure bodily fluid samples having reduced contamination from any suitable bodily fluid source. Moreover, while some such contaminants are described herein as being dermally residing microbes, it should be understood that the contaminants can be any contaminant that is, for example, exterior to the bodily fluid source and/or otherwise that is or that includes any constituent component (e.g., microbe, virus, molecule, particle, element, etc.) that is otherwise foreign to the bodily fluid.

Although various embodiments have been described as having particular features, concepts, and/or combinations of components, other embodiments are possible having any combination or sub-combination of any features, concepts, and/or components from any of the embodiments described herein. For example, as described above, the device 700 includes concepts, features, and/or elements of the device 600, the device 600 includes concepts, features, and/or elements of the device 500, and the device 400 includes concepts, features, and/or elements of the devices 200 and 300. The specific configurations of the various components can also be varied. For example, the size and specific shape of the various components can be different from the embodiments shown, while still providing the functions as described herein. More specifically, the size and shape of the various components can be specifically selected for a desired rate and/or volume of bodily fluid flow into a fluid reservoir. Likewise, the size and/or shape of the various components can be specifically selected for a desired or intended usage. Thus, it should be understood that the size, shape, and/or arrangement of the embodiments and/or components thereof can be adapter for a given use unless the context explicitly states otherwise.

In some embodiments, the specific configurations of the various components can also be varied. For example, the size and specific shape of the various components can be different from the embodiments shown, while still providing the functions as described herein. More specifically, the size and shape of the various components can be specifically selected for a desired rate and/or volume of bodily fluid flow into a fluid reservoir. Likewise, the size and/or shape of the various components can be specifically selected for a desired or intended usage. For example, in some embodiments, a device such as those described herein can be configured for use with or on seemingly healthy adult patients. In such embodiments, the device can include a sequestration chamber that has a first volume (e.g., about 0.5 ml to about 5.0 ml). In other embodiments, a device such as those described herein can be configured for use with or on, for example, very sick patients and/or pediatric patients. In such embodiments, the device can include a sequestration chamber that has a second volume that is less than the first volume (e.g., less than about 0.5 ml). Thus, it should be understood that the size, shape, and/or arrangement of the embodiments and/or components thereof can be adapted for a given use unless the context explicitly states otherwise.

Although not shown, any of the devices described herein can include an opening, port, coupler, septum, Luer-Lok, gasket, valve, threaded connecter, standard fluidic interface, etc. (referred to for simplicity as a "port") in fluid communication with the sequestration chamber. In some such embodiments, the port can be configured to couple to any suitable device, reservoir, pressure source, etc. For example, in some embodiments, the port can be configured to couple to a reservoir, which in turn, can allow a greater volume of bodily fluid to be diverted and/or transferred into the sequestration chamber. In other embodiments, the port can be coupled to a negative pressure source such as an evacuated container, a pump, a syringe, and/or the like to collect a portion of or the full volume of bodily fluid in the sequestration chamber, channel, reservoir, etc. and use that volume of bodily fluid (e.g., the pre-sample volume) for additional clinical and/or in vitro diagnostic testing purposes. In other embodiments, the port can be coupled to any suitable pressure source or infusion device configured to infuse the initial volume of bodily fluid sequestered in the sequestration chamber back into the patient and/or bodily fluid source (e.g., in the case of pediatric patients, very sick patients, patients having a low blood volume, and/or the like).

In some embodiments, the port can be configured to receive a probe, sampling tool, testing device, and/or the like that can be used to perform one or more tests (e.g., tests not sensitive to potential contamination) on the initial volume while the initial volume is disposed or sequestered in the sequestration chamber. In other embodiments, the sequestration channel, chamber, and/or reservoir can be configured with the addition of other diagnostic testing components integrated into the chamber (e.g., a paper test) such that the initial bodily fluid is used for that test. In still other embodiments, the sequestration chamber, channel, and/or reservoir can be designed, sized, and configured to be removable and compatible with testing equipment and/or specifically accessible for other types of bodily fluid tests commonly performed on patients with suspected conditions. By way of example, a patient with suspected sepsis commonly has blood samples collected for lactate testing, procalcitonin testing, and blood culture testing. All of the fluid control devices described herein can be configured such that the sequestration chamber, channel, reservoir, etc. can be removed (e.g., after receiving the initial volume of bodily fluid) and the bodily fluid contained therein can be used for these additional testing purposes before or after the subsequent sample is collected for microbial testing.

Although not shown, in some embodiments, a fluid control device can include one or more lumen, channels, flow paths, etc. configured to selectively allow for a "bypass" flow of bodily fluid, where an initial amount or volume of bodily fluid can flow from the inlet, through the lumen, cannel, flow path, etc. to bypass the sequestration chamber, and into the collection device. In some embodiments, the fluid control device can include an actuator having, for example, at least three states—a first in which bodily fluid can flow from the inlet to the sequestration chamber, a second in which bodily fluid can flow from the inlet to the outlet after the initial volume is sequestered in the sequestration chamber, and a third in which bodily fluid can flow from the inlet, through the bypass flow path, and to the outlet. In other embodiments, the control device can include a first actuator configured to transition the device between a first and second state, as described in detail above with reference to specific embodiments, and can include a second actuator configured to transition the device to a bypass configuration or the like. In still other embodiments, the control device can include any suitable device, feature, component, mechanism, actuator, controller, etc. configured to selectively place the fluid control device in a bypass configuration or state.

In some embodiments, a method of using a fluid control device employing an external negative pressure source can include the ordered steps of establishing fluid communication between a bodily fluid source (e.g., a vein of a patient or the like) and an inlet of the fluid control device. An outlet of the fluid control device is then placed in fluid communication with and/or otherwise engages a negative pressure source. Such a negative pressure source can be a sample reservoir, a syringe, an evacuated container, an intermediate transfer device, and/or the like. The fluid control device can be in a first state or operating mode when the outlet is coupled to the negative pressure source and, as such, a negative pressure differential is applied through at least a portion of the fluid control device that can be operable to draw an initial volume of bodily fluid into a sequestration chamber of the fluid control device. Once the initial volume of bodily fluid is disposed in the sequestration chamber, the fluid control device is transitioned, either automatically or via user intervention, from the first state or operating mode to a second state or operating mode such that (1) the initial volume is sequestered in the sequestration chamber and (2) fluid communication is established between the inlet and the outlet. The sequestration of the initial volume can be such that contaminants entrained in the flow of the initial volume are likewise sequestered within the sequestration chamber. With the initial volume of bodily fluid sequestered in the sequestration chamber and with fluid communication established between the inlet and the outlet, subsequent volumes of bodily fluid that are substantially free of contamination can be collected in one or more sample reservoirs.

While the method of using the fluid control device is explicitly described as including the recited ordered steps, in other embodiments, the ordering of certain events and/or procedures in any of the methods or processes described herein may be modified and such modifications are in accordance with the variations of the invention. Additionally, certain events and/or procedures may be performed concurrently in a parallel process when possible, as well as performed sequentially as described above. Certain steps may be partially completed or may be omitted before proceeding to subsequent steps.

For example, while the devices are described herein as transitioning from a first state to a second state in a discrete operation or the like, it should be understood that the devices described herein can be configured to automatically and/or passively transition from the first state to the second state and that such a transitioning may occur over a period of time. In other words, the transitioning from the first state to the second state may, in some instances, be relatively gradual such that as a last portion of the initial volume of bodily fluid is being transferred into the sequestration chamber, the housing begins to transition from the first state to the second state. In some instances, the rate of change when transitioning from the first state to the second state can be selectively controlled to achieve one or more desired characteristics associated with the transition. Moreover, in some such instances, the inflow of the last portion of the initial volume can limit and/or substantially prevent bodily fluid already disposed in the sequestration chamber from escaping therefrom. Accordingly, while the transitioning from the first state to the second state may occur over a given amount of time, the sequestration chamber can nonetheless sequester the volume of bodily fluid disposed therein.

What is claimed:

1. A fluid control device, the device comprising:

an inlet fluidically coupleable to a bodily fluid source;

an outlet fluidically coupleable to a fluid collection device, the fluid control device configured such that a negative pressure differential between the outlet and the inlet is generated as a result of the outlet being fluidically coupled to the fluid collection device;

a containment channel between the inlet and the outlet, the containment channel including a first flow controller, the first flow controller in a first state configured to allow a gas but not a bodily fluid to flow from the containment channel to the outlet such that a volume of the bodily fluid is drawn from the inlet into the containment channel, the first flow controller in a second state configured to prevent the bodily fluid from flowing therethrough; and a sampling channel between the inlet and the outlet, the sampling channel in fluid communication with a second flow controller, the second flow controller including a diaphragm and a barrier, the diaphragm defining a portion of the containment channel, the barrier in a first position configured to obstruct the sampling channel, the barrier in a second position configured to allow a subsequent volume of the bodily fluid to flow from the inlet, through the sampling channel, and to the outlet, the first flow controller in the first state configured to allow the gas to flow from the containment channel to the outlet such that a difference in pressure across the diaphragm generated by the outlet being fluidically coupled to the fluid collection device is insufficient to transition the diaphragm from a first configuration to a second configuration, the first flow controller configured to transition from the first state to the second state when the volume of the bodily fluid is in the containment channel such that the difference in pressure across the diaphragm builds to an extent operable to transition the diaphragm to the second configuration, the diaphragm configured to move the barrier of the second flow controller from the first position to the second position due to the diaphragm transitioning.

2. The device of claim 1, further comprising:

the fluid collection device, wherein the fluid collection device is a sample bottle that is at least partially evacuated and configured to generate the negative pressure differential when the sample bottle is fluidically coupled to the outlet.

3. The device of claim 1, further comprising:

the fluid collection device, wherein the fluid collection device is a syringe that is configured to be manipulated after the outlet is fluidically coupled to the syringe to generate the negative pressure differential.

4. The device of claim 1, wherein the first flow controller includes a selectively permeable material, the first flow controller configured to transition from the first state to the second state in response to at least a portion of the volume of the bodily fluid in the containment channel saturating the selectively permeable material.

5. The device of claim 1, wherein the first flow controller in the first state is configured such that the difference in pressure across the diaphragm remains below a threshold difference in pressure, and the first flow controller in the second state is configured such that the difference in pressure across the diaphragm exceeds the threshold difference in pressure.

6. The device of claim 1, wherein the first flow controller is configured to transition from the first state to the second state automatically.

7. The device of claim 1, wherein the barrier in the first position is configured such that a first side of the barrier is in fluid communication with the inlet and a second side of the barrier is in fluid communication with the outlet.

8. The device of claim 1, wherein the containment channel has a first volume when the diaphragm is in the first configuration and has a second volume when the diaphragm is in the second configuration, the second volume being greater than the first volume.

9. A fluid control device, the device comprising:

an inlet fluidically coupleable to a bodily fluid source;

an outlet fluidically coupleable to a fluid collection device;

a containment reservoir in fluid communication with the inlet;

a sampling channel in fluid communication with the outlet;

a first flow controller disposed between the containment reservoir and the outlet, the first flow controller in a first state configured to allow a gas to flow through the containment reservoir and to the outlet, the first flow controller in a second state configured to prevent the gas and a bodily fluid from flowing through the first flow controller toward the outlet; and a second flow controller including a diaphragm and a barrier, the diaphragm defining a portion of the containment reservoir, the barrier being movable within the sampling channel between a first position in which the barrier is configured to prevent the bodily fluid from flowing through the sampling channel from the inlet to the outlet, to a second position in which the barrier is configured to allow the bodily fluid to flow from the inlet, through the sampling channel, and to the outlet, the first flow controller in the first state configured to allow a volume of the bodily fluid to be received in the containment reservoir at least partially in response to a first portion of a negative pressure differential that is generated by the outlet being fluidically coupled to the fluid collection device and that is applied across the first flow controller, the first flow controller configured to transition to the second state when the volume of the bodily fluid is in the containment reservoir thereby causing a second portion of the negative pressure differential that is generated by the outlet being fluidically coupled to the fluid collection device and that is applied across the diaphragm of the second flow controller to build to an extent operable to transition the diaphragm from a first configuration to a second configuration, the second flow controller configured such that the diaphragm moves the barrier from the first position to the second position due to the diaphragm transitioning from the first configuration to the second configuration.

10. The device of claim 9, wherein the first flow controller is configured to automatically transition from the first state to the second state.

11. The device of claim 9, wherein the first flow controller includes a selectively permeable material that allows the gas but not the bodily fluid to flow through the first flow controller in the first state and that prevents both the gas and the bodily fluid from flowing through the first flow controller in the second state.

12. The device of claim 11, wherein the first flow controller is configured to be transitioned from the first state to the second state in response to at least a portion of the volume of the bodily fluid in the containment reservoir saturating the selectively permeable material.

13. The device of claim 9, wherein the diaphragm is configured to be transitioned from the first configuration to the second configuration when the second portion of the negative pressure differential applied across the diaphragm exceeds a threshold pressure differential.

14. The device of claim 13, wherein the first flow controller in the first state is configured to allow the gas to flow through the first flow controller such that the second portion of the negative pressure differential applied across the diaphragm of the second flow controller remains below the threshold pressure differential.

15. The device of claim 9, wherein the first position of the barrier is a first position within the sampling channel and the second position of the barrier is a second position within the sampling channel.

16. The device of claim 9, wherein the barrier in the first position is configured such that a first side of the barrier is in fluid communication with the inlet and a second side of the barrier is in fluid communication with the outlet.

17. The device of claim 9, wherein the containment reservoir has a first volume when the diaphragm is in the first configuration and has a second volume when the diaphragm is in the second configuration, the second volume being greater than the first volume.

18. A fluid control device, the device comprising:

a housing having an inlet fluidically coupleable to a bodily fluid source and an outlet fluidically coupleable to a fluid collection device, the housing defining a containment channel between the inlet and the outlet and defining a sampling channel between the inlet and the outlet;

a first flow controller disposed within the housing and configured to allow a gas but not a bodily fluid to flow therethrough from the containment channel and toward the outlet when in a first state and to prevent the gas and the bodily fluid from flowing therethrough when in a second state; and a second flow controller disposed within the housing and configured to prevent the gas and the bodily fluid from flowing through the sampling channel to the outlet when in a first configuration and to allow the bodily fluid to flow through the sampling channel from the inlet toward the outlet when in a second configuration, the second flow controller including a diaphragm and a barrier, the first flow controller in the first state and the second flow controller in the first configuration collectively configured to allow a volume of the bodily fluid to be received in the containment channel at least partially in response to a negative pressure differential generated by the outlet being fluidically coupled to the fluid collection device, the first flow controller in the first state allowing a first portion of the negative pressure differential across the first flow controller such that a second portion of the negative pressure differential across the diaphragm of the second flow controller is insufficient to transition the second flow controller from the first configuration to the second configuration, the first flow controller configured to transition to the second state based on the volume of the bodily fluid in the containment channel thereby causing the second portion of the negative pressure differential across the diaphragm to build to an extent operable to switch the diaphragm from a first configuration to a second configuration, the second flow controller configured such that the diaphragm moves the barrier from a first position to a second position due to the diaphragm switching from the first configuration to the second configuration, thereby transitioning the second flow controller from the first configuration to the second configuration.

19. The device of claim 18, wherein the second flow controller is configured to be transitioned from the first configuration to the second configuration to open the sample channel to allow a subsequent volume of the bodily fluid to flow from the inlet towards the outlet.

20. The device of claim 18, wherein the first flow controller includes a selectively permeable material that allows the gas but not the bodily fluid to flow through the first flow controller in the first state and that prevents both the gas and the bodily fluid from flowing through the first flow controller is in the second state.

21. The device of claim 20, wherein the first flow controller is configured to be transitioned from the first state to the second state in response to the volume of the bodily fluid in the containment channel saturating the selectively permeable material.

22. The device of claim 18, wherein the barrier in the first position forms a seal with an inner surface of the housing defining a portion of the sampling channel.

23. The device of claim 22, wherein the barrier is configured block at least the portion of the sampling channel from the inlet when in the first position and is configured to allow fluid communication between the inlet and the sampling channel when in the second position.

24. The device of claim 18, wherein the first flow controller in the first state is configured to facilitate the negative pressure differential between the inlet and the outlet via the containment channel and the first flow controller, and the first flow controller in the second state and the second flow controller in the second configuration are configured collectively to facilitate the negative pressure differential between the inlet and the outlet via the sampling channel such that a subsequent volume of the bodily fluid is drawn into the fluid collection device for testing.

25. The device of claim 18, wherein the barrier in the first position is configured such that a first side of the barrier is in fluid communication with the inlet and a second side of the barrier opposite the first side is in fluid communication with the outlet.

26. The device of claim 18, wherein the diaphragm defines a portion of the containment channel.

27. The device of claim 26, wherein the containment channel has a first volume when the diaphragm is in the first configuration and has a second volume when the diaphragm is in the second configuration, the second volume being greater than the first volume.

* * * * *